US012716086B2

(12) United States Patent
Dewal

(10) Patent No.: US 12,716,086 B2
(45) Date of Patent: Aug. 25, 2026

(54) ACRYLATE DERIVATIVES AND USES THEREOF

(71) Applicant: Expansion Technologies, Cambridge, MA (US)

(72) Inventor: Mahender Babu Dewal, Arlington, MA (US)

(73) Assignee: EXPANSION TECHNOLOGIES, Cambridge, MA (US)

( * ) Notice: Subject to any disclaimer, the term of this patent is extended or adjusted under 35 U.S.C. 154(b) by 704 days.

(21) Appl. No.: 18/118,400

(22) Filed: Mar. 7, 2023

(65) Prior Publication Data

US 2023/0279476 A1 Sep. 7, 2023

Related U.S. Application Data

(60) Provisional application No. 63/317,195, filed on Mar. 7, 2022.

(51) Int. Cl.

| | |
|---|---|
| ***C12Q 1/6841*** | (2018.01) |
| ***C07C 231/02*** | (2006.01) |
| ***C07C 233/20*** | (2006.01) |
| ***C07C 233/38*** | (2006.01) |
| ***C07C 233/49*** | (2006.01) |
| ***C07D 207/46*** | (2006.01) |
| ***C07H 21/00*** | (2006.01) |
| ***C07K 1/13*** | (2006.01) |
| ***G01N 33/68*** | (2006.01) |

(52) U.S. Cl.

CPC .......... *C12Q 1/6841* (2013.01); *C07C 231/02* (2013.01); *C07C 233/20* (2013.01); *C07C 233/38* (2013.01); *C07C 233/49* (2013.01); *C07D 207/46* (2013.01); *C07H 21/00* (2013.01); *C07K 1/13* (2013.01); *G01N 33/68* (2013.01); *C12Q 2600/16* (2013.01)

(58) Field of Classification Search

CPC ........ C07K 1/13; C07H 21/00; C07D 207/46; C12Q 1/6841; C12Q 2600/16; C07C 231/02; C07C 233/20; C07C 233/38; C07C 231/49

See application file for complete search history.

(56) References Cited

U.S. PATENT DOCUMENTS

| | | | |
|---|---|---|---|
| 10,059,990 B2 | 8/2018 | Boyden et al. | |
| 10,309,879 B2 | 6/2019 | Chen et al. | |
| 10,317,321 B2 | 6/2019 | Tillberg et al. | |
| 10,364,457 B2 | 7/2019 | Wassie et al. | |
| 10,526,649 B2 | 1/2020 | Chen et al. | |
| 10,563,257 B2 | 2/2020 | Boyden et al. | |
| 10,995,361 B2 | 5/2021 | Chen et al. | |
| 2016/0305856 A1 | 10/2016 | Boyden et al. | |
| 2018/0052081 A1 | 2/2018 | Kohman | |
| 2019/0032128 A1 | 1/2019 | Chen et al. | |
| 2019/0055597 A1 | 2/2019 | Boyden et al. | |
| 2020/0041514 A1 | 2/2020 | Boyden et al. | |
| 2020/0239946 A1* | 7/2020 | Dewal | C12Q 1/6841 |
| 2020/0354782 A1* | 11/2020 | Dewal | G01N 1/30 |
| 2021/0215580 A1 | 7/2021 | Kohman | |

FOREIGN PATENT DOCUMENTS

| | | |
|---|---|---|
| WO | WO 2015/127183 | 8/2015 |
| WO | WO 2017/027367 | 2/2017 |
| WO | WO 2017/027368 | 2/2017 |
| WO | WO 2017/147435 | 8/2017 |
| WO | WO 2018/136856 | 7/2018 |
| WO | WO 2018/157048 | 8/2018 |
| WO | WO 2018/157074 | 8/2018 |
| WO | WO 2019/023214 | 1/2019 |
| WO | WO 2019/075091 | 4/2019 |
| WO | WO 2019/103996 | 5/2019 |
| WO | WO 2020/142490 | 7/2020 |

OTHER PUBLICATIONS

Chen et al., "Expansion microscopy", Science, Jan. 30, 2015;347(6221):543-8. doi: 10.1126/science.1260088. (Epub Jan. 15, 2015).

Wetmur, "DNA Probes: Applications of the Principles of Nucleic Acid Hybridization," Critical Reviews in Biochemistry and Molecular Biology, 26(3/):227-259 (1991).

Henikoff et al., "Amino acid substitution matrices from protein blocks", Proc. Natl. Acad. Sci. USA, Nov. 1992; 89:10915-10919.

Chemistry of Crosslinking, Thermo Fisher Scientific, https://www.thermofisher.com/us/en/home/lile-science/protein-biology/protein-biology-learning-center/protein-biology-resource-library/pierce-protein-methods/chemistry-crosslinking.html (pulled from Internet Jul. 14, 2023; 10 pages).

Prim et al., "ADIBO-Based "Click" Chemistry for Diagnostic Peptide Micro-Array Fabrication: Physicochemical and Assay Characteristics", Molecules, Aug. 2013, 18: 9833-9849.

Alon et al., "Expansion sequencing: Spatially precise in situ transcriptomics in intact biological systems", Science, Jan. 29, 2021; vol. 371, Issue 6528; https://doi.org/10.1126/science.aax2656 (Downloaded from https://www.science.org on Jul. 20, 2023).

* cited by examiner

*Primary Examiner* — Erich A Leeser

(74) *Attorney, Agent, or Firm* — Mark S. Cohen; PEARL COHEN LLP

(57) ABSTRACT

This disclosure relates to new cross-linking reagents for incorporating proteins and nucleic acids into polyelectrolyte gels, for use in expansion microscopy and other methods.

9 Claims, No Drawings

ACRYLATE DERIVATIVES AND USES THEREOF

CROSS-REFERENCE TO RELATED APPLICATIONS

This application claims priority to U.S. provisional patent application Ser. No. 63/317,195, filed Mar. 7, 2022, which is incorporated herein by reference in its entirety.

FIELD

The disclosure relates to reagents used in procedures such as expansion microscopy, for labelling and analyzing biological samples, such as cells and tissues.

BACKGROUND

Expansion microscopy (ExM) is an emerging novel technology which physically expands biological samples allowing super resolution microscopy to be performed using conventional diffraction limited microscopes. This technique uses inexpensive reagents and equipment and can allow multicolor, three-dimensional imaging of cells and tissue at nanometer resolution. ExM technique perfectly fits into the flow of standard immunohistochemical and immunocytochemical (IHC/ICC) and in situ hybridization (ISH) protocols where the fixed specimen (e.g., tissue/cultured cells) is stained with fluorescently labelled molecules, antibodies, etc.

However, ExM has four additional steps including: 1) anchoring 2) polymerization 3) digestion homogenization and 4) expansion, that the specimen goes through prior to the imaging. In the Anchoring step, tissue sections are incubated with small molecule chemical entities that comprise, for example, an acrylate handle and moieties that covalently conjugates to the native biomolecules including proteins, antibodies and nucleic acids in the specimen.

Currently, some commercially available molecules such as succinimidyl ester of 6-((acryloyl)amino)hexanoic acid (Acryloyl-X), methacrylic acid N-hydroxysuccinimide ester, acrylic acid N-hydroxysuccinimide ester, N—N'-(4-(2-chloroethyl)-methylamino-benzylamine-3-aminopropyl-N,N-dimethyl-3-aminopropylammonium, are available.

Having additional and improved reagents for incorporating proteins and nucleic acids into polymer gels are needed.

SUMMARY

In one aspect, a compound is provided of Formula (I)

(I)

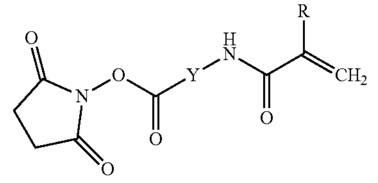

wherein Y is selected from among:

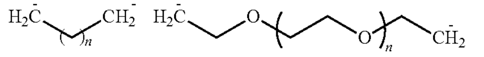

-continued

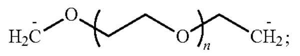

n is 1, 2, 3, 4, 5, 6, 7 or 8; and

R is selected from hydrogen, deuterium, halo, —CN, —$NO_2$, and an optionally substituted aliphatic, alicyclic, heteroaliphatic, heterocyclic, aromatic, acyl or heteroaromatic group.

In one aspect, a compound is provided of Formula IIA or IIB:

(IIA)

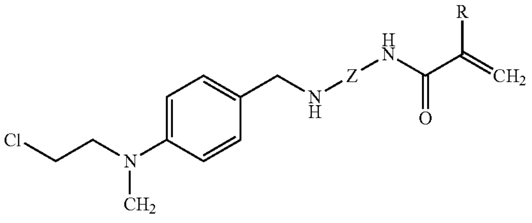

(IIB)

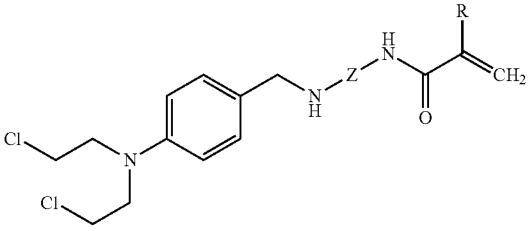

wherein Z is selected from among:

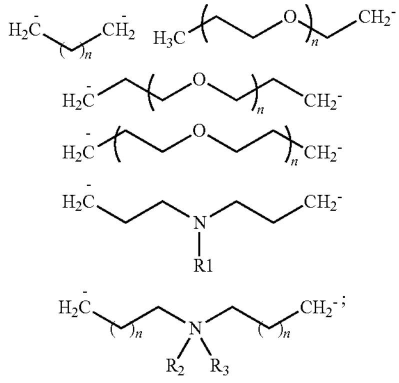

each occurrence of n is independently 1, 2, 3, 4, 5, 6, 7 or 8;

R is selected from hydrogen, deuterium, halo, —CN, —$NO_2$, and an optionally substituted aliphatic, alicyclic, heteroaliphatic, heterocyclic, aromatic, acyl or heteroaromatic group; and R1, R2 and R3 are independently H, alkyl, acyl or allyl.

In one aspect, a compound is provided of Formula (IIIA) or (IIIB):

(IIIA)

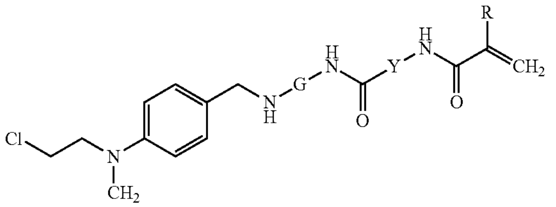

(IIIB)

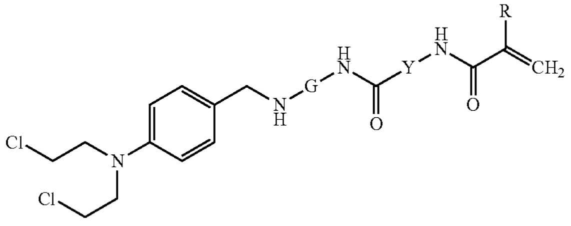

wherein G is selected from among:

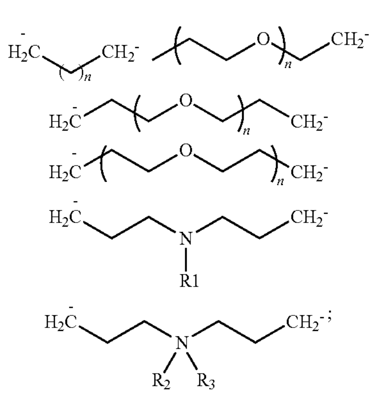

Y is selected from:

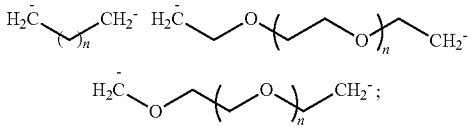

each occurrence of n is independently 1, 2, 3, 4, 5, 6, 7 or 8;

R is selected from hydrogen, deuterium, halo, —CN, —$NO_2$, and an optionally substituted aliphatic, alicyclic, heteroaliphatic, heterocyclic, aromatic, acyl or heteroaromatic group; and R1, R2 and R3 is independently H, alkyl, acyl or allyl.

In one aspect, a method is provided for preparing a compound of Formula I by:

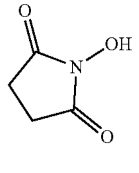

+

-continued

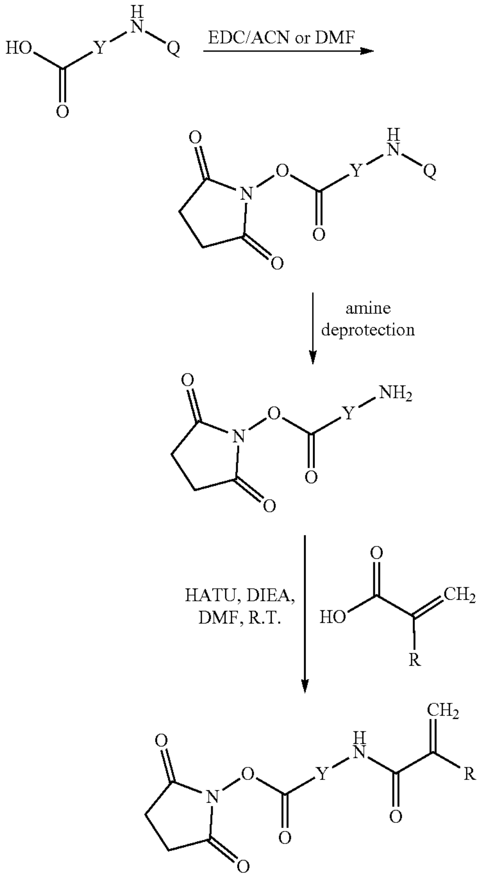

I

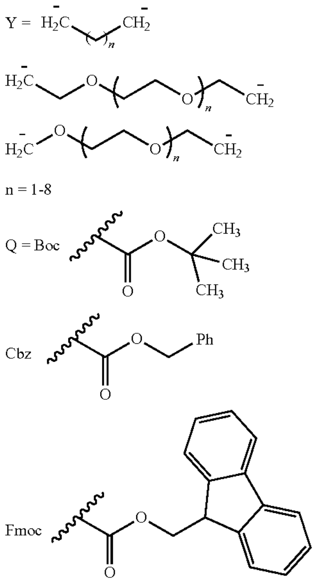

wherein the definitions of Y, Q and n are shown in the above scheme and R is selected from hydrogen, deuterium, halo, —CN, —$NO_2$, and an optionally substituted aliphatic, alicyclic, heteroaliphatic, heterocyclic, aromatic, acyl or heteroaromatic group.

In one aspect, a method is provided for preparing a compound of Formula IIA by:

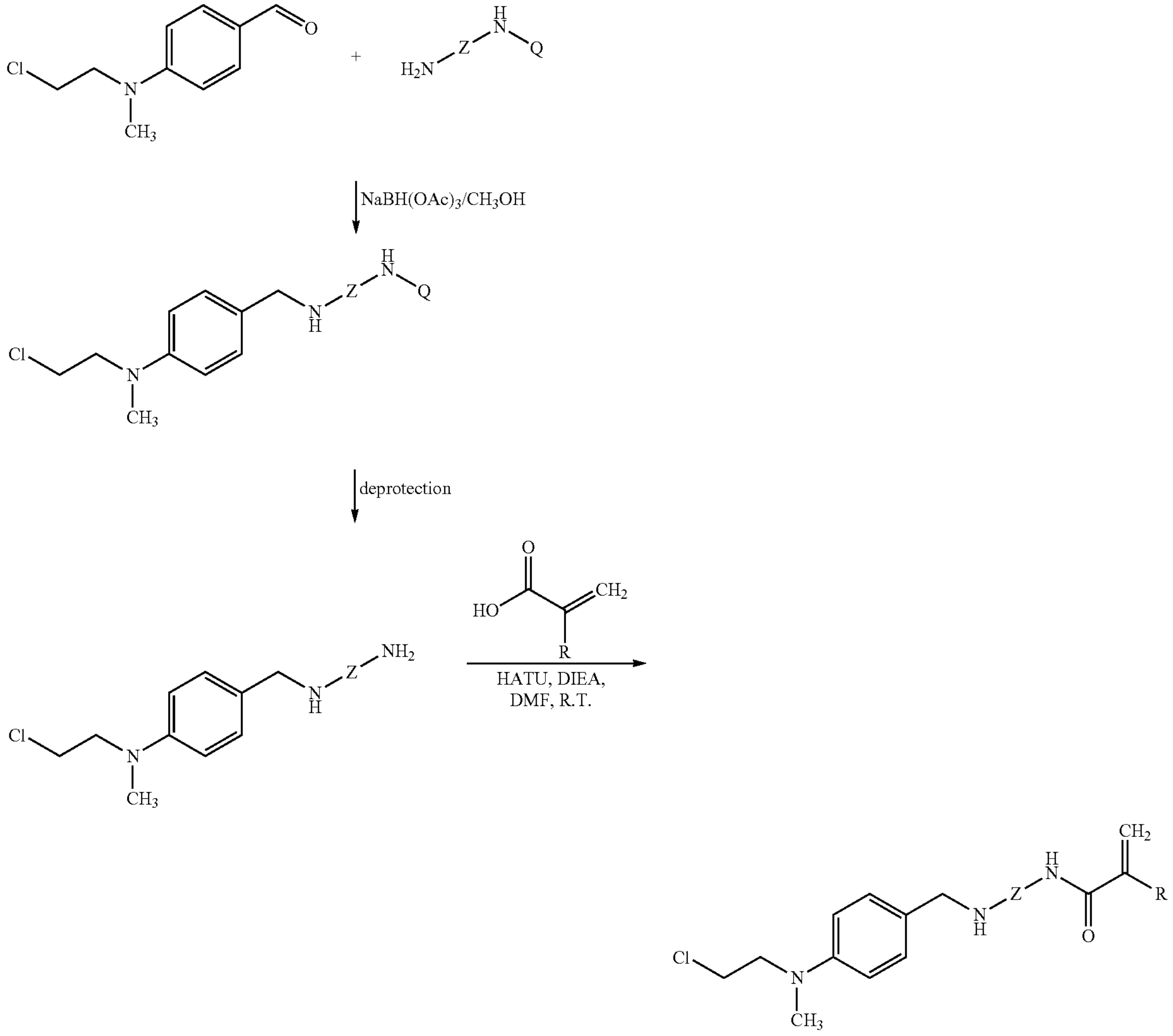
IIA
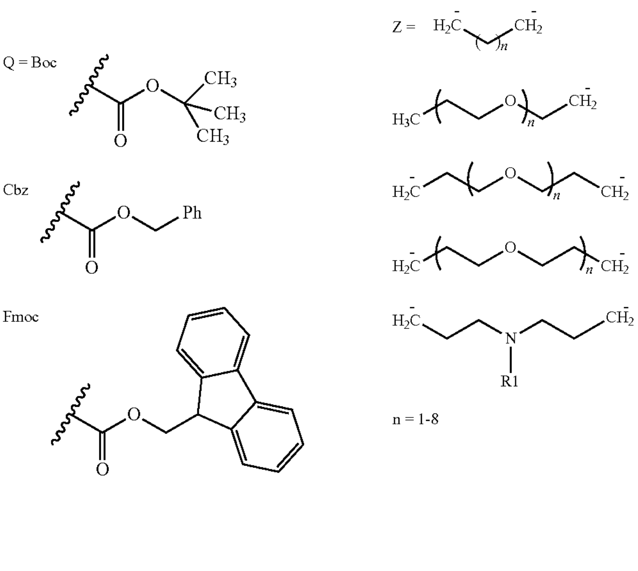
Q = Boc
Cbz
Fmoc
Z =
n = 1-8 wherein the definitions of Z, Q and n are shown in the above scheme; R is selected from hydrogen, deuterium, halo, —CN, —$NO_2$, and an optionally substituted aliphatic, alicyclic, heteroaliphatic, heterocyclic, aromatic, acyl or heteroaromatic group; and R1 is H, alkyl, acyl or allyl.

In one aspect, a method is provided for preparing a compound of Formula IIA by:

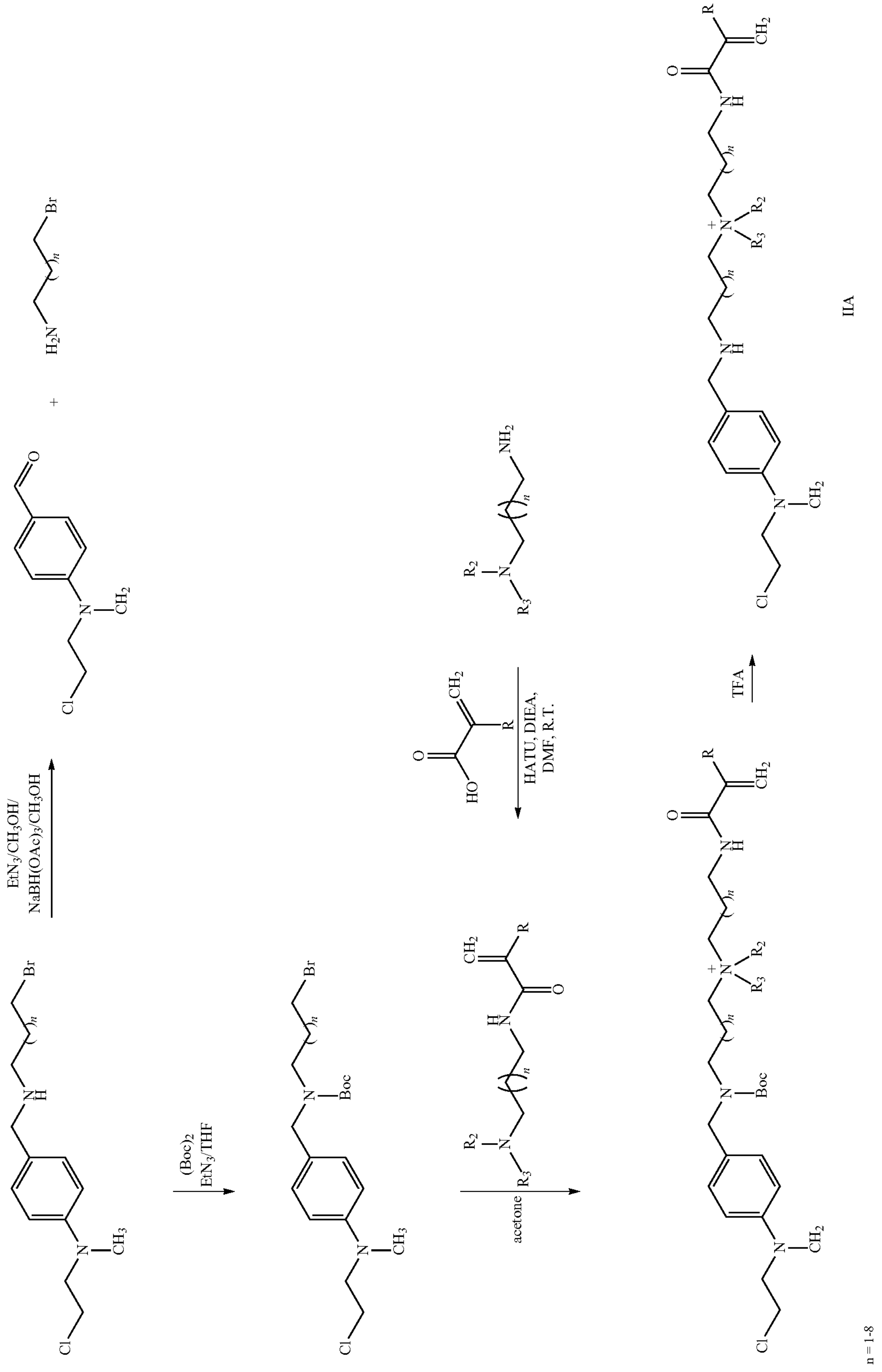
IIA
n = 1-8 wherein each occurrence of n is independently 1-8; R is selected from hydrogen, deuterium, halo, —CN, —$NO^2$, and an optionally substituted aliphatic, alicyclic, heteroaliphatic, heterocyclic, aromatic, acyl or heteroaromatic group; and R2 and R3 are independently selected from H, alkyl, acyl or allyl.

In one aspect, a method is provided for preparing a compound of Formula IIB by:

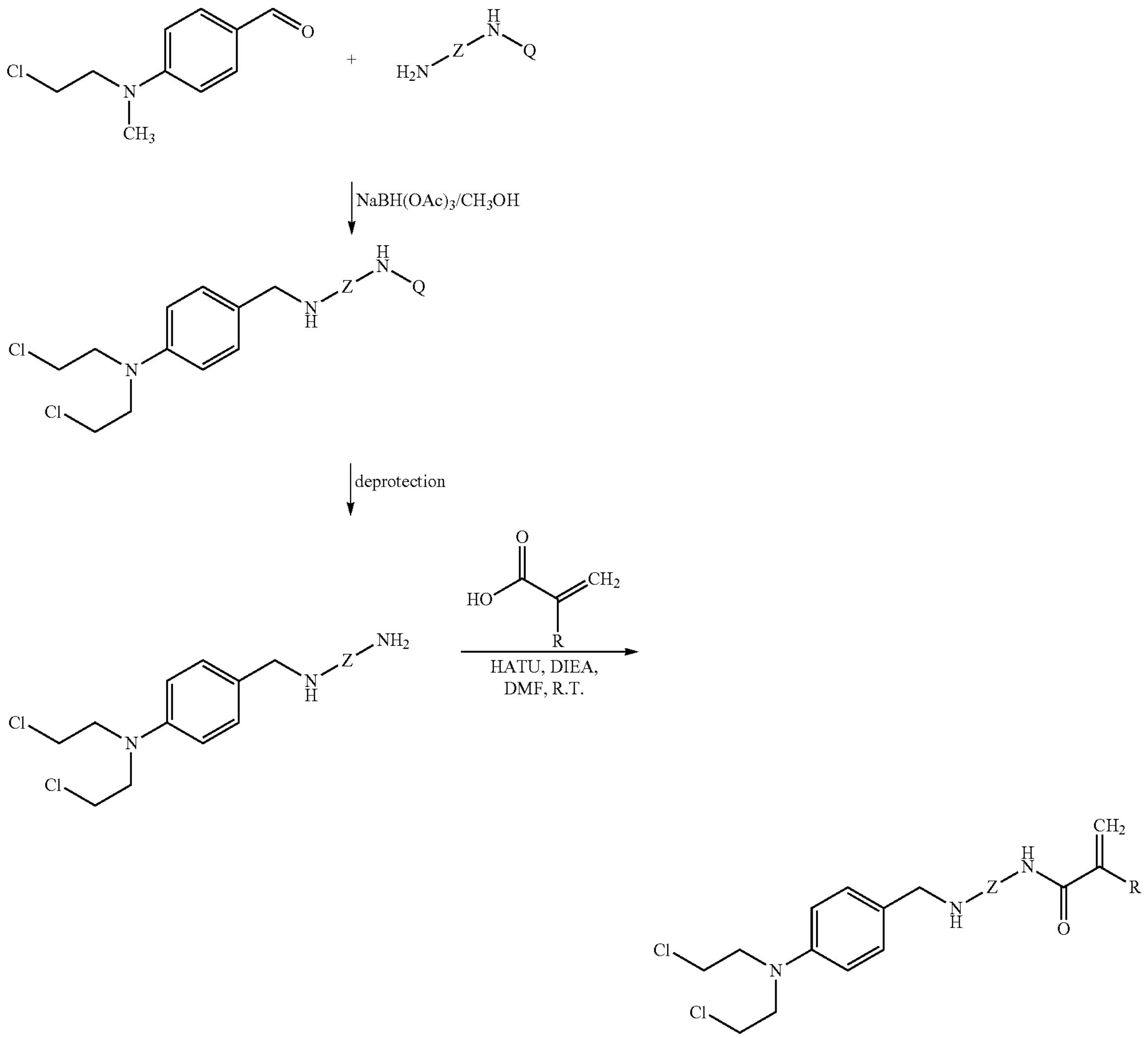

II B

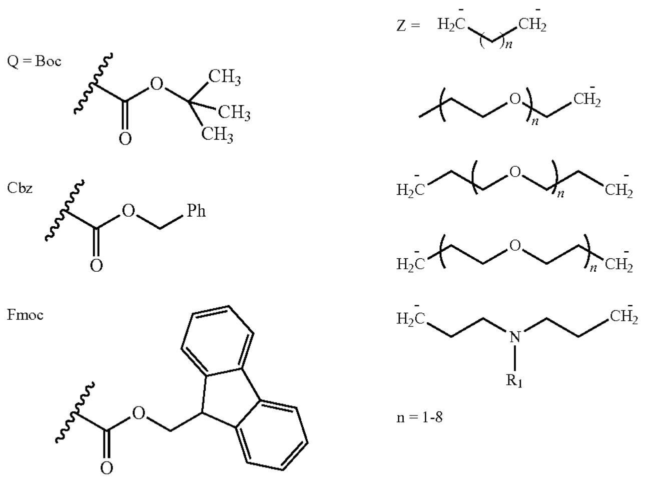

wherein Z and Q are as defined in the above scheme; R is selected from hydrogen, deuterium, halo, —CN, —$NO_2$, and an optionally substituted aliphatic, alicyclic, heteroaliphatic, heterocyclic, aromatic, acyl or heteroaromatic group; and R1 is H, alkyl, acyl or allyl.

In one aspect, a method is provided for preparing a compound of Formula IIB by:

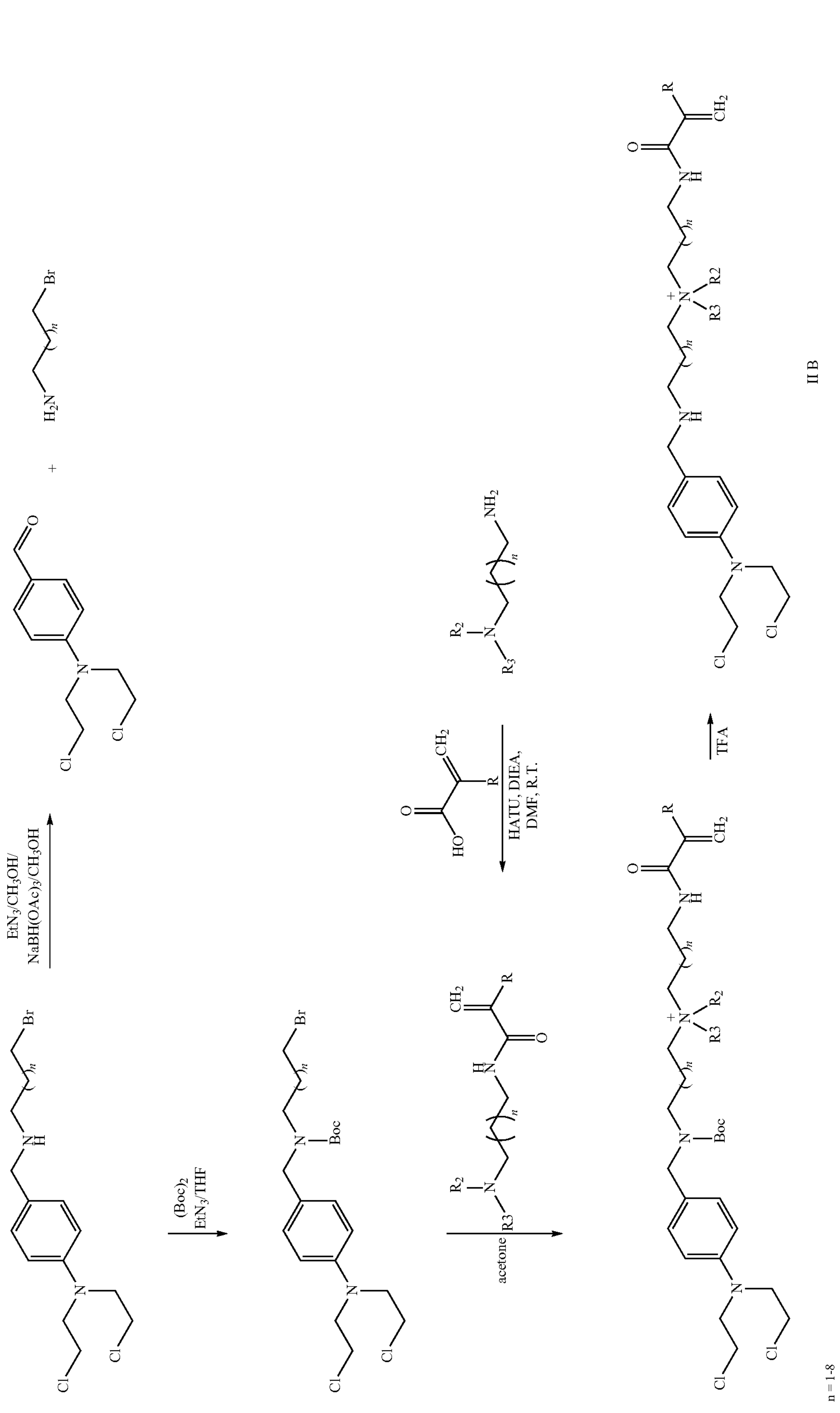
II B wherein each occurrence of n is independently 1-8; R is selected from hydrogen, deuterium, halo, —CN, —$NO_2$, and an optionally substituted aliphatic, alicyclic, heteroaliphatic, heterocyclic, aromatic, acyl or heteroaromatic group; and R2 and R3 are independently H, alkyl, acyl or allyl.
In one aspect, a method is provided for preparing a compound of Formula IIIA by:
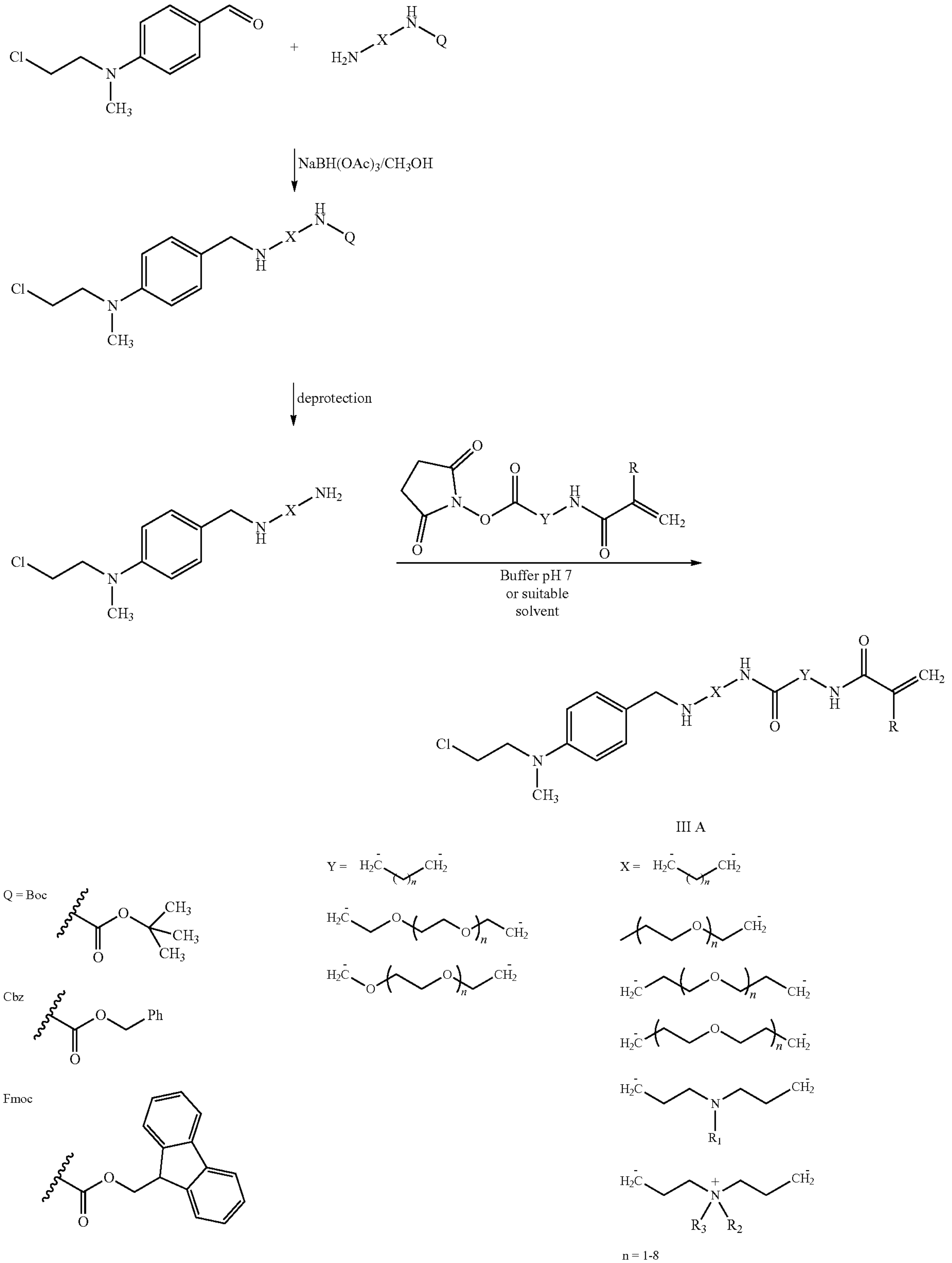
III A wherein X, Q, Y and n are as defined above and each occurrence of n is independently 1-8; R is selected from hydrogen, deuterium, halo, —CN, —$NO_2$, and an optionally substituted aliphatic, alicyclic, heteroaliphatic, heterocyclic, aromatic, acyl or heteroaromatic group; and each occurrence of R1, R2 and R3 are independently selected from H, alkyl, acyl and allyl.

In one aspect, a method is provided for preparing a compound of Formula IIIB by:

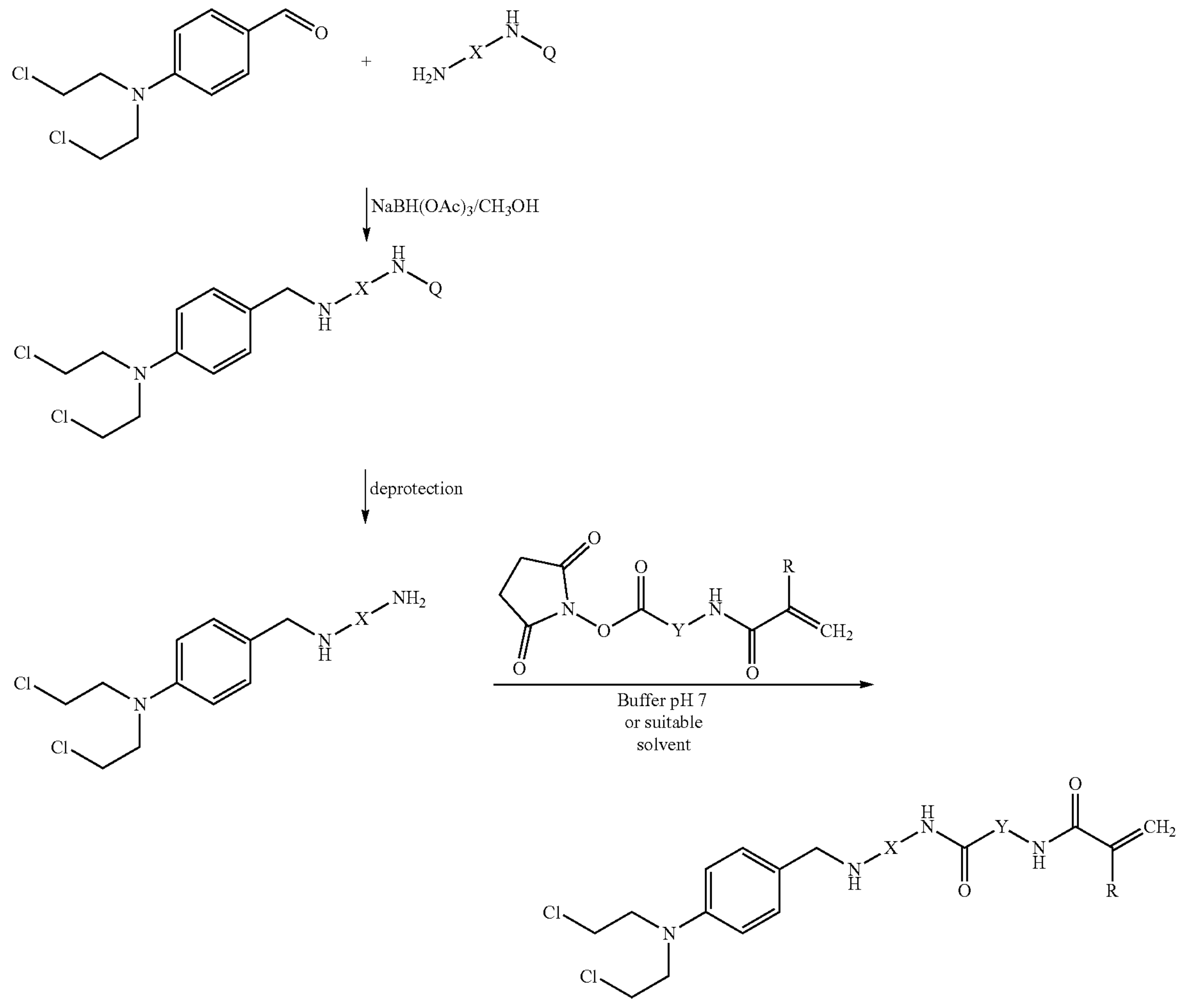

III B

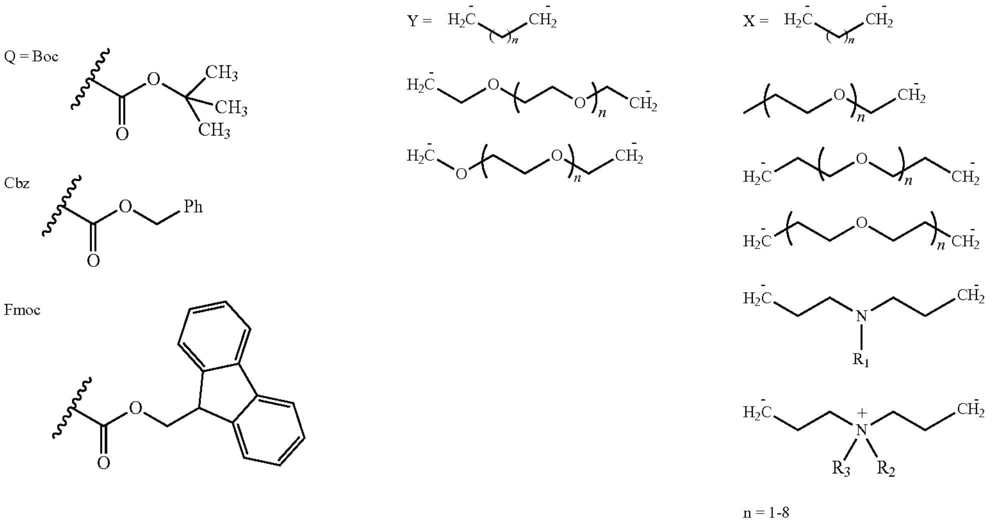

Q = Boc

Cbz

Fmoc

Y =

X = n = 1-8 wherein X, Q, Y and n are as defined above and each occurrence of n is independently 1-8; R is selected from hydrogen, deuterium, halo, —CN, —$NO_2$, and an optionally substituted aliphatic, alicyclic, heteroaliphatic, heterocyclic, aromatic, acyl or heteroaromatic group; and R1, R2 and R3 are independently H, alkyl, acyl or allyl.

In some embodiments of any of the foregoing methods, a protective group on Q other than Fmoc, Cbz or Boc is used.

In one aspect, a method is provided for the retention and imaging of proteins of a sample of interest comprising the steps of:

(a) conjugating proteins within the sample with a bifunctional crosslinker of Formula (I), wherein the bifunctional crosslinker comprises a protein-reactive chemical group and a gel-reactive chemical group;
(b) embedding the sample in a swellable material wherein proteins within the sample are anchored to the swellable material;
(c) subjecting the sample to digestion;
(d) swelling the swellable material to form an expanded sample;
(e) staining the sample either before or after steps (a) (b), (c), or (d); and
(f) imaging the expanded sample In some embodiments, the compound of Formula (I) is any one of compounds I-1 to I-10 as disclosed herein.

In some embodiments, the sample is a formalin-fixed, paraffin-embedded (FFPE) sample such as a tissue section.

In one aspect, a method is provided for labeling a nucleic acid in a biological sample comprising:

(a) contacting the sample with a compound of any one of Formulas (IIA), (IIB), (IIIA) or (IIIB) under conditions wherein the gel binding moiety operably links to RNA in the sample;
(b) contacting the sample with a solution comprising monomers of a polyelectrolyte gel;
(c) by free radical polymerization, polymerizing said monomers to form the polyelectrolyte gel and covalently conjugating the gel binding moiety to the polyelectrolyte gel;
(d) proteolytically digesting said sample; and
(e) dialyzing said sample to expand said polyelectrolyte gel.
(f) staining the sample either before or after steps (a) (b), (c), or (d); and
(g) imaging the expanded sample.

In some embodiments, a compound of Formula (IIA) is compound IIA-1 through IIA-6. In some embodiments, a compound of Formula (IIB) is compound IIB-1 through IIB-6. In some embodiments, a compound of Formula (IIIA) is compound IIIA-1 through IIIA-20. In some embodiments, a compound of Formula (IIIB) is compound IIIB-1 through IIIB-20.

In some embodiments, the sample is a formalin-fixed, paraffin-embedded (FFPE) sample such as a tissue section.

In some embodiments, the nucleic acid is RNA, DNA, mRNA, miRNA or ncRNA.

In one aspect, a method is provided for labeling protein and nucleic acid in a biological sample comprising:

(a) conjugating proteins within the sample with a bifunctional crosslinker of Formula (I), under conditions wherein the gel binding moiety operably links to proteins in the sample;
(b) contacting the sample with a compound of any one of Formulas (IIA), (IIB), (IIIA) or (IIIB) under conditions wherein the gel binding moiety operably links to nucleic acid in the sample;
(c) contacting the sample with a solution comprising monomers of a polyelectrolyte gel;
(d) by free radical polymerization, polymerizing said monomers to form the polyelectrolyte gel and covalently conjugating the gel binding moiety to the polyelectrolyte gel;
(e) proteolytically digesting said sample; and
(f) dialyzing said sample to expand said polyelectrolyte gel.
(g) staining the sample either before or after steps (a) (b), (c), or (d); and
(h) imaging the expanded sample.

In some embodiments, step (b) is performed before step (a). In some embodiments, step (a) and step (b) are performed concurrently. In some embodiments, a wash step in performed after step (a), after step (b), or both. In some embodiments, when steps (a) and (b) are performed concurrently, a wash step follows.

In some embodiments, a compound of Formula (I) is compound I-1 through I-10. In some embodiments, a compound of Formula (IIA) is compound IIA-1 through IIA-6. In some embodiments, a compound of Formula (IIB) is compound IIB-1 through IIB-6. In some embodiments, a compound of Formula (IIIA) is compound IIIA-1 through IIIA-20. In some embodiments, a compound of Formula (IIIB) is compound IIIB-1 through IIIB-20.

In some embodiments, the sample is a formalin-fixed, paraffin-embedded (FFPE) sample such as a tissue section.

In some embodiments, the nucleic acid is RNA, DNA, mRNA, miRNA or ncRNA.

In some embodiments, an in situ hybridization technique is performed to identify nucleic acids of interest in the sample.

In some embodiments of the foregoing methods, a plurality of initiator deoxyribonucleic acid (DNA) probes targeting a plurality of RNA targets of interest are provided, wherein each of the plurality of initiator DNA probes comprise (A) a sequence complementary to a sequence from one of the RNA targets of interest, and (B) a hybridization chain reaction (HCR) initiator sequence;

(a) contacting the sample with the plurality of initiator DNA probes under conditions wherein the sequence complementary to the sequence from one of the RNA targets of interest hybridizes to that sequence from the RNA target of interest;
(b) for each initiator DNA probe, providing a pair of fluorophore-labeled DNA hairpins that metastably coexist in the absence of the initiator DNA probe; and
(c) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe.

In some embodiments, the prior method further comprising the step of washing the sample to remove unhybridized initiator DNA probes and fluorophore-labeled DNA hairpins that have not been incorporated into fluorescent amplification polymers.

In some embodiments, the prior methods further comprise, after expanding the polyacrylamide gel, the step of embedding the expanded sample in a polyacrylamide gel matrix.

In some embodiments, the prior methods further comprise, prior to step (f), obtaining an image of the expanded sample.

In some embodiments of the prior methods, the image is obtained by confocal microscopy.

In some embodiments of the prior methods, the plurality of RNA targets of interest comprise mRNA.

In some embodiments of the prior methods, one or more of the fluorophore-labeled DNA hairpins are labeled with a fluorophore selected from the group consisting of fluorescein isothiocyanate (FITC), tetramethylrhodamine (TRITC), 4',6-diamidino-2-phenylindole (DAPI), cyanine dye 5 (Cy5), Alexa 488, Alexa 514, Alexa 546, Alexa 594, and Alexa 647.

In some embodiments of the prior methods, for each pair of fluorophore-labeled DNA hairpins both hairpins are labeled with the same fluorophore.

In some embodiments of the prior methods, the initiator DNA probes are between 56-60 nucleotides in length.

In some embodiments of the prior methods, the monomer solution comprises sodium acrylate, acrylamide, and N—N'-methylenebisacrylamide.

In some embodiments of the prior methods, the free radical polymerization is induced with ammonium persulfate (APS) initiator and tetramethylethylenediamine (TEMED).

In some embodiments of the prior methods, the biological sample is chemically fixed and permeabilized prior to step (a).

In some embodiments of the prior methods, dialyzing said sample to expand said polyelectrolyte gel comprises dialyzing said sample in water to expand said polyelectrolyte gel.

In some embodiments of the prior methods, the biological sample is derived from a vertebrate.

In some embodiments of the prior methods, the vertebrate is a mammal,

In some embodiments of the prior methods, the mammal is a human.

In some embodiments of the prior methods, the biological sample is a brain, heart, lung, gastrointestinal, circulatory, kidney, urogenital, pancreatic, gall bladder, muscle, breast, glandular, or bone sample.

In some embodiments of the prior methods, the method further comprises repeating the method for a plurality of biological samples.

In some embodiments of the prior methods, the plurality of biological samples are in an array or in a microarray.

In some embodiments of the prior methods, the array comprises a multiwell plate with each of said plurality of biological samples in a separate well of said multiwell plate.

In some embodiments of the prior methods, the plurality of biological samples comprises serial sections from a single organism.

In some embodiments, the prior methods further comprise, prior to step (a) or step (b), or prior to a concurrent steps (a) and (b), the steps:

- contacting the sample with at least one primary antibody under conditions where it selectively recognizes a target protein of interest; and
- contacting the sample with at least one secondary antibody operably linked to a detectable label.

Other features and advantages of this disclosure will become apparent from the following detailed description examples and figures. It should be understood, however, that the detailed description and the specific examples while indicating preferred embodiments disclosed herein are given by way of illustration only, since various changes and modifications within the spirit and scope of the disclosure will become apparent to those skilled in the art from this detailed description.

DETAILED DESCRIPTION

Definitions

The term "aliphatic", as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, or alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. "Lower alkenyl" and "lower alkynyl" respectively include corresponding 1-6 carbon moieties.

In certain embodiments, the alkyl, alkenyl and alkynyl groups employed in the disclosure contain 1-20; 2-20; 3-20; 4-20; 5-20; 6-20; 7-20 or 8-20 aliphatic carbon atoms. In certain other embodiments, the alkyl, alkenyl, and alkynyl groups employed in the disclosure contain 1-10; 2-10; 3-10; 4-10; 5-10; 6-10; 7-10 or 8-10 aliphatic carbon atoms. In yet other embodiments, the alkyl, alkenyl, and alkynyl groups employed in the disclosure contain 1-8; 2-8; 3-8; 4-8; 5-8; 6-20 or 7-8 aliphatic carbon atoms. In still other embodiments, the alkyl, alkenyl, and alkynyl groups employed in the disclosure contain 1-6; 2-6; 3-6; 4-6 or 5-6 aliphatic carbon atoms. In yet other embodiments, the alkyl, alkenyl, and alkynyl groups employed in the disclosure contain 1-4; 2-4 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to monocyclic, or polycyclic aliphatic hydrocarbons and bridged cycloalkyl compounds, which are optionally substituted with one or more functional groups. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl, cyclohexyl, —$CH_2$-cyclohexyl, cyclohexenylethyl, cyclohexanylethyl, norborbyl moieties and the like, which again, may bear one or more substituents.

The term "alkoxy", "alkoxyl", "alkyloxy", or "alkyloxyl", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the disclosure contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

Some examples of substituents of the above-described aliphatic (and other) moieties of compounds of the disclosure include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(=O)$R_x$; —$CO_2(R_x)$; —C(=O)N$(R_x)_2$; —OC(=O)$R_x$; —$OCO_2R_x$; —OC(=O)N$(R_x)_2$; —N$(R_x)_2$; —$OR_x$; —$SR_x$; —S(O)$R_x$; —S$(O)_2R_x$; —$NR_x$(CO)$R_x$; —N$(R_x)CO_2R_x$; —N$(R_x)S(O)_2R_x$; —N$(R_x)$C(=O)N$(R_x)_2$; —S$(O)_2N(R_x)_2$; wherein each occurrence of $R_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

In general, the term "aromatic" or "aromatic moiety", as used herein, refers to a stable mono- or polycyclic, unsaturated moiety having preferably 3-14 carbon atoms, each of which may be substituted or unsubstituted. In certain embodiments, the term "aromatic moiety" refers to a planar ring having p-orbitals perpendicular to the plane of the ring at each ring atom and satisfying the Huckel rule where the number of pi electrons in the ring is (4n+2) wherein n is an integer. A mono- or polycyclic, unsaturated moiety that does not satisfy one or all of these criteria for aromaticity is defined herein as "non-aromatic", and is encompassed by the term "alicyclic".

In general, the term "heteroaromatic" or "heteroaromatic moiety", as used herein, refers to a stable mono- or polycyclic, unsaturated moiety having preferably 3-14 carbon atoms, each of which may be substituted or unsubstituted; and comprising at least one heteroatom selected from O, S and N within the ring (i.e., in place of a ring carbon atom). In certain embodiments, the term "heteroaromatic moiety" refers to a planar ring comprising at least one heteroatom, having p-orbitals perpendicular to the plane of the ring at each ring atom, and satisfying the Hückel's rule where the number of pi electrons in the ring is (4n+2) wherein n is an integer.

It will also be appreciated that aromatic and heteroaromatic moieties, as defined herein may be attached via an alkyl or heteroalkyl moiety and thus also include-(alkyl) aromatic, -(heteroalkyl) aromatic, -(heteroalkyl) heteroaromatic, and -(heteroalkyl) heteroaromatic moieties. Thus, as used herein, the phrases "aromatic or heteroaromatic moieties" and "aromatic, heteroaromatic, -(alkyl) aromatic, -(heteroalkyl) aromatic, -(heteroalkyl) heteroaromatic, and -(heteroalkyl) heteroaromatic" are interchangeable. Substituents include, but are not limited to, any of the previously mentioned substituents, i.e., the substituents recited for aliphatic moieties, or for other moieties as disclosed herein, resulting in the formation of a stable compound.

The term "aryl", as used herein, does not differ significantly from the common meaning of the term in the art, and refers to an unsaturated cyclic moiety comprising at least one aromatic ring. In certain embodiments, "aryl" refers to a mono- or bicyclic carbocyclic ring system having one or two aromatic rings including, but not limited to phenyl, naphthyl, tetrahydronaphthyl, indanyl, indenyl and the like.

The term "heteroaryl", as used herein, does not differ significantly from the common meaning of the term in the art, and refers to a cyclic aromatic radical having from five to twelve ring atoms of which one ring atom is selected from S, O and N; zero, one, two, three, four, or five ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, quinolinyl, isoquinolinyl, and the like.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(=O)$R_x$; —$CO_2(R_x)$; —C(=O)N$(R_x)_2$; —OC(=O)$R_x$; —$OCO_2R_x$; —OC(=O)N$(R_x)_2$; —N$(R_x)_2$; —$OR_x$; —$SR_x$; —S(O)$R_x$; —S$(O)_2R_x$; —$NR_x$(CO)$R_x$; —N$(R_x)CO_2R_x$; —N$(R_x)S(O)_2R_x$; —N$(R_x)$C(=O)N$(R_x)_2$; —S$(O)_2N(R_x)_2$; wherein each occurrence of $R_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl) aryl or -(alkyl) heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments shown in the Examples that are described herein.

The term "cycloalkyl", as used herein, refers specifically to groups having three to twelve, preferably three to ten carbon atoms. Suitable cycloalkyls include, but are not limited to cyclopropyl, cyclobutyl, cyclopentyl, cyclohexyl, cycloheptyl and the like, which, as in the case of aliphatic, alicyclic, heteroaliphatic or heterocyclic moieties, may optionally be substituted with substituents including, but not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(=O)$R_x$; —$CO_2(R_x)$; —C(=O)N$(R_x)_2$; —OC(=O)$R_x$; —$OCO_2R_x$; —OC(=O)N$(R_x)_2$; —N$(R_x)_2$; —$OR_x$; —$SR_x$; —S(O)$R_x$; —S$(O)_2R_x$; —$NR_x$(CO)$R_x$; —N$(R_x)CO_2R_x$; —N$(R_x)$S$(O)_2R_x$; —N$(R_x)$C(=O)N$(R_x)_2$; —S$(O)_2$N$(R_x)_2$; wherein each occurrence of $R_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heteroaliphatic", as used herein, refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be linear or branched, and saturated or unsaturated. In certain embodiments, heteroaliphatic moieties are substituted by independent replacement of one or more of the hydrogen atoms thereon with one or more moieties including, but not limited to aliphatic; alicyclic; heteroaliphatic; heterocyclic; aromatic; heteroaromatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(=O)$R_x$; —$CO_2(R_x)$; —C(=O)N$(R_x)_2$; —OC(=O)$R_x$; —$OCO_2R_x$; —OC(=O)N$(R_x)_2$; —N$(R_x)_2$; —$OR_x$; —$SR_x$; —S(O)$R_x$; —S$(O)_2R_x$; —$NR_x$(CO)$R_x$; —N$(R_x)CO_2R_x$; —N$(R_x)$S$(O)_2R_x$; —N$(R_x)$C(=O)N$(R_x)_2$; —S$(O)_2$N$(R_x)_2$; wherein each occurrence of $R_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples of generally applicable substituents are illustrated by the specific embodiments shown in the Examples that are described herein.

The term "heterocycloalkyl", "heterocycle" or "heterocyclic", as used herein, refers to compounds which combine the properties of heteroaliphatic and cyclic compounds and include, but are not limited to, saturated, unsaturated and partially saturated mono- or polycyclic cyclic ring systems having 5-16 atoms wherein at least one ring atom is a heteroatom selected from O, S and N (wherein the nitrogen and sulfur heteroatoms may be optionally oxidized), wherein the ring systems are optionally substituted with one or more functional groups, as defined herein. In certain embodiments, the term "heterocycloalkyl", "heterocycle" or "heterocyclic" refers to a non-aromatic or partially aromatic 5-12 membered ring or a polycyclic group wherein at least one ring atom is a heteroatom selected from O, S and N (wherein the nitrogen and sulfur heteroatoms may be optionally oxidized), including, but not limited to a bi- or tri-cyclic group, comprising fused rings having between one and four heteroatoms independently selected from O, S and N, wherein (i) each 5-membered ring has 0 to 2 double bonds, each 6-membered ring has 0 to 3 double bonds and each 7-membered ring has 0 to 3 double bonds, (ii) the nitrogen and sulfur heteroatoms may be optionally be oxidized, (iii) the nitrogen heteroatom may optionally be quaternized, and (iv) any of the above heterocyclic rings may be fused to an aryl or heteroaryl ring. Representative heterocycles include, but are not limited to, heterocycles such as furanyl, thiofuranyl, pyranyl, pyrrolyl, pyrazolyl, imidazolyl, thienyl, pyrrolidinyl, pyrazolinyl, pyrazolidinyl, imidazolinyl, imidazolidinyl, piperidinyl, piperazinyl, oxazolyl, oxazolidinyl, isooxazolyl, isoxazolidinyl, dioxazolyl, thiadiazolyl, oxadiazolyl, tetrazolyl, triazolyl, thiatriazolyl, oxatriazolyl, thiadiazolyl, oxadiazolyl, morpholinyl, thiazolyl, thiazolidinyl, isothiazolyl, isothiazolidinyl, dithiazolyl, dithiazolidinyl, tetrahydrofuryl, and benzofused derivatives thereof. In certain embodiments, a "substituted heterocycle, or heterocycloalkyl or heterocyclic" group is utilized and as used herein, refers to a heterocycle, or heterocycloalkyl or heterocyclic group, as defined above, substituted by the independent replacement of one, two or three of the hydrogen atoms thereon with but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(=O)$R_x$; —$CO_2(R_x)$; —C(=O)N$(R_x)_2$; —OC(=O)$R_x$; —$OCO_2R_x$; —OC(=O)N$(R_x)_2$; —N$(R_x)_2$; —$OR_x$; —$SR_x$; —S(O)$R_x$; —S$(O)_2R_x$; —$NR_x$(CO)$R_x$; —N$(R_x)CO_2R_x$; —N$(R_x)$S$(O)_2R_x$; —N$(R_x)$C(=O)N$(R_x)_2$; —S$(O)_2$N$(R_x)_2$; wherein each occurrence of $R_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl or heteroaryl substituents described above and herein may be substituted or unsubstituted. Additional examples or generally applicable substituents are illustrated by the specific embodiments shown in the Examples, which are described herein.

Additionally, it will be appreciated that any of the alicyclic or heterocyclic moieties described above and herein may comprise an aryl or heteroaryl moiety fused thereto. Additional examples of generally applicable substituents are illustrated by the specific embodiments shown in the Examples that are described herein.

The terms "halo" and "halogen" as used herein refer to an atom selected from fluorine, chlorine, bromine and iodine.

The term "amino", as used herein, refers to a primary (—$NH_2$), secondary (—$NHR_x$), tertiary (—$NR_xR_y$) or quaternary (—N+$R_xR_yR_z$) amine, where $R_x$, $R_y$ and $R_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "acyl", as used herein, refers to a group having the general formula-C(═O)R, where R is an aliphatic, alicyclic, heteroaliphatic, heterocyclic, aromatic or heteroaromatic moiety, as defined herein. Non-limiting examples of acyl groups include formyl (methanoyl), acetyl (ethanoyl), propanoyl, butanoyl, propenoyl (acryloyl), butenoyl (crotonyl) and the like.

As used herein, the terms "aliphatic", "heteroaliphatic", "alkyl", "alkenyl", "alkynyl", "heteroalkyl", "heteroalkenyl", "heteroalkynyl", and the like encompass substituted and unsubstituted, saturated and unsaturated, and linear and branched groups. Similarly, the terms "alicyclic", "heterocyclic", "heterocycloalkyl", "heterocycle" and the like encompass substituted and unsubstituted, and saturated and unsaturated groups. Additionally, the terms "cycloalkyl", "cycloalkenyl", "cycloalkynyl", "heterocycloalkyl", "heterocycloalkenyl", "heterocycloalkynyl", "aromatic", "heteroaromatic", "aryl", "heteroaryl" and the like encompass both substituted and unsubstituted groups.

By the term "protecting group", "protection group" or "protective group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, as detailed herein, certain exemplary oxygen protecting groups are utilized. These oxygen protecting groups include, but are not limited to methyl ethers, substituted methyl ethers (e.g., MOM (methoxymethyl ether), MTM (methylthiomethyl ether), BOM (benzyloxymethyl ether), PMBM or MPM (p-methoxybenzyloxymethyl ether), to name a few), substituted ethyl ethers, substituted benzyl ethers, silyl ethers (e.g., TMS (trimethylsilyl ether), TES (triethylsilyl ether), TIPS (triisopropylsilyl ether), TBDMS (t-butyldimethylsilyl ether), tribenzyl silyl ether, TBDPS (t-butyldiphenyl silyl ether), to name a few), esters (e.g., formate, acetate, benzoate (Bz), trifluoroacetate, dichloroacetate, to name a few), carbonates, cyclic acetals and ketals. In certain other exemplary embodiments, nitrogen protecting groups are utilized. These nitrogen protecting groups include, but are not limited to, carbamates (including methyl, ethyl and substituted ethyl carbamates (e.g., Troc), to name a few) amides, cyclic imide derivatives, N-Alkyl and N-Aryl amines, imine derivatives, and enamine derivatives, to name a few. Others include fluorenylmethoxycarbonyl (Fmoc), carboxybenzyl (Cbz; benzyloxycarbonyl) and t-butyloxycarbonyl (Boc). Certain other exemplary protecting groups are detailed herein, however, it will be appreciated that the present disclosure is not intended to be limited to these protecting groups; rather, a variety of additional equivalent protecting groups can be readily identified using the above criteria and utilized in the present disclosure. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

Expansion Microscopy is described in the following publications, patent applications and patents, each of which is incorporated by reference herein in its entirety: Ser. No. 15/592,221; US2018-0052081; US-2021-0215580-A1; WO2019/075091; US2020-0239946; WO2019/103996; WO/2020/142490; U.S. Pat. No. 10,309,879B2; WO15/127183; U.S. Pat. No. 10,309,879B2; WO15/127183; US 2016-0305856; U.S. Pat. Nos. 10,059,990; 10,563,257; US-20-0055597-A1; U.S. Pat. Nos. 10,526,649; 1,036,445; WO 2017/027367; U.S. Pat. No. 10,317,321; WO 2017/027368; WO/2017/147435; U.S. Pat. No. 10,995,361; WO/2018/136856; WO/2018/157048; WO/2018/157074; US-2020-0041514-A1; WO19/023214; US20190032128A1; Chen et al., Science. 2015 Jan. 30; 347 (6221): 543-8. doi: 10.1126/science.1260088. Epub 2015 Jan. 15; Alon et al., bioRxiv doi.org/10.1101/2020.05.13.094268.

In aspects of this disclosure, new reagents are described for cross-linking to protein or nucleic acids, and for incorporation into a polyacrylamide or other gel for procedures involving expansion microscopy, by way of a non-limiting example.

In one embodiment, compound are described herein of Formula (I)

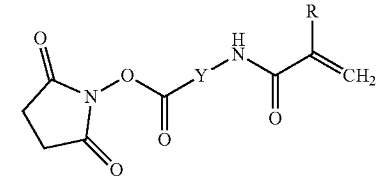

(I)

wherein Y is selected from among:

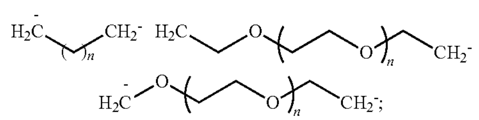

n is 1, 2, 3, 4, 5, 6, 7 or 8; and

R is selected from hydrogen, deuterium, halo, —CN, $—NO_2$, and an optionally substituted aliphatic, alicyclic, heteroaliphatic, heterocyclic, aromatic, acyl or heteroaromatic group.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl. In some embodiments, R is formyl (methanoyl), acetyl (ethanoyl), propanoyl, butanoyl, propenoyl (acryloyl), or butenoyl (crotonyl).

In some embodiments, acyl is formyl or acetyl.

Non-limiting examples of optional substitutions of R include hydrogen, deuterium, halo, —CN, $—NO_2$, aliphatic, alicyclic, heteroaliphatic, heterocyclic, aromatic, heteroaromatic, $—OR^{aa}$, $—NR^{bb}R^{cc}$, $—S(═O)_wR^{dd}$, $—S(═O)_wN$-

$R^{ee}R^{ff}$, $—C(=O)R^{gg}$, $—CO_2R^{hh}$, $—CONR^{ii}R^{jj}$, $—NR^{kk}CONR^{ll}R^{mm}$, $—OCONR^{nn}R^{oo}$, or $—NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, $—NO_2$, —OH, $—CH_2F$, $—CHF_2$, $—CF_3$, $—OCH_3$, $—OCH_2F$, $—OCHF_2$, $—OCF_3$, $—NH_2$, $—NHCH_3$, $—N(CH_3)_2$, $—CO_2H$, —SH, $—S(O)_wCH_3$, or an aliphatic, alicyclic, heteroaliphatic, heterocyclic, aromatic, or heteroaromatic; and w is 0, 1, or 2.

Non-limiting examples of compounds of Formula (I) include:

I-1

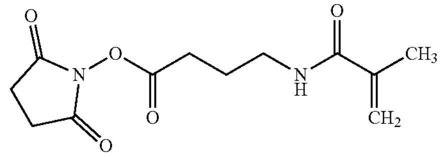

I-2

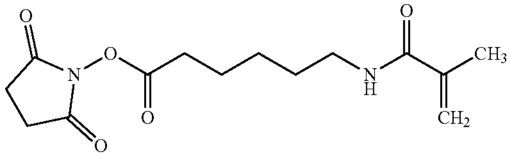

I-3

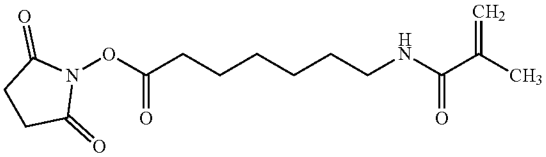

I-4

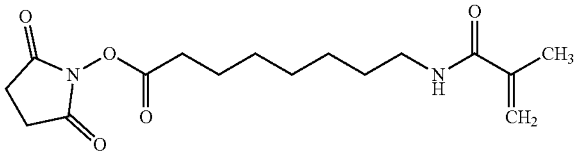

I-5

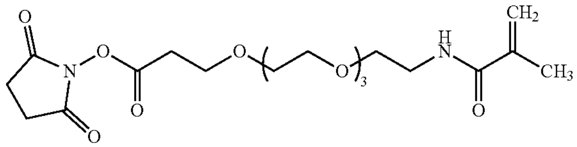

I-6

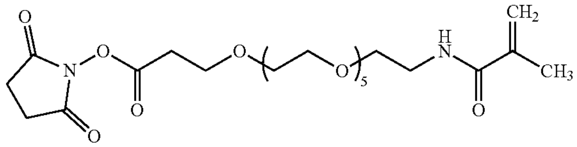

I-7

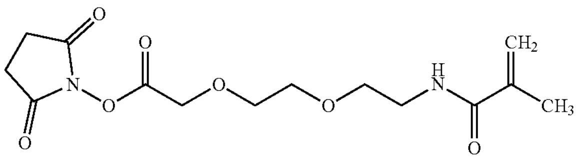

-continued

I-8

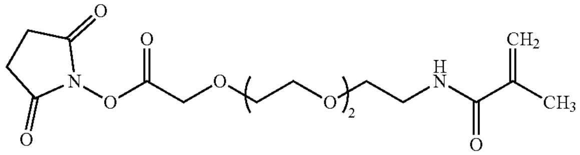

I-9

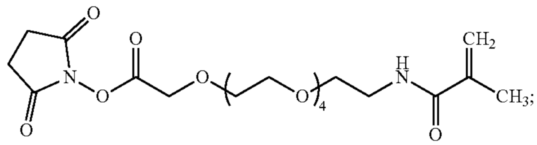

and 1-10

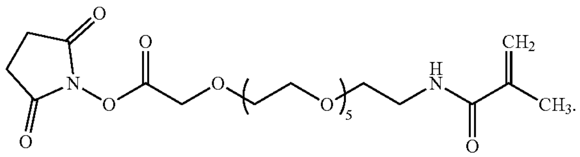

In some embodiments, a compounds is provided having Formula (IIA) or (IIB):

(IIA)

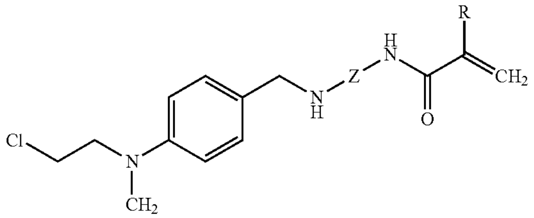

(IIB)

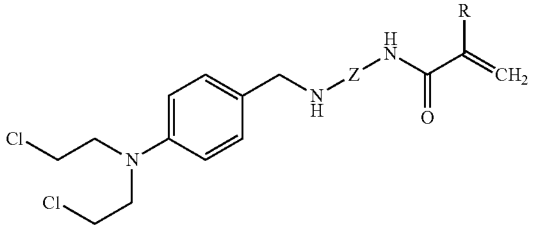

wherein Z is selected from among:

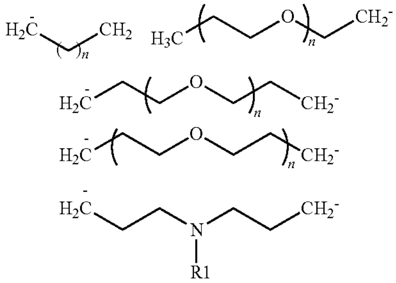

-continued

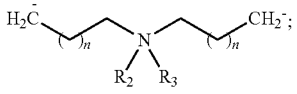

each occurrence of n is independently 1, 2, 3, 4, 5, 6, 7 or 8;

R is selected from hydrogen, deuterium, halo, —CN, —$NO_2$, and an optionally substituted aliphatic, alicyclic, heteroaliphatic, heterocyclic, aromatic, acyl or heteroaromatic group; and R1, R2 and R3 are independently H, alkyl, acyl or allyl.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

Non-limiting examples of optional substitutions of R include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

In some embodiments, R1, R2 or R3 is H. In some embodiments, R1, R2 or R3 is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R1, R2 or R3 is allyl. In some embodiments, R1, R2 or R3 is formyl (methanoyl), acetyl (ethanoyl), propanoyl, butanoyl, propenoyl (acryloyl), or butenoyl (crotonyl).

In some embodiments, acyl is formyl or acetyl.

In the Z moiety

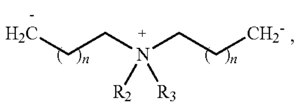

each n is independently selected from 1, 2, 3, 4, 5, 6, 7 or 8; and $R^2$ and $R^3$ are independently selected as described above.

Non-limiting examples of compounds of Formula (IIA) include:

IIA-1

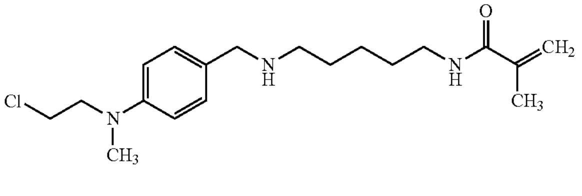

-continued

IIA-2

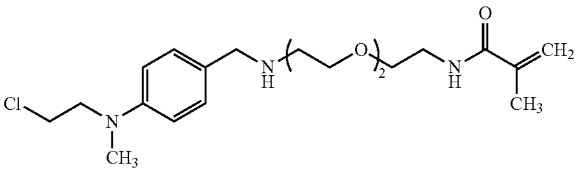

IIA-3

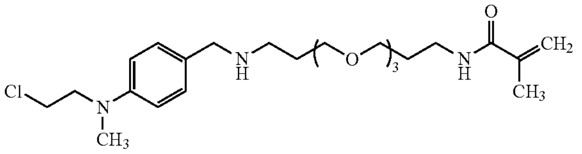

IIA-4

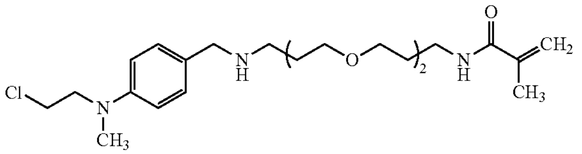

IIA-5

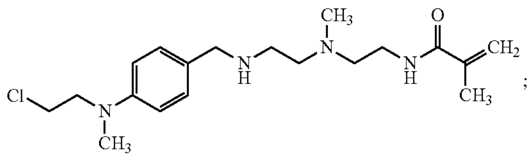

; and

IIA-6

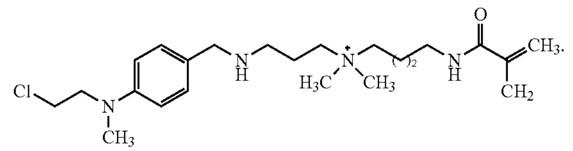

Non-limiting examples of compounds of Formula (IIB) include:

IIB-1

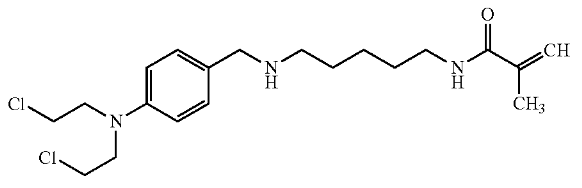

IIB-2

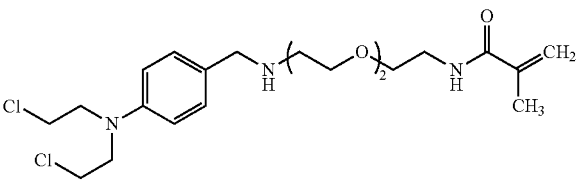

-continued

IIB-3

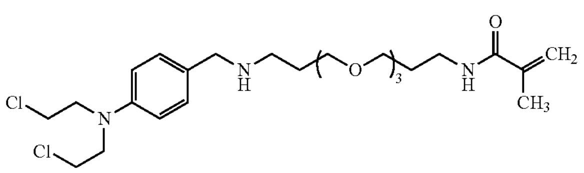

IIB-4

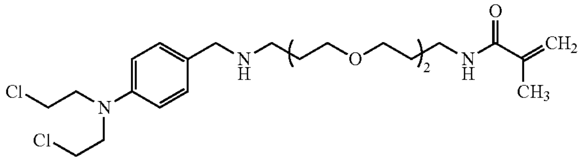

IIB-5

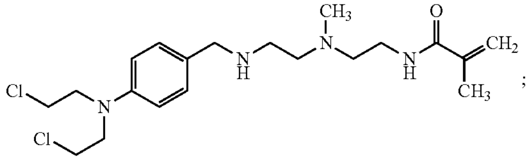

; and

IIB-6

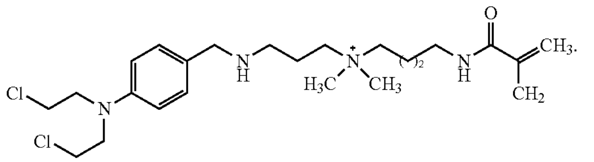

In some embodiments, a compound is provided having Formula (IIIA) or (IIIB):

(IIIA)

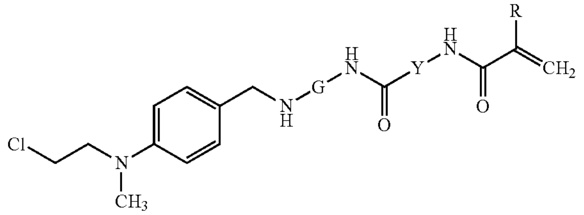

(IIIB)

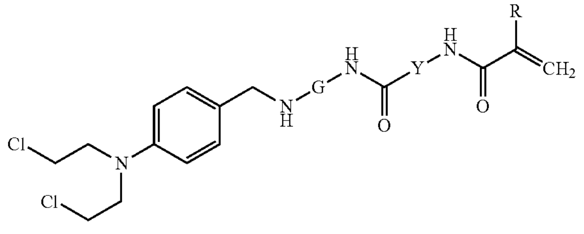

wherein G is selected from among:

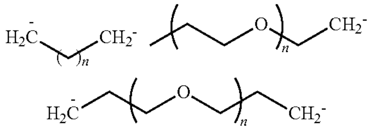

-continued

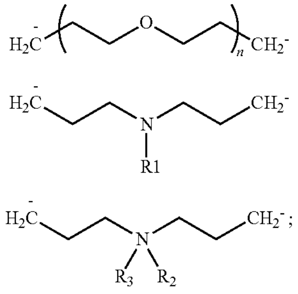

Y is selected from:

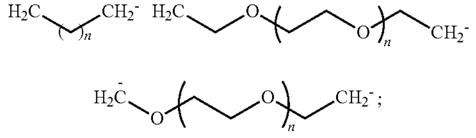

each occurrence of n is independently 1, 2, 3, 4, 5, 6, 7 or 8;

R is selected from hydrogen, deuterium, halo, —CN, —$NO_2$, and an optionally substituted aliphatic, alicyclic, heteroaliphatic, heterocyclic, aromatic, acyl or heteroaromatic group; and R1, R2 and R3 is independently H, alkyl, acyl or allyl.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

Non-limiting examples of optional substitutions of R include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

In some embodiments, R1, R2 or R3 is independently H. In some embodiments, R1, R2 or R3 is independently a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R1, R2 or R3 is allyl. In some embodiments, R1, R2 or R3 is formyl (methanoyl), acetyl (ethanoyl), propanoyl, butanoyl, propenoyl (acryloyl), or butenoyl (crotonyl).

In some embodiments, acyl is formyl or acetyl.

The n in the G moiety and the n in the Y moiety are each independently selected from 1, 2, 3, 4, 5, 6, 7 or 8.

Non-limiting examples of compounds of Formulas (IIIA) include:
IIIA-1
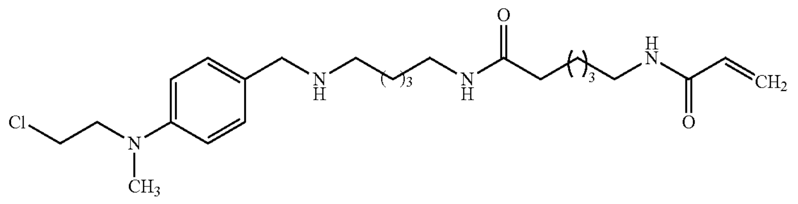
IIIA-2
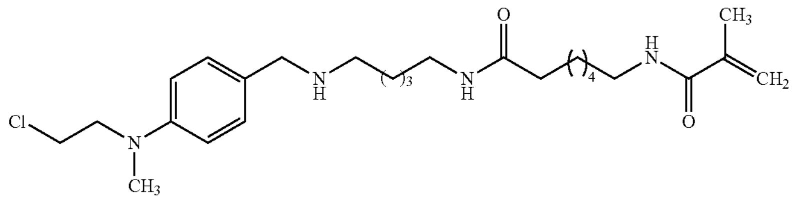
IIIA-3
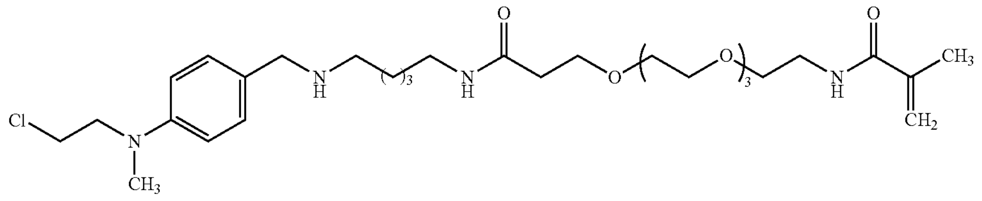
IIIA-4
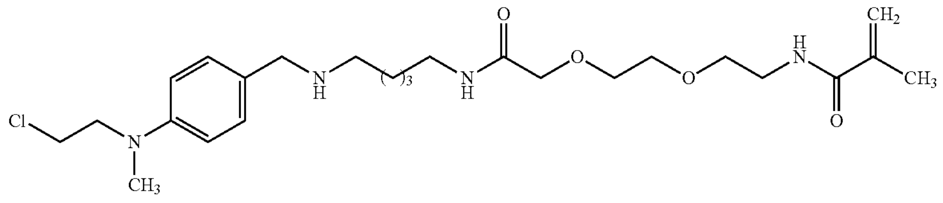
IIIA-5
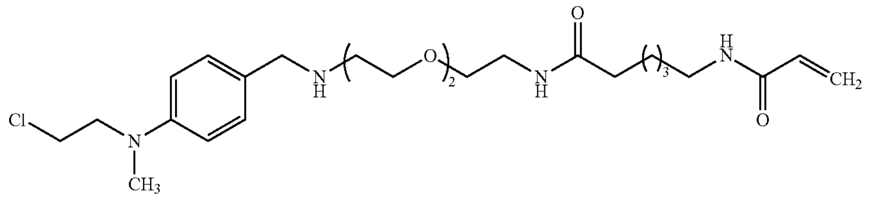
IIIA-6
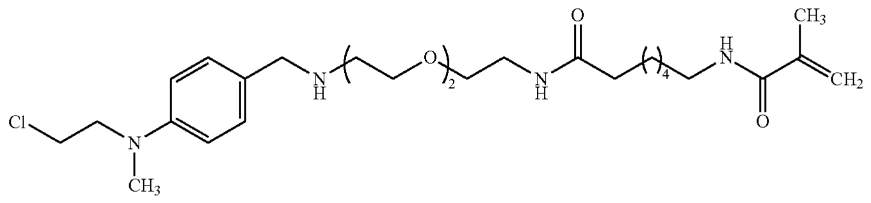
IIIA-7
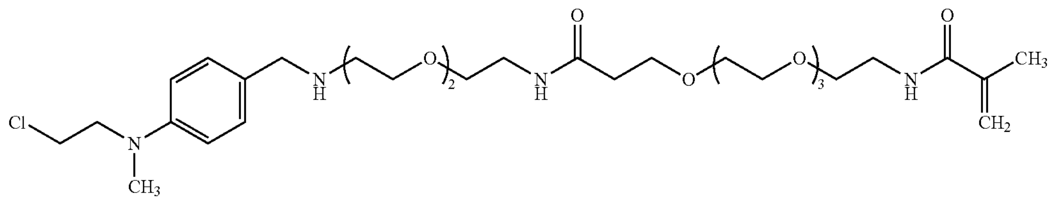

-continued
IIIA-8
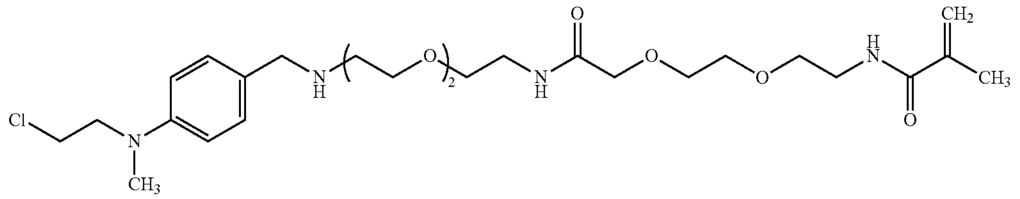
IIIA-9
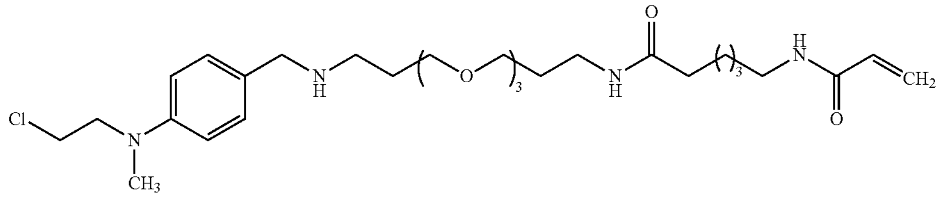
IIIA-10
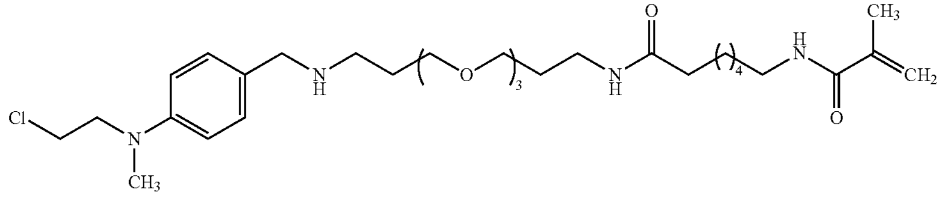
IIIA-11
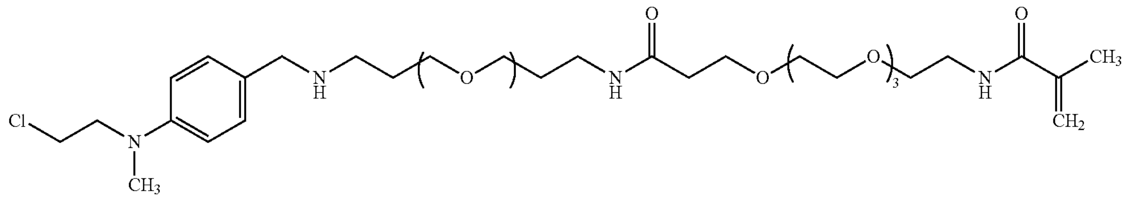
IIIA-12
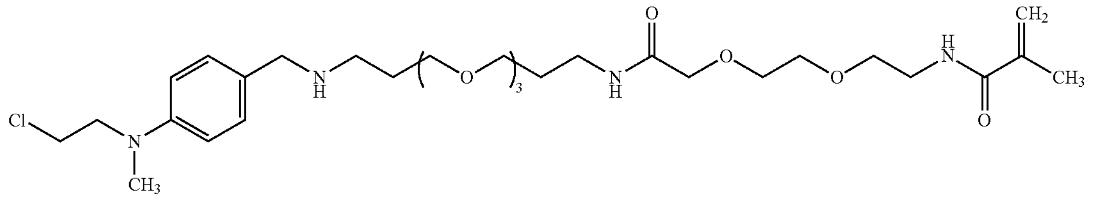
IIIA-13
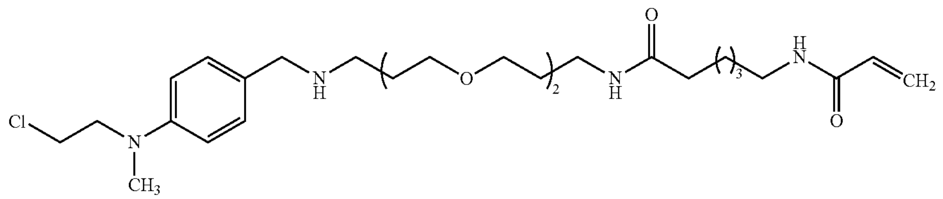
IIIA-14
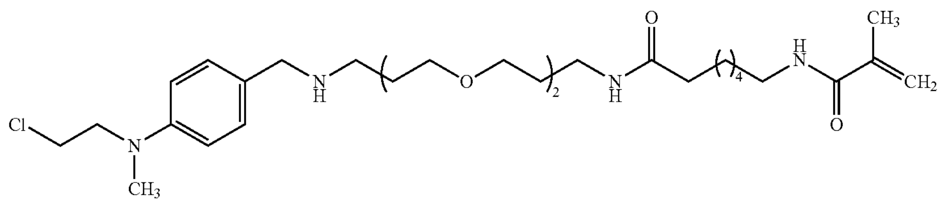

-continued
IIIA-15
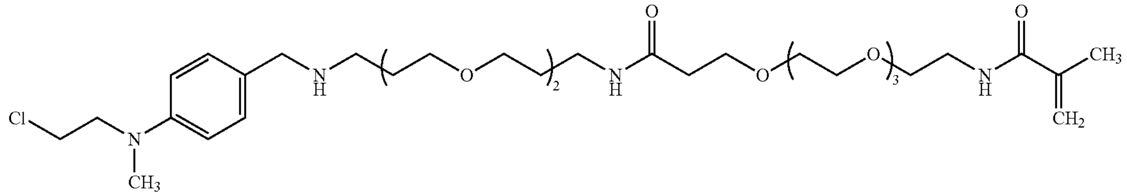
IIIA-16
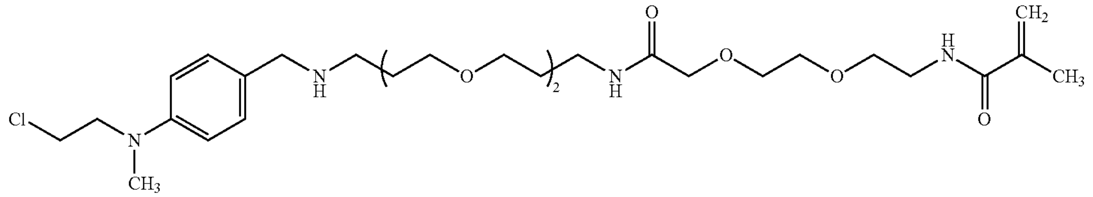
IIIA-17
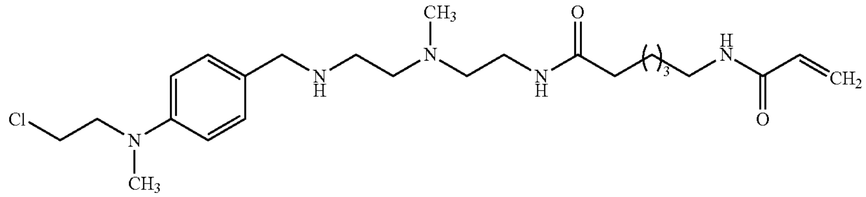
IIIA-18
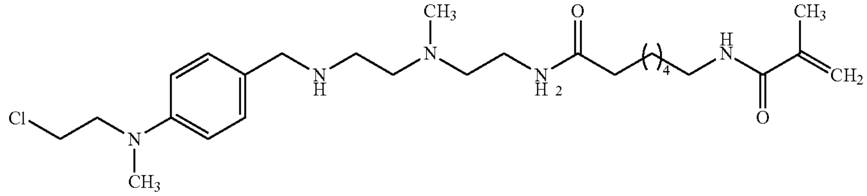
IIIA-19
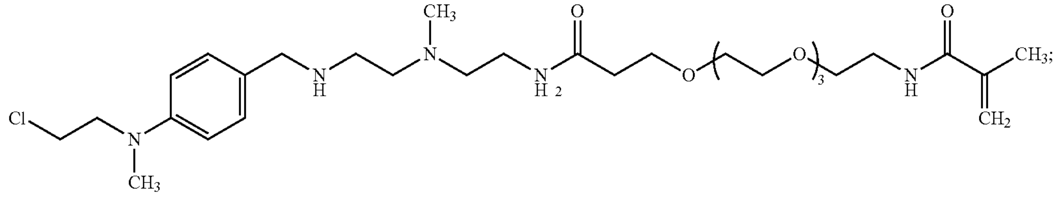
and
IIIA-20
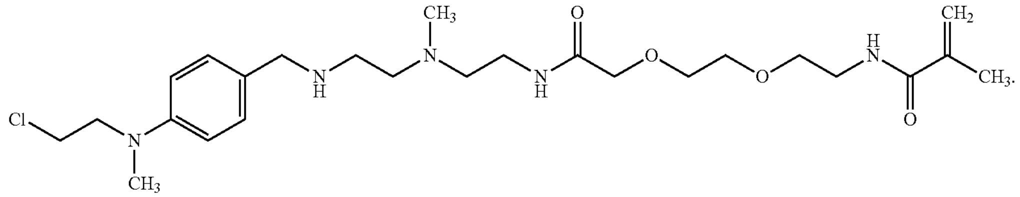
Non-limiting examples of compounds of Formula (IIIB) include:
IIIB-1
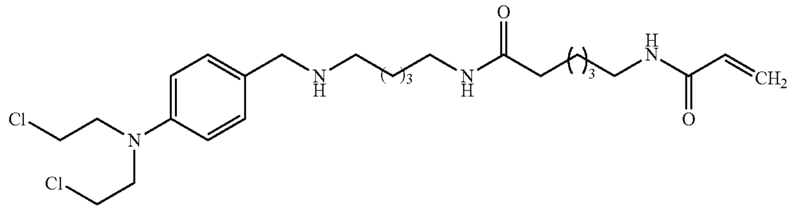

-continued
IIIB-2
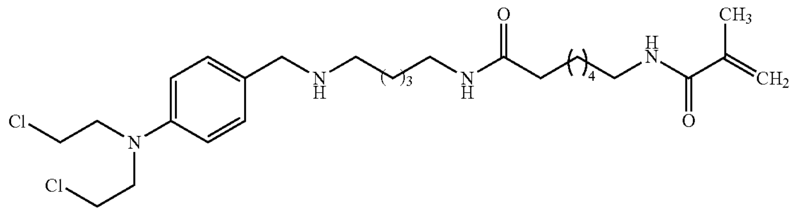
IIIB-3
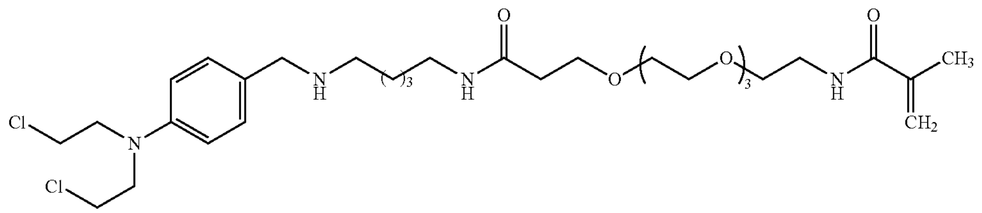
IIIB-4
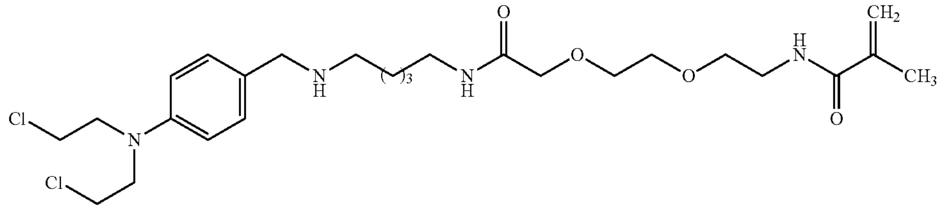
IIIB-5
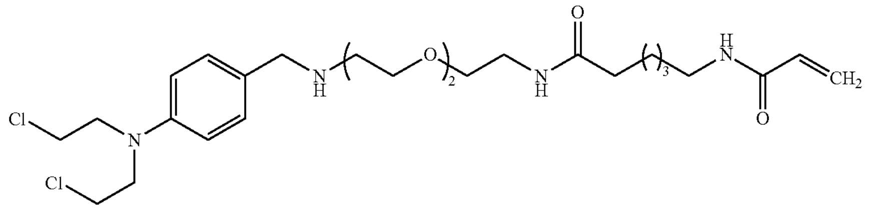
IIIB-6
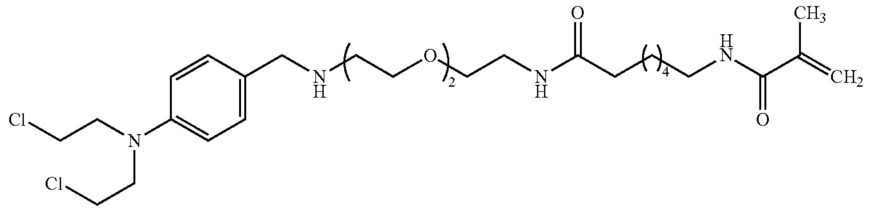
IIIB-7
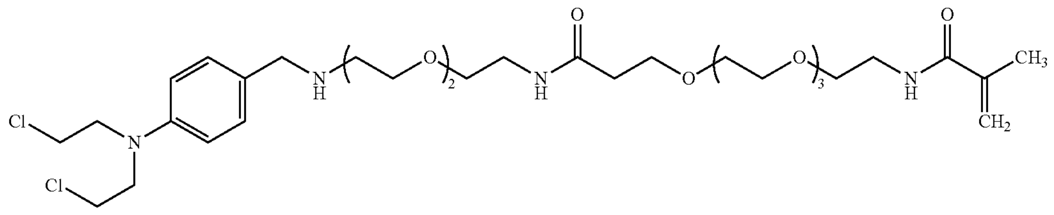
IIIB-8
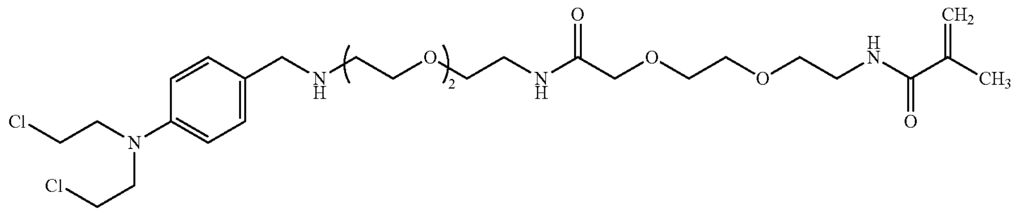

-continued
IIIB-9
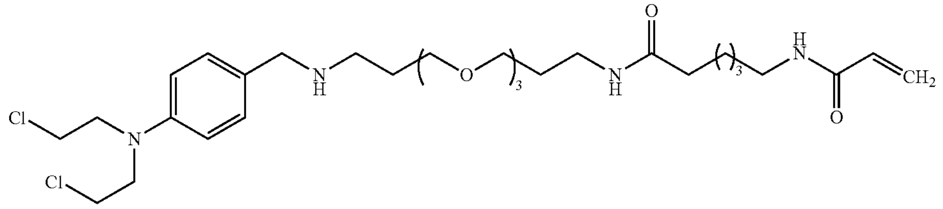
IIIB-10
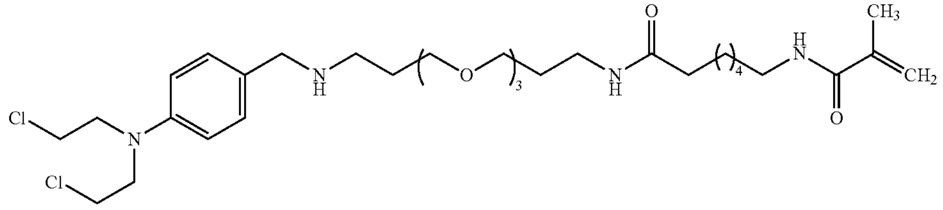
IIIB-11
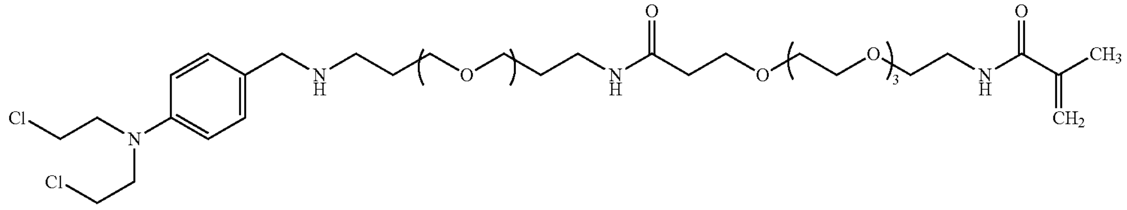
IIIB-12
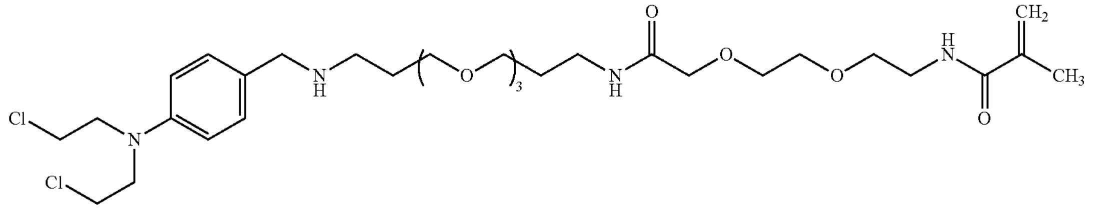
IIIB-13
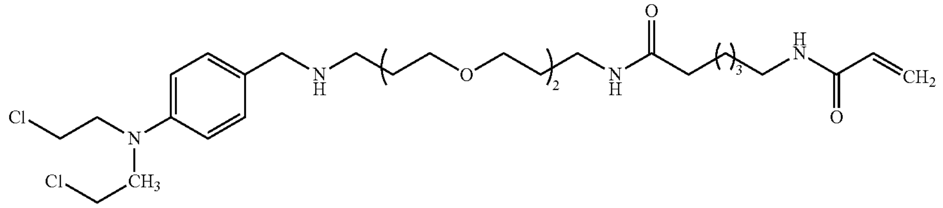
IIIB-14
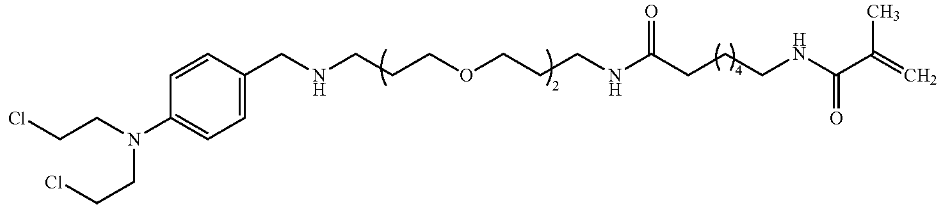
IIIB-15
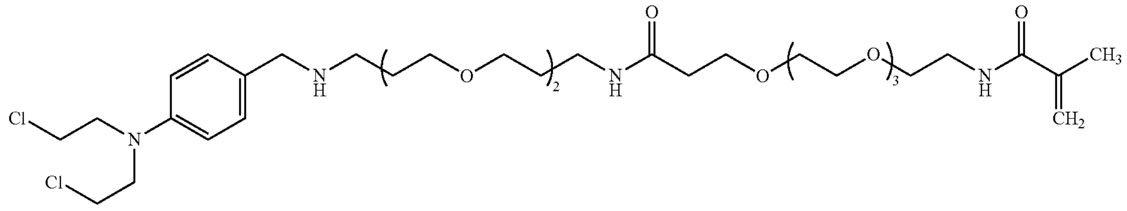

-continued

IIIB-16

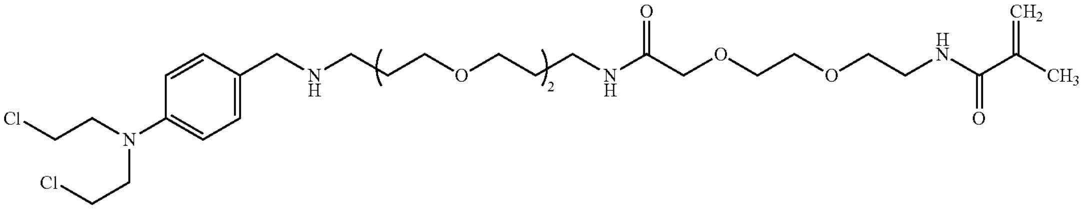

IIIB-17

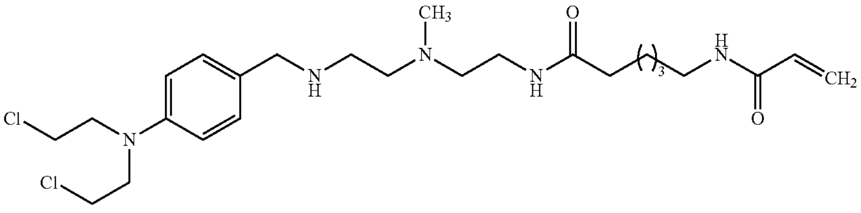

IIIB-18

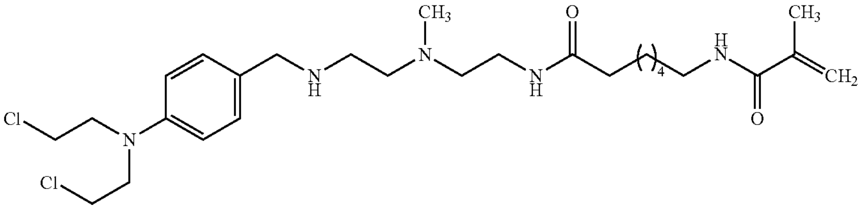

IIIB-19

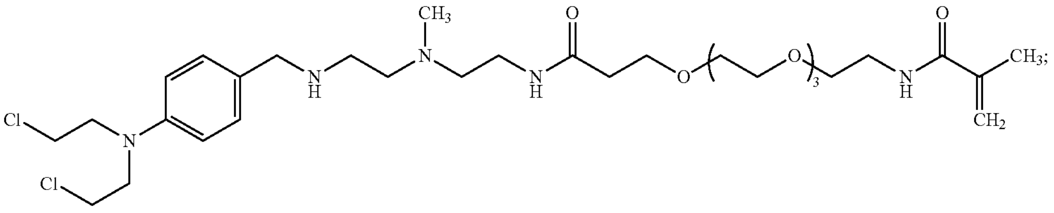

and

IIIB-20

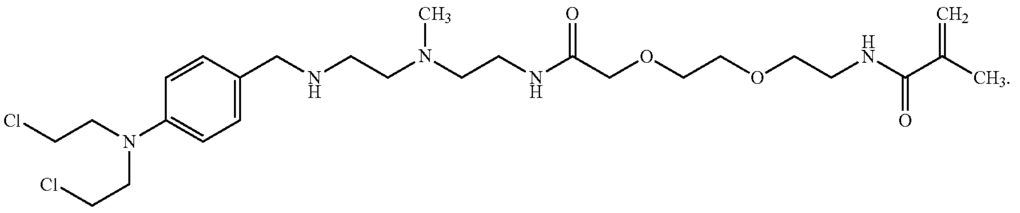

Methods for Using Disclosed Compounds

In aspects of this disclosure, the compounds described herein are used, in some embodiments, in the practice of the technique of expansion microscopy (ExM), which is employed in order to spatially resolve proteins and nucleic acid targets such as ribonucleic acid (RNA) targets within cleared tissue samples. In ExM, biological samples are permeated with a solution of water soluble small-molecule monomers which are polymerized into a swellable hydrogel that can expand upon addition of water, allowing for an enhancement in spatial resolution and specimen clearing. The tissues are then stained for proteins or nucleic acids (e.g., RNA) of interest and imaged. In some embodiments, specimens are denatured to displace the probes, and the tissues can then be re-stained for new nucleic acid genes, thereby facilitating serial labeling and readout of a large number of probes in a single sample across thick specimen regions. This, in turn, allows for effective transcriptional profiling of thousands of genes across entire complex tissues. Similar multiplexing can be performed with successive probes for proteins (e.g., antibodies or their antigen-binding fragments).

In ExM, 3-dimensional imaging with nanoscale precision is performed on cells and tissues. This is accomplished by physically expanding the biological sample using a dense polymer matrix. The compounds disclosed herein are used, in some embodiments, to cross-link proteins and/or nucleic acids of interest into the gel, such that their spatial location to subcellular structures is preserved.

In some embodiments, methods are provided to anchor native proteins within fresh frozen tissue sections and to perform the ExM procedure to physically expand the specimens, to employ labeled antibody staining to detect locations of proteins of interest. In some embodiments, labeled antibodies may be used to stain the specimen before the expansion process, in which case the compounds described herein may be used to cross-link labeled antibodies into the gel to preserve the location of the labeled antibodies to the positions of interest.

In some embodiments, methods are provided to anchor native nucleic acids within fresh frozen tissue sections and to perform the ExM procedure to physically expand the specimens, to employ hybridization chain reaction (HCR) signal amplification in order to obtain high signal-to-noise puncta readout, and optionally, to use DNAse I to dislocate and wash out the initiator probes and rehybridize new probes for serial hybridization.

In some embodiments, both proteins and nucleic acids in a sample are reacted with gel binding moiety reagents as described herein, in successive steps (protein linking followed by nucleic acid linking, or nucleic acid linking followed by protein linking), or both proteins and nucleic acids can be reacted concurrently or simultaneously. Any of the exemplary descriptions herein may be applied to the successive or concurrent use of the compounds disclosed herein, and in some embodiments, more than one protein linking compound and/or nucleic acid linking compound may be employed in the processing of a sample.

In some embodiments, the sample is contacted with a gel binding moiety such as the compounds of Formula (I) that operably link (e.g., covalently) to protein in the sample. As noted here, such proteins may in one embodiment may be the proteins of interest; in other embodiments, such proteins may be labeled antibodies of binding fragments thereof bound to proteins of interest. As noted below, the later steps in ExM tend to degrade proteins, so that procedures utilizing labeled protein-detecting reagents such as fluorescently-labeled antibodies, labeled binding fragments, labeled ScFv, etc., used before cross-linking and subsequent ExM steps is typically performed. Next the sample is infused with a monomer solution that permeates into the tissue. Free radical polymerization of this solution creates a polymer network that is covalently conjugated to the gel binding moiety, (optionally also physically connected to RNA-binding-groups either through a linker molecule or a customized bioconjugation chemistry). The sample is then digested and the hydrogel expands uniformly. Then, the sample is imaged (or first treated with a labeled reagents that bind to the proteins of interest, e.g., fluorescently-labeled antibodies, antigen-binding fragments thereof, ScFv, etc., to the protein being analyzed, if still detectable after ExM steps including digestion). The result is a polymer network that contains fluorescent dyes where the target proteins are (and optionally also where target RNAs were) located. This process has many advantages. Notably, it allows pseudo super resolution imaging with conventional confocal microscopy because the imaging targets are no longer diffraction limited. Additionally, the tissue digestion clears the sample allowing imaging deep into thick tissues samples.

In some embodiments, the sample is contacted with a gel binding moiety such as the compounds of Formula (IIA-B) or Formula (IIIA-B) that operably link (typically covalently) to RNA in the sample. Next the sample is infused with a monomer solution that permeates into the tissue. Free radical polymerization of this solution creates a polymer network that is covalently conjugated to the gel binding moiety, (optionally also physically connected to protein-binding-groups either through a linker molecule or a customized bioconjugation chemistry). The sample is then digested and the hydrogel expands uniformly. Then, the sample is treated with an RNA-binding-group (typically a single-stranded nucleic acid, such as a deoxyribonucleic acid [DNA] primer) that selectively binds to the RNA being analyzed, and then labeled (typically fluorescently) by HCR amplification. The result is a polymer network that contains fluorescent dyes where the target RNAs are (and optionally also where target proteins were) located. This process has many advantages. Notably, it allows pseudo super resolution imaging with conventional confocal microscopy because the imaging targets are no longer diffraction limited. Additionally, the tissue digestion clears the sample allowing imaging deep into thick tissues samples.

As mentioned above, at least one of a compound disclosed herein may be used in the same specimen for cross-linking both proteins and/or RNA into the gel. In other embodiments, a protein cross-linking agent such as Acryloyl-X (AcX), or a nucleic acid cross-linking agent such as NucliX, LabelX, MalphaX, may be used in combination with a compound disclosed herein. In some embodiments, a protein cross-linking agent of Formula (I) and a protein cross-linking agent such as Acryloyl-X may be used. In some embodiments, a nucleic acid cross-linking agent of Formula (IIA-IIB) or Formula (IIIA-IIIB) and a nucleic acid cross-linking agent such as NucliX, LabelX or MalphaX may be used together. In one embodiment, at least one of a compound of Formula (I) and a compound of Formula (IIA-IIB) or Formula (IIIA-IIIB) is used in a procedure such as but not limited to ExM.

In one aspect, provided herein are methods of labeling nucleic acids and proteins together in a biological sample, said method comprising: (a) contacting the sample with a first gel binding moiety and a second gel binding moiety under conditions wherein the first gel binding moiety operably links to proteins (e.g., compounds of Formula (I)) in the sample and the second gel binding moiety operably links to nucleic acids in the sample (e.g., compounds of formulas IIA, IIB, IIIA or IIIB), and wherein at least one of the first gel binding moiety and second gel binding moiety is provided by a compound of Formula (I) or Formula (IIA-B) or Formula (IIIA-B); (b) contacting the sample with a solution comprising monomers of a polyelectrolyte gel; (c) by free radical polymerization, polymerizing said monomers to form the polyelectrolyte gel and covalently conjugating the first and second gel binding moieties to the polyelectrolyte gel; (d) proteolytically digesting said sample; and (e) dialyzing said sample to expand said polyelectrolyte gel. In some embodiments, further steps comprise providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (p) contacting the sample with the plurality of initiator DNA probes under conditions wherein the sequence complementary to the sequence from one of the nucleic acid targets of interest hybridizes to that sequence from the nucleic acid target of interest; (q) for each initiator DNA probe, providing a pair of fluorophore-labeled DNA hairpins that metastably co-exist in the absence of the initiator DNA probe; and (r) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe. In some embodiments, the methods further comprising, prior to step (a), the steps of: (I) contacting the sample with at least one primary antibody under conditions where it selectively recognizes a target protein of interest; and (II) contacting the sample with at least one secondary antibody operably linked to a detectable label.

In another aspect, provided herein are methods of labeling a biological sample comprising a nucleic acid such as a ribonucleic acid (RNA) target of interest, said methods being performed under RNAse-free conditions and said methods comprising: (a) contacting the sample with a gel binding moiety under conditions wherein the gel binding moiety operably links to RNA in the sample, and and wherein at least one gel binding moiety is provided by a compound of Formula (IIA-B) or Formula (IIIA-B); (b) contacting the sample with a solution comprising monomers of a polyelectrolyte gel; (c) by free radical polymerization, polymerizing said monomers to form the polyelectrolyte gel and covalently conjugating the gel binding moiety to the polyelectrolyte gel; (d) proteolytically digesting said sample; and (e) dialyzing said sample to expand said polyelectrolyte gel. In some embodiments, further steps include providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (p) contacting the sample with the plurality of initiator DNA probes under conditions wherein the sequence complementary to the sequence from one of the RNA targets of interest hybridizes to that sequence from the RNA target of interest; (q) for each initiator DNA probe, providing a pair of fluorophore-labeled DNA hairpins that metastably co-exist in the absence of the initiator DNA probe; and (r) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe.

In another aspect, provided herein are methods of imaging nucleic acids and proteins together in a biological sample, said method comprising: (a) contacting the sample with a first gel binding moiety and a second gel binding moiety under conditions wherein the first gel binding moiety operably links to proteins in the sample and the second gel binding moiety operably links to nucleic acids in the sample, and wherein at least one of the first gel binding moeity and second gel binding moiety is provided by a compound of Formula (I) or Formula (IIA-B) or Formula (IIIA-B), and wherein the protein and nucleic acid compounds are used sequentually in either order or concurrently; (b) contacting the sample with a solution comprising monomers of a polyelectrolyte gel; (c) by free radical polymerization, polymerizing said monomers to form the polyelectrolyte gel and covalently conjugating the first and second gel binding moieties to the polyelectrolyte gel; (d) proteolytically digesting said sample; and (e) dialyzing said sample to expand said polyelectrolyte gel. In some embodiments, further steps include providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (p) contacting the sample with the plurality of initiator DNA probes under conditions wherein the sequence complementary to the sequence from one of the nucleic acid targets of interest hybridizes to that sequence from the nucleic acid target of interest; (q) for each initiator DNA probe, providing a pair of fluorophore-labeled DNA hairpins that metastably co-exist in the absence of the initiator DNA probe; (r) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe; and(s) obtaining an image of the sample. In some embodiments, the methods further comprising, prior to step (a), the steps of: (I) contacting the sample with at least one primary antibody under conditions where it selectively recognizes a target protein of interest; and (II) contacting the sample with at least one secondary antibody operably linked to a detectable label.

In another aspect, provided herein are methods of imaging nucleic acid such as ribonucleic acid (RNA) in a biological sample, said method being performed under RNAse-free conditions and said method comprising: (a) contacting the sample with a gel binding moiety under conditions wherein the gel binding moiety operably links to RNA in the sample, and wherein the gel binding moiety is provided by a compound of Formula (IIA-B) or Formula (IIIA-B); (b) contacting the sample with a solution comprising monomers of a polyelectrolyte gel; (c) by free radical polymerization, polymerizing said monomers to form the polyelectrolyte gel and covalently conjugating the gel binding moiety to the polyelectrolyte gel; (d) proteolytically digesting said sample; and (e) dialyzing said sample to expand said polyelectrolyte gel. In some embodiment, further steps include providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (p) contacting the sample with the plurality of initiator DNA probes under conditions wherein the sequence complementary to the sequence from one of the RNA targets of interest hybridizes to that sequence from the RNA target of interest; (q) for each initiator DNA probe, providing a pair of fluorophore-labeled DNA hairpins that metastably co-exist in the absence of the initiator DNA probe; (r) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe; and(s) obtaining an image of the sample.

In another aspect, provided herein are methods of imaging nucleic acids and proteins together in a biological sample, said method comprising: (a) contacting the sample with a first gel binding moiety and a second gel binding moiety under conditions wherein the first gel binding moiety operably links to proteins in the sample and the second gel binding moiety operably links to nucleic acids in the sample, and wherein at least one of the first gel binding moiety and second gel binding moiety is provided by a compound of Formula (I) or Formula (IIA-B) or Formula (IIIA-B) and wherein the first and second gel binding moieties are contacted sequentially in either irder, or concurrently; (b) contacting the sample with a solution comprising monomers of a polyelectrolyte gel; (c) by free radical polymerization, polymerizing said monomers to form the polyelectrolyte gel and covalently conjugating the first and second gel binding moieties to the polyelectrolyte gel; (d) proteolytically digesting said sample; and (e) dialyzing said sample to expand said polyelectrolyte gel. In some embodiments, further steps include providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence;

(p) contacting the sample with the plurality of initiator DNA probes under conditions wherein the sequence complementary to the sequence from one of the nucleic acid targets of interest hybridizes to that sequence from the nucleic acid target of interest; (q) for each initiator DNA probe, providing a pair of fluorophore-labeled DNA hairpins that metastably co-exist in the absence of the initiator DNA probe; (r) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe; (s) obtaining an image of the sample; (t) treating the sample with a deoxyribonuclease to remove the initiator DNA probes and amplification polymers; and (u) repeating steps (p)-(s) one or more times for additional RNA targets of interest. In some embodiments, the methods further comprising, prior to step (a), the steps of: (I) contacting the sample with at least one primary antibody under conditions where it selectively recognizes a target protein of interest; and (II) contacting the sample with at least one secondary antibody operably linked to a detectable label.

In another aspect, provided herein are methods of imaging nucleic acids such as ribonucleic acid (RNA) in a biological sample, said method being performed under RNAse-free conditions and said method comprising: (a) contacting the sample with a gel binding moiety under conditions wherein the gel binding moiety operably links to RNA in the sample, wherein the gel binding moiety is provided by a compound of Formula (IIA-B) or Formula (IIIA-B); (b) contacting the sample with a solution comprising monomers of a polyelectrolyte gel; (c) by free radical polymerization, polymerizing said monomers to form the polyelectrolyte gel and covalently conjugating the gel binding moiety to the polyelectrolyte gel; (d) proteolytically digesting said sample; and (e) dialyzing said sample to expand said polyelectrolyte gel. In some embodiments, further steps include providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (p) contacting the sample with the plurality of initiator DNA probes under conditions wherein the sequence complementary to the sequence from one of the RNA targets of interest hybridizes to that sequence from the RNA target of interest; (q) for each initiator DNA probe, providing a pair of fluorophore-labeled DNA hairpins that metastably co-exist in the absence of the initiator DNA probe; (r) contacting the sample with the fluorophore-labeled DNA hairpins under conditions wherein the hairpins self-assemble by HCR, in the presence of their corresponding initiator DNA probe, into fluorescent amplification polymers tethered to that corresponding initiator DNA probe; (s) obtaining an image of the sample; (t) treating the sample with a deoxyribonuclease to remove the initiator DNA probes and amplification polymers; and (l) repeating steps (p)-(s) one or more times for additional RNA targets of interest.

As noted herein, a compound of Formula (I), (IIA-IIB) or (IIIA-IIIB) may be used together with one or more other cross-linking agents such as succinimidyl ester of 6-((acryloyl)amino)hexanoic acid (Acryloyl-X), methacrylic acid N-hydroxysuccinimide ester, acrylic acid N-hydroxysuccinimide ester, N—N'-(4-(2-chloroethyl)-methylamino-benzylamine-3-aminopropyl-N,N-dimethyl-3-aminopropylammonium, structures of some of which are shown below.

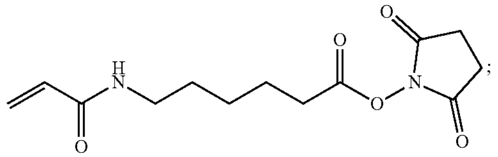

Acryloyl-X

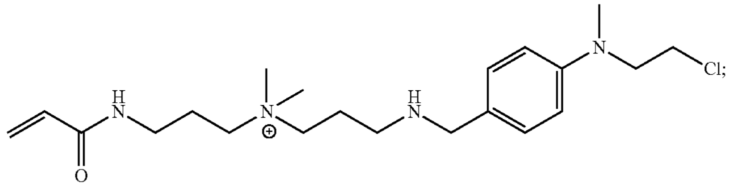

NucliX

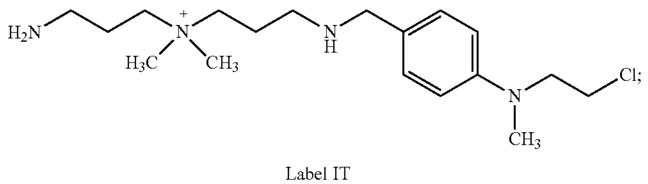

Label IT

-continued

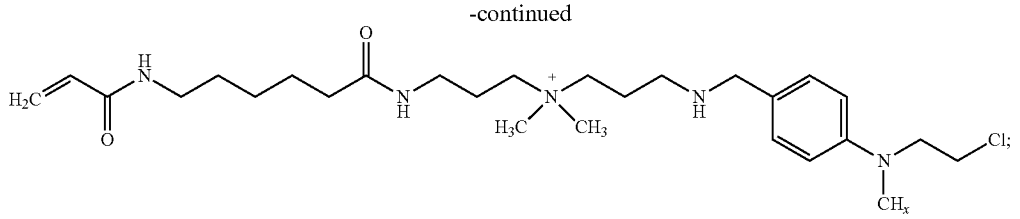

Label X

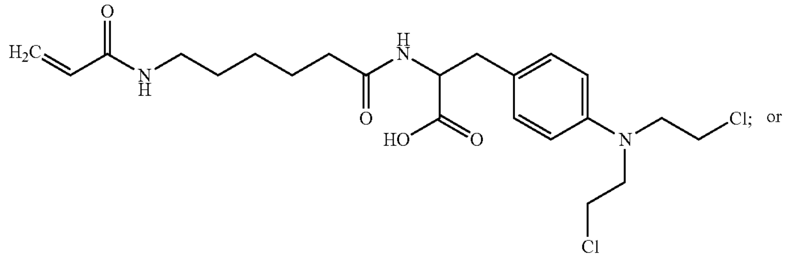

MelphaX

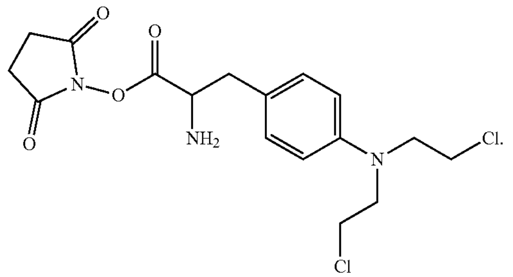

In another aspect, provided herein are additional methods, as well as reagents (e.g., the binding compositions, labels nucleic acid probes) and kits for use in the methods described herein. For example, provided herein are methods for embedding a sample in a polyacrylamide gel matrix using a borate buffer.

In some embodiments, the methods described herein further comprise obtaining an image of the sample. In some embodiments, the image is obtained by confocal microscopy.

With respect to the above methods, compositions, or kits, in some embodiments, the nucleic acid target of interest is a RNA target of interest and comprises an mRNA. In some embodiments, the RNA target of interest is an mRNA target of interest and the sequence complementary to a sequence from the mRNA target of interest is at least partially complementary to an exon of said mRNA and at least partially complementary to an intron adjacent to said exon.

With respect to the above methods, an image of the sample may be obtained before expanding the polyelectrolyte gel, as well as after expanding the polyelectrolyte gel.

With respect to the above methods, compositions, or kits, in some embodiments, detectable labels are used (e.g., detectably-labeled DNA hairpins). Examples of detectable labels include, but are not limited to, fluorescent labels or fluorophores. Examples of fluorophores include, but are not limited to, fluorescein isothiocyanate (FITC), tetramethylrhodamine (TRITC), 4',6-diamidino-2-phenylindole (DAPI), or cyanine dye 5 (Cy5), Alexa 488, Alexa 514, Alexa 546, Alexa 594, and Alexa 647. In some embodiments, for a pair of fluorophore-labeled DNA hairpins both hairpins are labeled with the same fluorophore. In some embodiments, for a pair of fluorophore-labeled DNA hairpins each hairpin is labeled with a different fluorophore. In some embodiments, only one of the pair of fluorophore-labeled DNA hairpins is labeled with a fluorophore. Examples of fluorophores used to label DNA hairpins for HCR include, but are not limited to, fluorescein isothiocyanate (FITC), tetramethylrhodamine (TRITC), 4',6-diamidino-2-phenylindole (DAPI), or cyanine dye 5 (Cy5), Alexa 488, Alexa 514, Alexa 546, Alexa 594, and Alexa 647.

With respect to the above methods, compositions, or kits, in some embodiments, detection reagents specific for the detectable labels are provided.

In some embodiments, the methods described herein further comprise the step of: removing the initiator DNA probes unhybridized to the RNA target(s) of interest.

In some embodiments, the initiator DNA probes are preferably between 56 and 60 nucleotides in length. In some embodiments, the fluorophore-labeled DNA hairpins are preferably between 72 and 74 nucleotides in length.

With respect to the above methods, compositions, or kits, in some embodiments, the gel binding moiety is an acryloyl or methacryloyl group. In some embodiments, the gel binding moiety is selected at least from among compounds of Formula (I) or Formula (IIA-B) or Formula (IIIA-B). In some embodiments, a compound of Formula (I) or Formula (IIA-B) or Formula (IIIA-B) may be used in a method, composition or kit further comprising Acryloyl-X (6-((acryloyl)amino)hexanoic acid succinimidyl ester), NucliX, Label-X, Label-IT, MalphaX, or any combination thereof.

In some embodiments, the monomer solution comprises sodium acrylate, acrylamide, and N—N'-methylenebisacrylamide. In some embodiments, free radical polymerization is induced with ammonium persulfate (APS) initiator and tetramethylethylenediamine (TEMED).

In some embodiments, the biological sample is chemically fixed and permeabilized prior to step (a) of the methods described herein. In some embodiments, dialyzing the sample to expand the polyelectrolyte gel comprises dialyzing it in water.

With respect to the above methods, compositions, or kits, in some embodiments, the methods further comprise performing the method on a plurality of biological samples in an array or in a microarray. In some embodiments, the array comprises a multiwell plate with each of the plurality of biological samples in a separate well of the multiwell plate. In some embodiments, the multiwell plate comprises a multiwell format of 12, 24, 48, or 96 wells. In some embodiments, said multiwell format comprises a high-throughput multiwell format.

With respect to the above methods or kits, in some embodiments, at least a portion of the method is automated.

With respect to the above methods, compositions, or kits, in some embodiments, the biological sample is derived from a multicellular organism. In some embodiments, the multicellular organism is a vertebrate. In some embodiments, the vertebrate is a mammal or a bird. In some embodiments, the mammal is a human. Alternatively, in some embodiments, the mammal is a non-human mammal. In some embodiments, the biological sample is a brain, heart, lung, gastrointestinal, circulatory, kidney, urogenital, pancreatic, gall bladder, muscle, breast, glandular, or bone sample. In some embodiments, the biological sample comprises serial sections from a single organism, such as a human, and the methods described herein further comprise repeating the method on the serial sections in an array comprising a multiwell plate where each of the serial sections is ordered in a separate well of the plate. Examples of serial sections may include cross-sections or sagittal sections, such as those of an organ, a portion of an organ, a whole organism, or a portion of an organism. An organism includes an embryo. The biological sample may be fresh, frozen, previously mounted, or fresh-frozen.

In some embodiments, the methods described herein further comprise obtaining images of the plurality of serial sections and constructing a three-dimensional model from those images.

With respect to the above methods, compositions, and kits, in some embodiments, the initiator DNA probe has a dissociation constant ($K_D$) less than about $1\times10^{-5}$ M, less than about $1\times10^{-6}$ M, or less than about $1\times10^{-7}$ M. With respect to the above methods, compositions, and kits, in some embodiments, the hairpin molecules have a dissociation constant ($K_D$) less than about $1\times10^{-5}$ M, less than about $1\times10^{-6}$ M, or less than about $1\times10^{-7}$ M.

In some embodiments, the methods further comprise the step of removing the gel binding moieties unconjugated to the polyelectrolyte gel after free radical polymerization.

With respect to methods, in some embodiments, target biomolecules, such as proteins, are detected with antibodies, which include primary and secondary antibodies, or antigen-binding fragments. In some embodiments, the antibodies may be monoclonal or polyclonal antibodies. In some embodiments, the antigen-binding fragments may be derived from polyclonal or monoclonal antibodies. In some embodiments, the antigen-binding fragment is selected from the group consisting of a Fab, a Fab', a $(Fab')_2$, a F(ab')2, a Fv, a single chain antibody (SCA), and a scFv-Fc. In some embodiments, the affinity of the antigen-binding site for the expansion target biomolecule is a high affinity with an affinity constant ($K_a$) greater than $10^4$ $M^{-1}$ or it is between $10^5$-$10^{11}$ $M^{-1}$. A specific binding composition may have a dissociation constant ($K_D$) less than about $1\times10^{-5}$ M, less than about $1\times10^{-6}$ M, or less than about $1\times10^{-7}$ M.

In some embodiments, where preparation of a microarray is concerned, the method also comprises capture element sythesis, preparation of a solid support surface, immobilization of capture elements onto the solid support (e.g., via a robotic arrayer), binding of the target molecule to the immobilized capture elements, and detection and quantification of the target/capture element complex. In some embodiments, at least some part of the method is automated.

Nucleic Acids

As used herein, the terms "polynucleotide" and "nucleic acid molecule" are used interchangeably to refer to polymeric forms of nucleotides of any length, which may have any three-dimensional structure, and may perform any function, known or unknown. The polynucleotides may contain deoxyribonucleotides (DNA), ribonucleotides (RNA), and/or their analogs, including, but not limited to, single-, double-stranded and triple helical molecules, a gene or gene fragment, exons, introns, messenger RNA (mRNA), transfer RNA (tRNA), ribosomal RNA (rRNA), microRNA (mtiRNA), non-coding RNA (ncRNA), small interfering RNA (siRNA), ribozymes, antisense molecules, complementary DNA (cDNA), genomic DNA (gDNA), recombinant polynucleotides, branched polynucleotides, aptamers, plasmids, vectors, isolated DNA sequences, isolated RNA sequences, nucleic acid probes, peptide nucleic acids (PNA), and primers. A nucleic acid molecule may also comprise modified nucleic acid molecules (e.g., comprising modified bases, sugars, and/or internucleotide linkers).

"Nucleic materials" and "materials from the nucleus" include the nuclear envelope and the contents of the nucleus, including genomic DNA (gDNA) or plasmid DNA. The "non-nucleic acid contents of the nucleus" include the components of the nuclear envelope and any other proteins or other substances of the nucleus that are not nucleic acids.

"Nucleic acids" include deoxyribonucleic acids (DNA) and ribonucleic acids (RNA) of various types, including genomic DNA (gDNA) and messenger RNA (mRNA) and derivatives thereof, such as modified DNA or RNA, including peptide nucleic acids (PNA). "Peptide nucleic acid" (PNA) is a polynucleotide analog in which the sugar-phosphate backbone is replaced by amide bonds. "Genetic material" comprises genomic DNA (gDNA), which is one type of DNA and encodes genetic information, or genetic RNA.

As used herein, a "genetic modification" refers to an addition, deletion or disruption to a cell's normal nucleotides. Art recognized methods include viral mediated gene transfer, liposome mediated transfer, transformation, transfection and transduction. As used herein, a "genetic mutation" is a genetic alteration and is a type of "genetic modification."

As used herein, a "polymorphism" or "genetic polymorphism" is a genetic variation and includes, but is not limited to, a single nucleotide polymorphism (SNP). As used herein, a "genotype" is the genetic composition of an organism, and a "phenotype" is the physical appearance or characteristics of an organism.

A "peptide" is a compound of two or more subunit amino acids, amino acid analogs, or peptidomimetics. The subunits may be linked by peptide bonds or by other bonds (e.g., as esters, ethers, and the like). An "amino acid" refers to either natural and/or unnatural or synthetic amino acids, including glycine and both D or L optical isomers, and amino acid analogs and peptidomimetics. "Amino acids" also includes imino acids. An "oligopeptide" refers to a short peptide chain of three or more amino acids. If the peptide chain is long (e.g., greater than about 10 amino acids), the peptide is a "polypeptide" or a "protein." While the term "protein" encompasses the term "polypeptide," a "polypeptide" may be a less than full-length protein.

As used herein, "expression" refers to the process by which polynucleotides are transcribed into mRNA and/or translated into peptides, polypeptides, or proteins. If the polynucleotide is derived from genomic DNA, expression may, but is not required to, include splicing of the mRNA transcribed from genomic DNA, capping of the 5' end of the mRNA, polyadenylation of the 3' end of the mRNA, or other processing modifications or events.

In some embodiments of the present disclosure, the ribonucleic acid (RNA) target of interest is a messenger RNA (mRNA).

RNA, including mRNA, is known in the art as being highly susceptible to degradation upon exposure to one or more RNAses. RNAses are present in a wide range of locations, including water, many reagents, laboratory equipment and surfaces, skin, mucous membranes, and elsewhere. It is known in the art that working with RNA generally requires preparing an RNAse-free environment and materials, as well as taking precautions to avoid introducing RNAses into an RNAse-free environment.

RNAse-free precautions are known in the art. These include, but are not limited to, cleaning surfaces with an RNAse cleaning product (e.g., RNASEZAP™ [Ambion] and other commercially available products or 0.5% sodium dodecyl sulfate [SDS] followed by 3% $H_2O_2$); using a designated workspace, materials, and equipment (e.g., pipets, pipet tips); using barrier tips; baking designated glassware (e.g., 300° C. for 2 hours) prior to use; treating enyzmes, reagents, and other solutions (e.g., with diethyl pyrocarbonate [DEPC] or dimethyl pyrocarbonate [DMPC]) or using commercially available, certified RNAse-free water or solutions, or ultrafiltered water (e.g., for Tris-based solutions); including an RNAse inhibitor while avoiding temperatures or denaturing conditions that could deactivate the inhibitor); and wearing clean gloves (while avoiding contaminated surfaces) and a clean lab coat. Some solutions (but not Tris-based solutions) can be treated with 0.5 ml DEPC/L, followed by incubation for 2 hours at 37° C., and autoclaving, preferably for at least 45 minutes. Water may be treated with 0.1% v/v DEPC for at least 2 hours at 37° C., then autoclaved. Additional techniques may be useful for procedures in which the RNA is isolated from the sample (e.g., use of TRIZOL™ [Invitrogen] reagents).

RNAses in a biological sample of interest may be inhibited either by rinsing in RNAse-free water and snap freezing the tissue, e.g., in liquid nitrogen, for use at a later date. Alternatively, the biological sample may be stored in ethanol or in an RNAse inhibitor-containing solution at −80° C.

A nucleic acid may have a sequence of at least 65% complementarity; at least 75% complementarity; at least 85% complementarity; at least 95% complementarity; at least 97% complementarity; or at least 99% complementarity to a target or other sequence of interest.

With respect to nucleic acids, "specificity" refers to identity or complementarity as a function of competition or recognition/binding, respectively. "Specificity" of recognition or binding may be affected by the conditions under which the recognition or binding takes place (e.g., pH, temperature, salt concentration, and other factors known in the art) to effect "hybridization" of one nucleic acid domain to another (see, e.g., Wetmur, "DNA Probes: Applications of the Principles of Nucleic Acid Hybridization," *Critical Reviews in Biochemistry and Molecular Biology* 26(3/4): 227-259 (1991)). It is understood that a practitioner may vary conditions without undue experimentation. For example, the practitioner may calculate the melting temperature of a DNA complex, an RNA complex, or a DNA/RNA hybrid complex and adjust conditions accordingly.

"Conservatively modified variants" of sequences may also be envisioned. With respect to particular nucleic acid sequences, conservatively modified varients refers to those nucleic acids which encode identical or essentially identical amino acid sequences, or where the nucleic acid does not encode an amino acid sequence, to essentially identical sequences. Specifically, degenerate codon substitutions can be achieved by generating sequences in which the third position of one or more selected (or all) codons is substituted with mixed base and/or deoxyinosine or other modified residues. Alternatively, one or more amino acids may be substituted with an amino acid having a similar structure, activity, charge, or other property. Conservative substitution tables providing functionally similar amino acids are well-known in the art (see, e.g., *Proc.Natl.Acad.Sci.USA* 89:10915-10919 (1992)).

As used herein, "expression" refers to the process by which polynucleotides are transcribed into mRNA and/or translated into peptides, polypeptides, or proteins. If the polynucleotide is derived from genomic DNA, expression may include, but is not required to include, splicing of the mRNA transcribed from the genomic DNA, capping of the 5' end of the mRNA, polyadenylation of the 3' end of the mRNA, or other processing modifications or events.

Where an RNA target of interest is specifically an mRNA in the process of being transcribed or newly transcribed (but prior to the step of intron-splicing during post-transcriptional processing), such as when a practitioner is interested in changes in levels of transcription (e.g., in response to a particular stimulus) in an organism, the initiator DNA probes can be constructed to bridge an exon-intron boundary in the unprocessed mRNA sequence. For example, by using a probe that hybridizes partially to an exon of the mRNA target and partially to an intron adjacent to the exon, such that the probe domain overlaps the exon-intron boundary (i.e., the probe domain hybridizes to an exon sequences adjacent to the exon-intron boundary and intron sequences adjacent to the exon sequences at the exon-intron boundary).

Antibodies and Antigens

As used herein, the term "antibody" encompasses the structure that constitutes the natural biological form of an antibody. In most mammals, including humans, and mice, this form is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, Cγ1, Cγ2, and Cγ3. In each pair, the light and heavy chain variable regions ($V_L$ and $V_H$) are together responsible for binding to an antigen, and the constant regions ($C_L$, Cγ1, Cγ2, and Cγ3, particularly Cγ2, and Cγ3) are responsible for antibody effector functions. In some mammals, for example in camels and llamas, full-length antibodies may consist of only two heavy chains, each heavy chain comprising immunoglobulin domains $V_H$, Cγ2, and Cγ3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full-length antibodies, antibody fragments, and individual immunoglobulin domains including but not limited to $V_H$, Cγ1, Cγ2, Cγ3, $V_L$, and $C_L$.

Depending on the amino acid sequence of the constant domain of their heavy chains, intact antibodies can be assigned to different "classes." There are five-major classes (isotypes) of intact antibodies: IgA, IgD, IgE, IgG, and IgM, and several of these may be further divided into "subclasses," e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known to one skilled in the art. While some antibodies are monomeric, most are multimers. As is well-known in the art, the subunits of most multimeric antibodies are linked to each other via disulfide bonds. For example, human IgG is comprised of two light chains and two heavy chains, with the two heavy chains typically linked by two disulfide bonds in the hinge region and with each light chain linked to a different heavy chain via a disulfide bond.

An "antibody" (Ab) is a protein that binds specifically to a particular substance, known as an "antigen" (Ag) (see below). An "antibody" or "antigen-binding fragment" is an immunoglobulin that binds a specific "epitope." The term encompasses polyclonal, monoclonal, and chimeric antibodies (e.g., multispecific antibodies). In nature, antibodies are generally produced by lymphocytes in response to immune challenge, such as by infection or immunization. An "antibody combining site" is that structural portion of an antibody molecule comprised of heavy and light chain variable and hypervariable regions that specifically binds antigen.

The terms "antibody" or "antigen-binding fragment" respectively refer to intact molecules as well as functional fragments thereof, such as Fab, a scFv-Fc bivalent molecule, $F(ab')_2$, and Fv that are capable of specifically interacting with a desired target. In some embodiments, the antigen-binding fragments comprise:

(1) Fab, the fragment which contains a monovalent antigen-binding fragment of an antibody molecule, which can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) $(Fab')_2$, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains;

(5) Single chain antibody ("SCA"), a genetically engineered molecule containing the variable region of the light chain and the variable region of the heavy chain, linked by a suitable polypeptide linker as a genetically fused single chain molecule; and (6) scFv-Fc, is produced by fusing single-chain Fv (scFv) with a hinge region from an immunoglobulin (Ig) such as an IgG, and Fc regions.

In some embodiments, an antibody provided herein is a monoclonal antibody. In some embodiments, the antigen-binding fragment provided herein is a single chain Fv (scFv), a diabody, a tandem scFv, a scFv-Fc bivalent molecule, an Fab, Fab', Fv, $F(ab')_2$ or an antigen binding scaffold (e.g., affibody, monobody, anticalin, DARPin, Knottin, etc.).

An "antigen" (Ag) is any substance that reacts specifically with antibodies or T lymphocytes (T cells). An "antigen-binding site" is the part of an immunoglobulin molecule that specifically binds an antigen. Additionally, an antigen-binding site includes any such site on any antigen-binding molecule, including, but not limited to an MHC molecule or T cell receptor, but it can also include any substance against which an antibody or antigen-binding fragment has been raised, including artificially manufactured antigens and/or artificially manufactured antibodies or antigen-binding fragments.

The term "antigenic material" covers a substance that will elicit an innate or adaptive immune response. As used herein, "a portion of antigenic material" covers antigenic material or fragment thereof, which is capable of eliciting an innate or adaptive immune response, even if the fragment is an incomplete representation or subset of the antigenic material as a whole. It can include the minimal antigen sequence required to elicit a specific immune response.

An "epitope" or "antigenic determinant" is a structure, usually made up of, but not limited to, a short peptide sequence or oligosaccharide, that is specifically recognized or specifically bound by a component of the immune system. It is the site on an antigen recognized by an antibody.

An antibody or antigen-binding fragment to a specific "expansion target biomolecule" specifically interacts with at least some component of that "expansion target biomolecule."

An "immunogen" is a substance capable of eliciting an immune response. Each immunoglobulin molecule can potentially bind a variety of antibodies directed at its unique features, or "idiotype," which is comprised of a series of "idiotopes." An "idiotope" is a single antigenic determinant on a variable region of an antibody or T cell receptor. It is the set of idiotopes on an antibody which comprise the idiotype that makes that antibody unique. The "dominant idiotype" is the idiotype found on the major fraction of antibodies generated in response to an antigen.

As used herein, the terms "binds" or "binding" or grammatical equivalents, refer to compositions, directly or indirectly, having affinity for each other. "Specific binding" is where the binding is selective between two molecules. A particular example of specific binding is that which occurs between an antibody and an antigen. Typically, specific binding can be distinguished from non-specific when the dissociation constant ($K_D$) is less than about $1\times10^{-5}$ M or less than about $1\times10^{-6}$ M or $1\times10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding. "Affinity" is defined as the strength of the binding interaction of two molecules, such as an antigen and its antibody, which is defined for antibodies and other molecules with more than one binding site as the strength of binding of the ligand at one specified binding site. Although the noncovalent attachment of a ligand to antibody is typically not as strong as a covalent attachment, "high affinity" is for a ligand that binds to an antibody or other molecule having an affinity constant ($K_a$) of greater than $10^4$ $M^{-1}$, typically $10^5$-$10^{11}$ $M^{-1}$; as determined by inhibition ELISA or an equivalent affinity determined by comparable techniques, such as Scatchard plots or using $K_a$/dissociation constant, which is the reciprocal of the $K_a$, etc.

In one embodiment, the antibody, antigen-binding fragment, or affinity tag binds its target with a $K_D$ of 0.1 nM-10 mM. In one embodiment, the antibody, antigen-binding fragment, or affinity tag binds its target with a $K_D$ of 0.1 nM-1 mM. In one embodiment, the antibody, antigen-binding fragment, or affinity tag binds its target with a $K_D$ within the 0.1 nM range. In one embodiment, the antibody, antigen-binding fragment, or affinity tag binds its target with a $K_D$ of 0.1-2 nM. In another embodiment, the antibody, antigen-binding fragment, or affinity tag binds its target with a $K_D$ of 0.1-1 nM. In another embodiment, the antibody, antigen-binding fragment, or affinity tag binds its target with a $K_D$ of 0.05-1 nM. In another embodiment, the antibody, antigen-binding fragment, or affinity tag binds its target with a $K_D$ of 0.1-0.5 nM. In another embodiment, the antibody, antigen-binding fragment, or affinity tag its target with a $K_D$ of 0.1-0.2 nM. In some embodiments, the antibody, antigen-binding fragment, or affinity tag bind its target directly. In some embodiments, the antibody, antigen-binding fragment, or affinity tag bind its target indirectly, for example, the antibody, antigen-binding fragment, or affinity tag is a secondary antibody that binds to an antibody bound to the target. "Specificity" refers to the ability of an antibody to discriminate between antigenic determinants. It also refers to the precise determinants recognized by a particular receptor or antibody. "Specificity" may be affected by the conditions under which the discrimination or recognition takes place (e.g., pH, temperature, salt concentration, and other factors known in the art).

A "peptide" is a compound of two or more subunit amino acids, amino acid analogs, or peptidomimetics. The subunits may be linked by peptide bonds or by other bonds (e.g., as esters, ethers, and the like). While the term "protein" encompasses the term "polypeptide," a "polypeptide" may be less than a full-length protein. However, the terms "polypeptide" and "protein" are used herein interchangeably and refer to any polymer of amino acids (dipeptide or greater) linked through peptide bods or modified peptide bonds. Thus, the terms "polypeptide" and "protein" include oligopeptides, protein fragments, fusion proteins, and the like. It should be appreciated that the terms "polypeptide" and "protein" can include moieties such as lipoproteins and glycoproteins, except where the context dictates otherwise.

A "tag peptide sequence" is a short peptide or polypeptide chain of 3 or more amino acids, which is attached to an antibody or other protein or moiety of interest. In some embodiments, a polypeptide, protein, or chimeric protein comprises a tag polypeptide sequence, which is used for purification, detection, labeling or some other function, such as by specific binding to an antibody. The antibody may be in solution or bound to a surface. The tag peptide sequence should not interfere with the function of the rest of the polypeptide, protein, or chimeric protein. Examples of tag proteins are well-known to those of ordinary skill in the art.

Probes and Labels

The word "label" as used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition, which is detectable.

As used herein, the term "probe" refers to synthetic or biologically produced nucleic acids that are designed to contain specific nucleotide sequences which hybridize under stringent conditions to target nucleic acid sequences. Conditions, such as pH, temperature, salt concentration, and other factors known in the art, may be varied to effect "hybridization" of one nucleic acid domain to another (see, e.g., Wetmur, "DNA Probes: Applications of the Principles of Nucleic Acid Hybridization," *Critical Reviews in Biochemistry and Molecular Biology* 26(3/4): 227-259 (1991)).

As used herein, a "labeled probe," "antibody operably linked to a label," "antibody operably linked to a detectable label," "antigen-binding fragment operably linked to a label," antigen-binding fragment operably linked to a detectable label," "nucleic acid probe operably linked to a detectable label," or "nucleic acid strand operably linked to a detectable label" refer to a probe which is prepared with a marker moiety, "label" or "detectable label" for detection. The marker moiety should be linked in a place and manner so as not to interfere with, significantly/substantially decrease or inhibit, the binding or affinity of the probe to the target. For example, with respect to an antibody (or antigen-binding protein) operably linked to a label, the label should be attached to the antibody (or antigen-binding fragment) in such a manner as to prevent the label from inhibiting binding of the antibody (or antigen-binding fragment) to its expansion target biomolecule. With respect to an antibody, the marker moiety is preferably attached to a constant region of the antibody, preferably to a Cγ2 or a Cγ3 region of a heavy chain. With respect to an antigen-binding fragment, the marker moiety is preferably attached to a constant region of the antigen-binding fragment. Alternatively, the label and/or the gel binding moiety is preferably operably linked at the location of one or more disulfide linkages with the antibody. With respect to a nucleic acid, the marker moiety is attached at either the 5' end, the 3' end, internally, or a suitable combination thereof. The preferred marker moiety is an identifying label, preferably a detectable label. In some embodiments, the detectable label is a fluorophore. In some embodiments, one probe may be attached to multiple marker moieties. In some embodiments, multiple types of probes are used, each type having a different marker moiety. The labeled probe may also be comprised of a plurality of different nucleic acid sequences and/or antibodies (or antigen-binding fragments) each labeled with one or more marker moieties. Each of the marker moieties may be the same or different. It may be beneficial to label the different probes (e.g., nucleic acid sequences, antibodies or antigen-binding fragments) each with a different marker moiety. This can be accomplished by having a single distinguishable moiety on each probe. For example, probe A may be attached to moiety X and probe B may be attached to moiety Y. Alternatively, probe A may be attached to moieties X and Y while probe B may be attached to moiety Z and W. As another alternative, probe A may be attached to moieties X and Y while probe B may be attached to moieties Y and Z. All the probes "A" and "B" described above would be distinguishable and uniquely labeled.

"Acrylates" or "polyacrylates" are a family of polymers made from acrylate monomers, which are esters having vinyl groups. Acrylate monomers include, but are not limited to acrylamide, N-siopproylacrulamide, dimethylacrylamide, acrylic acid, methacrylic acid, hydroxyl ethyl acrylamide, or oligo (ethylene glycol) methyl ether methacrylate, which can polymerize. For example, free radical polymerization of an acrylate monomer solution comprising sodium acrylate, acrylamide and N—N'-methylenebisacrylamide can be induced by the addition of ammonium persulfate (APS) initiator and tetramethylethylenediamine (TEMED).

In some embodiments, the antibody or antigen-binding fragment can be acrylated directly, making it suitable for polymerization. This process can be performed either before, after, or simultaneously with attachment of the detectable label (e.g., a fluorophore). The most straightforward way to acrylate antibodies is to use a reagent which can react with the many amino groups present on its surface such as the commercially available Acryoyl-X SE, 6-((acryloyl) amino)hexanoic acid, succinimidyl ester (Acryoyl-X, ThermoFisher A20770). Once the polymerizable group is presented on the surface of the antibody, free radical polymerization in its presence will result with it being attached to the polymer gel. Such acrylated antibodies are used in combination with at least one compound from Formula (I) or Formula (IIA-IIB) or Formula (IIIA-IIIB).

Direct acrylation of the antibody or antigen-binding fragment yields a "gel binding moiety" operably linked to the antibody or antigen-binding fragment. In some embodiments, the gel binding moiety is a compound of Formula (I) or any one of compounds I-1 to I-10.

During free radical polymerization of the acrylate monomers (above), the "gel binding moiety" is covalently conjugated to the polyelectrolyte gel, thereby indirectly attaching the labeled antibody or antigen-binding fragment to the resulting polyelectrolyte gel, or in some embodiments, the unlabeled protein in the specimen. The "gel binding moiety" should be linked to the antibody or antigen-binding fragment in a place and manner so as not to interfere with, significantly/substantially decrease or inhibit, the binding or affinity of the probe to the target and also so as not to interfere with, significantly/substantially decrease or inhibit, the detection of the marker moiety. For example, with respect to an antibody (or antigen-binding protein) operably linked to a gel binding moiety, the gel binding moiety should be attached to the antibody (or antigen-binding fragment) in such a manner as to prevent the gel binding moiety from inhibiting binding of the antibody (or antigen-binding fragment) to its expansion target biomolecule and should also be attached to the antibody (or antigen-binding fragment) in such a manner as to prevent the gel binding moiety from inhibiting detection of the label. With respect to an antibody, gel binding moiety is preferably attached to a constant region of the antibody, preferably to a Cγ2 or a Cγ3 region of a heavy chain. With respect to an antigen-binding fragment, the gel binding moiety is preferably attached to a constant region of the antigen-binding fragment. In some embodiments, the modified antibody comprises an antibody modified with a fluorophore operably linked to a constant region on one heavy chain and a gel binding moiety operably linked to a constant region on the other heavy chain.

Samples

"Biological sample" includes samples of organs, tissues, cells, blood, fluid, or other materials obtained from a biological organism. It also includes a biological organism, a cell, virus, or other replicative entity. Also included are solid cultures (including bacterial or tissue cultures). Also included are solid sample, including, but not limited to non-biological solids containing a biological organism, cell, virus, or other replicative entity; organs; tissues; cells; or sections (e.g., sagittal sections, cross-sections, and the like), washings, homogenizations, sonications, and similar treatments of biological samples. A biological sample may be obtained directly from a biological organism (e.g., a human or non-human animal, a plant, a fungus, a yeast, a protist, a bacterium or algae), it may be from a culture, or it may initially be attached to a non-biological solid. A biological sample may include a cancerous or noncancerous tumor or other growth, including a noncancerous aberrant growth.

A "physiological condition" of a biological organism may be normal or abnormal. The physiological condition may result from the genetic make-up of the organism (including, but not limited to, the expression of various proteins), from environmental factors (including, but not limited to, the ingestion of drugs, poisons, food, and beverages and the exposure of an organism to toxic or non-toxic substances), from disease (both infectious or non-infectious), from an injury, from a metabolic disorder, from pregnancy or nursing, and from a wide range of other circumstances, including genetic diseases, syndromes, and polymorphisms with respect to the genotype and/or phenotype of the organism, organ, tumor, tissue, or cell.

By "tissue sample" is meant a collection of similar cells obtained from a tissue of a subject or patient, preferably containing nucleated cells with chromosomal material. The four main human tissues are (1) epithelium; (2) the connective tissues, including blood vessels, bone and cartilage; (3) muscle tissue; and (4) nerve tissue. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. The tissue sample may contain compounds which are not naturally intermixed with the tissue in nature such as preservatives, anticoagulants, buffers, fixatives, nutrients, antibiotics, or the like.

For the purposes herein, a "section" of a tissue sample is meant a single part or piece of a tissue sample, e.g., a thin slice of tissue or cells cut from a tissue sample. It is understood that multiple sections of tissue samples may be taken and subjected to analysis. Types of sections include sagittal sections and cross-sections and may be individual or serial.

Alternatively, "whole mounts" may be studied. "Whole mounts" include, but are not limited to, an organ or an organism.

As used herein, "cell line" refers to a permanently established cell culture that will proliferate given appropriate fresh medium and space. In some embodiments, a cell line can be cultured and expanded to form a layer of cells, such as an adherent layer of cells, over the bottom of a plate or over the bottom of a well, such as a well of a multiwell plate.

The term "subject" refers to an organism, including a mammal (including a human) in need of therapy for, or susceptible to, a condition or its sequelae. The subject may include dogs, cats, pigs, cows, sheep, goats, horses, rats, and mice and humans. The term "subject" does not exclude an individual that is normal in all respects.

"Vertebrates" include fish, reptiles, amphibians, birds (avians), and mammals. "Mammals" include, but are not limited to, murines, simians, humans, farm animals, sport animals, and pets. Mammals may be egg-laying, or they may be marsupials or placentals. "Birds" include, but are not limited to, farm animals, sport animals, and pets.

Cross-Linking Groups for Protein or Nucleic Acid Conjugation

In addition to a compound of Formula (I) or Formula (IIA-B) or Formula (IIIA-B), other cross-linking groups may be used in the methods disclosed herein. Cross-linking groups are categorized based on their chemical reactivities and other properties (see Chemistry of Crosslinking, Thermo Fisher Scientific, https://www.thermofisher.com/us/en/home/life-science/protein-biology/protein-biology-learning-center/protein-biology-resource-library/pierce-proteinmethods/chemistry-crosslinking.html). Cross-linking groups for protein conjugation include, but are not limited to, carboxyl-to-amine reactive groups (e.g., carbodiimide, EDC/EDAC, DCC, N-hydroxysuccinimide [NHS], sulfo-N-hydroxysuccinimide [sulfo-NHS], amine-biotin reagents), amine-reactive groups (e.g., NHS ester, sulfo-NHS ester, sulfotetraflurophenyl-STP, imidoester, pentafluorophenyl ester, hydroxymethyl phosphine), sulfhydryl-reactive groups (e.g., maleimide, haloacetyle [bromo-, iodo-], pyridyldisulfide, thiosulfonate, vinylsulfone), aldehyde-reactive groups (i.e., oxidized sugars/carbonyls; e.g., hydrazide, aldoxyamine), photoreactive groups (i.e., nonselective/random insertion; e.g., diazirine, aryl azide), chemoselective ligation groups (e.g., Staudinger reagent pairs), and hydroxyl (nonaqueous)-reactive groups (e.g., isocyanate). Typically, cross-linking groups are selected based on factors including chemical specificity, spacer arm length, water-solubility, cell membrane permeability, and/or presence of spontaneously reactive or photoreactive groups. They may be homobifunctional (i.e., having identical reactive groups at each end of a spacer arm [e.g., disuccinimidyl suberate (DSS)]) or heterobifunctional (i.e., having different reactive groups at each end of a spacer arm [e.g., sulfosuccinimidyl-4-(N-maleimidomethyl)cyclohexane-1-carboxylate (sulfo-SMCC)]).

Carbodiimides, including N-hydroxysuccinimide and sulfo-N-hydroxysuccinimide (sulfo-NHS), are zero-length crosslinkers resulting in direct conjugation of carobxylates (—COOH) to primary amines ($—NH_2$) without becoming part of the final crosslining amide bond between the target molecules. Sulfo-NHS is a water soluble analog of NHS.

NHS-esters are reactive groups formed by activation of carboxylate molecules. Frequently, they react with primary amines in mildly alkaline conditions (pH 7.2-8.5), resulting in stable amide bonds and releasing N-hydroxysuccinimide, which is removed, e.g., by dialysis or desalting. Sulfo-NHS esters contain a sulfonate ($—SO_3$) group on the N-hydroxysuccinimide ring. Their hydrophilicity inhibits their permeation of cell membranes and allows them to be used for cell surface applications.

Labeling of biomolecules can be performed using activated esters, such as N-hydroxysuccinimide (NHS—) esters and other activated esters (including, but not limited to, sulfo-NHS, sulfotetrafluorophenyl-STP, imidoesters). These reactive compounds can be used for the modification of primary amine groups ($—NH_2$). Modifications can include fluorescent labels, fluorescence quenchers, and other reporter groups. Some embodiments include the attachment of an alkyne group or azido group. Activated esters can be used to modify proteins and peptides, as well as amino-oligonucleotides, amino-modified DNA, and amino-containing sugars. With respect to peptides and proteins, these groups are found at the N-terminus of each polypeptide chain or in the side-chain of lysine (Lys, K) amino acid residues. Because they are usually positively charged at physiological pH, peptide or protein configuration at physiological pH would typically place them on the outside surface of the tertiary structure, and their nucleophilic character would make them targets for conjugation.

Solvents for labeling can include, but are not limited to, water, dimethyl sulfoxide (DMSO), or dimethyl formamide (DMF). Non-sulfonated NHS-esters may need to be dissolved in a water-miscible organic solvent (e.g., DMSO, DMF) prior to addition to a reaction mixture, while sulfo-NHS esters are more water soluble. Preferably, reactions buffers, such as phosphate-buffered saline (PBS) are used that do not contain primary amines, while buffers with primary amines (e.g., Tris, glycine) can be used as quenching buffers.

The dibenzocyclooctyne group (DBCO; azadibenzocyclooctyne [ADIBO]; dibenzoazacyclooctyne [DIBAC]) is a cycloalkyne that is thermally stable and has a high sepcific reactivity toward azide groups through strain-romoted click chemistry reaction (Cu(I)-free Strain-Promoted Alkyne-Azide Click Chemistry [SPAAC]) in the absence of a catalyst (e.g., copper) or reducing agents (e.g., DTT) (See Prim et al., ADIBO-Based “Click” Chemistry for Diagnostic Peptide Micro-Array Fabrication: Physicochemical and Assay Characteristics, Molecules 18:9833.) Ligation occurs quickly and can yield stable triazoles. At physiological pH, the DBCO group does not react with amines or hydroxyls. Dibenzocyclooctyne-N-hydroxysuccinimide ester (DBCO-NHS ester) has a 6-carbon spacer arm, which holds the DBCO moiety close to the tagged molecule, and a terminal carboxylic acid activated as NHS ester, which can react with free amine groups to form a stable amide bond. It interacts with primary amines (N-terminus or lysine side chain) or with aminosilane-coated surfaces. DBCO can be used to label oligomers and other nucleotides at the 5' end.

DBCO-containing modification reagents include, but are not limited to, dibenzylcyclooctyne acids (e.g., dibenzylcyclooctyne acid [DBCO acid], DBCO-lc-acid, dibenzylcyclooctyne-C6-acid); dibenzylcyclooctyne amines (e.g., dibenzylcyclooctyne amine [DBCO amine]); dibenzylcyclooctyne-N-hydroxysuccinimide esters (dibenzylcyclooctyne-N-hydroxysuccinimide ester [DBCO-NHS-ester]; dibenzylcyclooctyne-sulfo-N-hydroxysuccinimide ester [DBCO-sulfo-NHS-ester]; DBCO-lc-NIH ester; dibenzylcyclooctyne-C6-NHS ester [DBCO-C6-NHS ester]; sulfo-dibenzylcyclooctyne-NHS-ester sodium salt [sulfo-DBCO-NHS-ester sodium salt]; dibenzylcyclooctyne-polyethylene glycol4-N-hydroxysuccinimide ester [DBCO-PEG4-NHS ester]; dibenzylcyclooctyne-PEG4-NHS ester; dibenzylcyclooctyne-S—S—NHS ester [DBCO-S—S—NHS ester]); dibenzylcyclooctyne melimides (e.g., dibenzylcyclooctyne-maleimide [DBCO-maleimide]); and dibenzylcyclooctyne-polyethylene glycol-4-maleimides (dibenzylcyclooctyne-polyethylene glycol-4-maleimide [DBCO-PEG4-maleimide]).

Detection Methods

In various aspects, provided herein are methods of detecting or locating a target in a biological sample. Targets are detected by contacting a biological sample with a target detection reagent, e.g., a single-stranded nucleic acid or a fragment thereof, and a labeling reagent. The presence or absence of targets are detected by the presence or absence of the labeling reagent, and the location of the labeling reagent indicates where the target biomolecules were located. In some instances, the biological sample is contacted with the target detection reagent and the labeling reagent concurrently e.g., the detection reagent is a primary antibody and the labeling reagent is a fluorescent dye both of which are conjugated to a single nucleic acid strand. Alternatively, the biological sample is contacted with the target detection reagent and the labeling reagent sequentially, e.g., the detection reagent is a primary antibody and the labeling reagent includes a secondary antibody. For example, the biological sample is incubated with the detection reagent, in some cases together with the labeling reagent, under conditions that allow a complex between the detection reagent (and labeling reagent) and target to form. After complex formation the biological sample is optionally washed one or more times to remove unbound detection reagent (and labeling reagent). When the biological sample is further contacted with a labeling reagent that specifically binds the detection reagent that is bound to the target, the biological sample can optionally be washed one or more times to remove unbound labeling reagent. The presence or absence of the target, and if present its location, in the biological sample is then determined by detecting the labeling reagent.

Imaging technologies for transcriptional profiling of expanded complex tissues include, but are not limited to, confocal microscopy or super-resolution microscopy of RNA in situ hybridization targets, e.g., via ExM in combination with RNA fluorescence in situ hybridization (FISH) and RNA hybridization chain reaction (HCR), as described above.

The methods described herein provide for the detection of multiple targets in a sample.

Multiple targets are identified by contacting the biological sample with additional detection reagents followed by additional labeling reagent specific for the additional detection reagents using the methods described above. For example, each target is associated with a probe comprising a single-stranded nucleic acid (e.g., DNA) with a sequence specific or barcode for that target RNA of interest (e.g., an mRNA). The probes optionally comprises a detectable label. To detect multiple targets simultaneously, a plurality of probes, each recognizing a corresponding unique sequence of one or more RNA targets of interest. The plurality of probes can be added sequentially (with removal of the previous priors prior to addition of the next one) or simultaneously. Alternatively, a different probe can be added to each distinct well in an array on a multiwell format plate or to each spot on a microarray.

HCR is conducted with first and second nucleic acid hairpin molecules (e.g., single-stranded DNA) at least one of which has a detectable label. In some cases, sets or subsets of labeled hairpin molecules are prepared with distinct labels, e.g., fluorophores that are distinguished by their emission spectra, e.g., one that emits in the green spectra and one that emits in the red spectra. The pairs (sets) of labeled hairpin molecules can then be added simultaneously to a biological sample to detect multiple targets at once. Alternatively, sets or subsets of labeled hairpin molecules are prepared with the same label. Each set of the labeled hairpin molecules can then be added sequentially to detect a specific target, with each set of labeled hairpin molecules removed from the biological sample prior to adding the next set of labeled hairpin molecules to detect multiple targets sequentially.

The detection moiety, i.e., detectable label, is a substance used to facilitate identification and/or quantitation of a target. Detection moieties are directly observed or measured or indirectly observed or measured. Detection moieties include, but are not limited to, radiolabels that can be measured with radiation-counting devices; pigments, dyes or other chromogens that can be visually observed or measured with a spectrophotometer; spin labels that can be measured with a spin label analyzer; and fluorescent moieties, where the output signal is generated by the excitation of a suitable molecular adduct and that can be visualized by excitation with light that is absorbed by the dye or can be measured with standard fluorometers or imaging systems, for example. The detection moiety can be a luminescent substance such as a phosphor or fluorogen; a bioluminescent substance; a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The detection moiety may also take the form of a chemical or biochemical, or an inert particle, including but not limited to colloidal gold, microspheres, quantum dots, or inorganic crystals such as nanocrystals or phosphors. The term detection moiety or detectable label can also refer to a "tag" or hapten that can bind selectively to a labeled molecule such that the labeled molecule, when added subsequently, is used to generate a detectable signal. For instance, one can use biotin, iminobiotin or desthiobiotin as a tag and then use an avidin or streptavidin conjugate of horseradish peroxidase (HRP) to bind to the tag, and then use a chromogenic substrate (e.g., tetramethylbenzidine) or a fluorogenic substrate such as Amplex Red or Amplex Gold (Molecular Probes, Inc.) to detect the presence of HRP. Similarly, the tag can be a hapten or antigen (e.g., digoxigenin), and an enzymatically, fluorescently, or radioactively labeled antibody can be used to bind to the tag. Numerous labels are known by those of skill in the art and include, but are not limited to, particles, fluorescent dyes, haptens, enzymes and their chromogenic, fluorogenic, and chemiluminescent substrates, and other.

A fluorophore is a chemical moiety that exhibits an absorption maximum beyond 280 nm, and when covalently attached in a labeling reagent retains its spectral properties. Fluorophores include, without limitation; a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a borapolyazaindacene, a xanthene, an oxazine or a benzoxazine, a carbazine, a phenalenone, a coumarin, a benzofuran and benzphenalenone and derivatives thereof. As used herein, oxazines include resorufins, aminooxazinones, diaminooxazines, and their benzo-substituted analogs.

When the fluorophore is a xanthene, the fluorophore may be a fluorescein, a rhodol, or a rhodamine. As used herein, fluorescein includes benzo- or dibenzofluoresceins, seminaphthofluoresceins, or naphthofluoresceins. Similarly, as used herein rhodol includes seminaphthorhodafluors. Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position. Fluorophores include xanthene (rhodol, rhodamine, fluorescein and derivatives thereof) coumarin, cyanine, pyrene, oxazine and borapolyazaindacene. In addition, the fluorophore can be sulfonated xanthenes, fluorinated xanthenes, sulfonated coumarins, fluorinated coumarins and sulfonated cyanines. The choice of the fluorophore in the labeling reagent will determine the absorption and fluorescence emission properties of the labeling reagent. Physical properties of a fluorophore label include spectral characteristics (absorption, emission and stokes shift), fluorescence intensity, lifetime, polarization and photo-bleaching rate all of which can be used to distinguish one fluorophore from another.

Typically, a fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

Preferably the detection moiety is a fluorescent dye. Fluorescent dyes include, for example, Fluorescein, Rhodamine, Texas Red, Cγ2, Cγ3, Cγ5, Cγ0, Cγ0.5, Cγ1, Cγ1.5, Cγ3.5, Cγ7, VECTOR Red, ELF™ (Enzyme-Labeled Fluorescence), FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-(6-(7-nitrobenz-2-oxa-1,3-diazol-4-yl)amino) caproyl) (NBD), BODIPY™, boron dipyrromethene difluoride, Oregon Green, MITOTRACKER™ Red, DiOC7 (3), DiIC18, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

Many fluorophores can also function as chromophores.

In addition to fluorophores, enzymes also find use as detectable moieties. Enzymes are desirable detectable moieties because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. This is advantageous where there is a low quantity of target present in the sample or a fluorophore does not exist that will give comparable or stronger signal than the enzyme. However, fluorophores are most preferred because they do not require additional assay steps and thus reduce the overall time required to complete an assay. The enzyme substrate is selected to yield the preferred measurable product, e.g., colorimetric, fluorescent or chemiluminescence. Such substrates are extensively used in the art.

A preferred colorimetric or fluorogenic substrate and enzyme combination uses oxidoreductases such as horseradish peroxidase and a substrate such as 3,3'-diaminobenzidine (DAB) and 3-amino-9-ethylcarbazol-e (AEC), which yield a distinguishing color (brown and red, respectively). Other colorimetric oxidoreductase substrates that yield detectable products include, but are not limited to, 2,2-azino-bis(3-ethylbenzothiaz-oline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplexe Red reagent and its variants and reduced dihydroxanthenes, including dihydrofluoresceins and dihydrorhodamines including dihydrorhodamine 123. Peroxidase substrates that are tyramides represent a unique class of peroxidase substrates in that they can be intrinsically detectable before action of the enzyme but are "fixed in place" by the action of a peroxidase in a process described as tyramide signal amplification (TSA). These substrates are extensively utilized to label targets in samples that are cells, tissues, arrays, or microarrays for their subsequent detection by microscopy, flow cytometry, optical scanning and fluorometry.

Additional colorimetric (and in some cases fluorogenic) substrate and enzyme combination use a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy4-methylcoumarinyl phosphate (DiFMUP) fluorescein diphosphate, 3-0-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates.

Glycosidases, in particular β-galactosidase, β-glucuronidase and β-glucosidase, are additional suitable enzymes. Appropriate colorimetric substrates include, but are not limited to, 5-bromo4-chloro-3-indolyl β-D-galactopyranoside (X-gal) and similar indolyl galactosides, glucosides, and glucuronides, o-nitrophenyl β-D-galactopyranoside (ONPG) and p-nitrophenyl β-D-galactopyranosid-e. Preferred fluorogenic substrates include resorufin β-D-galactopyranoside, fluorescein digalactoside (FDG), fluorescein diglucuronide and their structural variants, 4-methylumbelliferyl β-D-galactopyranoside, carboxyumbelliferyl β-D-galactopyranoside and fluorinated coumarin β-D-galactopyranosides.

Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful. For example, the enzyme is luciferase or aequorin. The substrates are luciferine, ATP, $Ca^{++}$ and coelenterazine.

In addition to enzymes, haptens such as biotin are useful detectable moieties. Biotin is useful because it can function in an enzyme system to further amplify a detectable signal, and it can function as a tag to be used in affinity chromatography for isolation purposes. For detection purposes, an enzyme conjugate that has affinity for biotin is used, such as avidin-HRP. Subsequently a peroxidase substrate is added to produce a detectable signal.

Haptens also include hormones, naturally occurring and synthetic drugs, pollutants, allergens, affector molecules, growth factors, chemokines, cytokines, lymphokines, amino acids, peptides, chemical intermediates, or nucleotides.

In some cases, a detectable moiety is a fluorescent protein. Exemplary fluorescent proteins include green fluorescent protein (GFP), the phycobiliproteins and the derivatives thereof, luciferase or aequorin. The fluorescent proteins, especially phycobiliprotein, are particularly useful for creating tandem dye labeled labeling reagents. These tandem dyes comprise a fluorescent protein and a fluorophore for the purposes of obtaining a larger stokes shift where the emission spectra is farther shifted from the wavelength of the fluorescent protein's absorption spectra. This is particularly advantageous for detecting a low quantity of a target in a sample where the emitted fluorescent light is maximally optimized, in other words little to none of the emitted light is reabsorbed by the fluorescent protein. For this to work, the fluorescent protein and fluorophore function as an energy transfer pair where the fluorescent protein emits at the wavelength that the fluorophore absorbs at and the fluorphore then emits at a wavelength farther from the fluorescent proteins than could have been obtained with only the fluorescent protein. A particularly useful combination is phycobiliproteins and sulforhodamine fluorophores, or the sulfonated cyanine fluorophores; or the sulfonated xanthene derivatives. Alternatively, the fluorophore functions as the energy donor and the fluorescent protein is the energy acceptor.

Methods of Visualizing the Detection Moiety Depends on the Label

In some cases, the sample is illuminated with a light wavelength selected to give a detectable optical response, and observed with means for detecting the optical response. Equipment that is useful for illuminating fluorescent compounds described herein includes, but is not limited to, hand-held ultraviolet lamps, mercury arc lamps, xenon lamps, lasers and laser diodes. These illumination sources are optically integrated into laser scanners, fluorescent microplate readers or standard or microfluorometers. The degree and/or location of signal, compared with a standard or expected response, indicates whether and to what degree the sample possesses a given characteristic or desired target.

The optical response is optionally detected by visual inspection, or by use of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

When an indirectly detectable label is used then the step of illuminating typically includes the addition of a reagent that facilitates a detectable signal such as colorimetric enzyme substrate. Radioisotopes are also considered indirectly detectable wherein an additional reagent is not required but instead the radioisotope must be exposed to X-ray film or some other mechanism for recording and measuring the radioisotope signal. This can also be true for some chemiluminescent signals that are best observed after expose to film.

As used herein, "specificity" refers to the ability of an antibody to discriminate between antigenic determinants. It also refers to the determinants recognized by a particular receptor or antibody. It also refers to the ability of a receptor to discriminate between substrates, such as drugs. With respect to nucleic acids, it refers to identity or complementarity as a function of competition or recognition/binding, respectively. "Specificity" of recognition or binding may be affected by the conditions under which the recognition or binding takes place (e.g., pH, temperature, salt concentration, and other factors known in the art).

An "effective amount" is an amount sufficient to affect beneficial or desired results. An effective amount may be administered one or more times to achieve the beneficial or desired result.

As used in the specification and claims, the singular forms "a," "an," and "the" include plural references unless the context dictates otherwise. For example, the term "a molecule" can also include a plurality of molecules.

When not otherwise stated, "substantially" means "being largely, but not wholly, that which is specified." The term "about" or "approximately" means within an acceptable error range for the particular value as determined by one of ordinary skill in the art, which will depend in part on how the value is measured or determined, i.e., limitations of the measurement system. For example, "about" can mean within 1 or more than 1 standard deviations, per practice in the art. Alternatively, when referring to a measurable value such as an amount, a temporal duration, a concentration, and the like, may encompass variations of ±20% or ±10%, more preferably ±5%, even more preferably ±1%, and still more preferably ±0.1% from the specified value, as such variations are appropriate to perform the disclosed methods.

Synthesis of Compounds Disclosed Herein.

As will be shown in the examples herein, in one embodiment, a compound of Formula (I) may be synthesized by the following route:

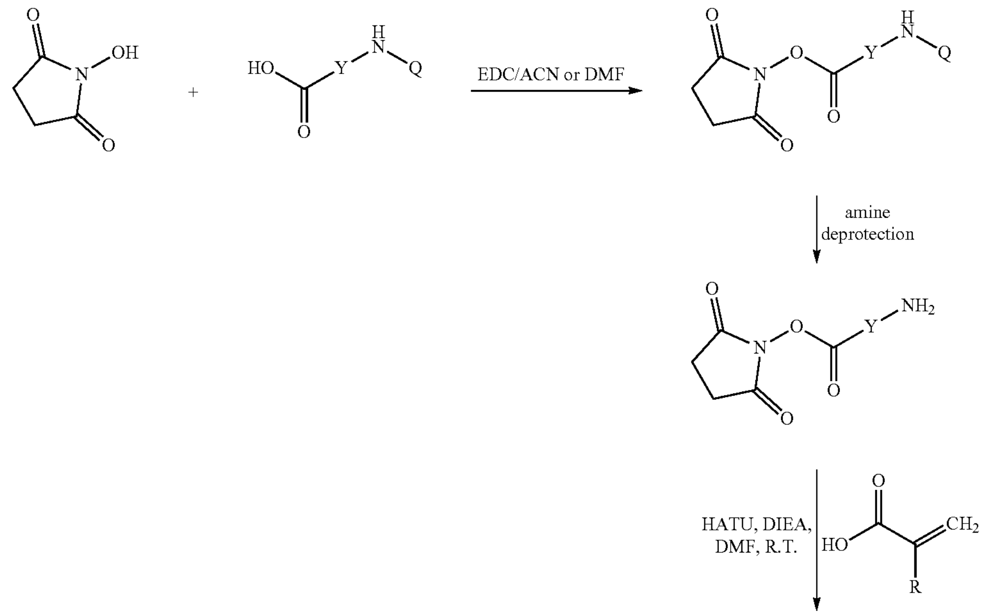

-continued

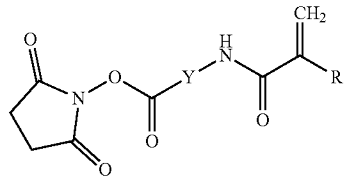

I

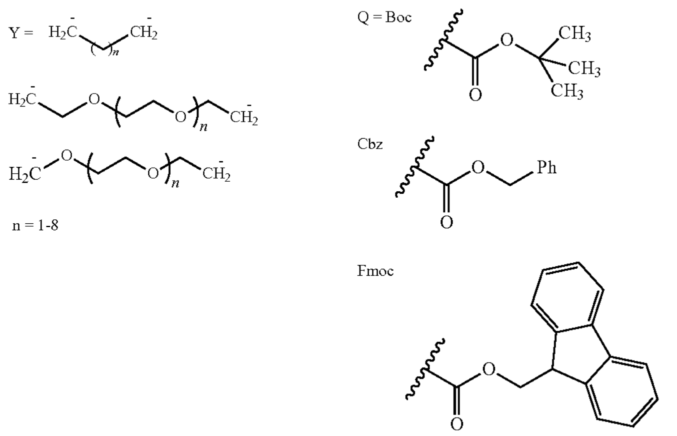

wherein the definitions of Y, Q and n are shown in the above scheme; and R may be selected from hydrogen, deuterium, halo, —CN, —$NO_2$, and an optionally substituted aliphatic, alicyclic, heteroaliphatic, heterocyclic, aromatic, acyl or heteroaromatic group.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl. In some embodiments, R is formyl (methanoyl), acetyl (ethanoyl), propanoyl, butanoyl, propenoyl (acryloyl), or butenoyl (crotonyl).

In some embodiments, acyl is formyl or acetyl.

Other protecting groups in addition to Boc, Cbz and Fmoc may be used.

Non-limiting examples of optional substitutions of R include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Such methods for the synthesis of compounds of Formula (I) are embraced herein. Examples 3-12 show synthetic routes for compounds I-1 through I-10.

In some embodiments, a compound of Formula IIA may be prepared by the following route.

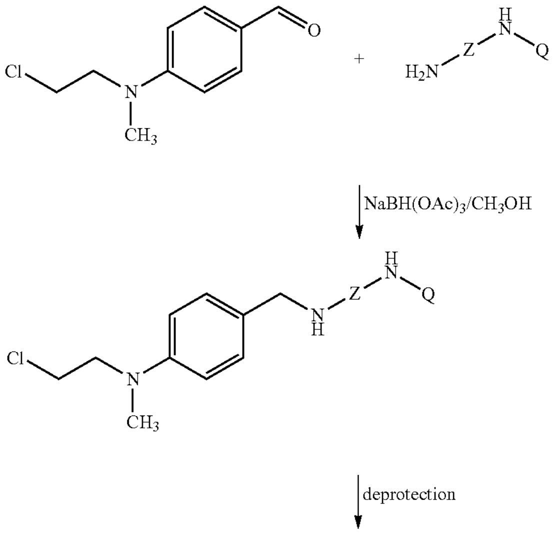

-continued

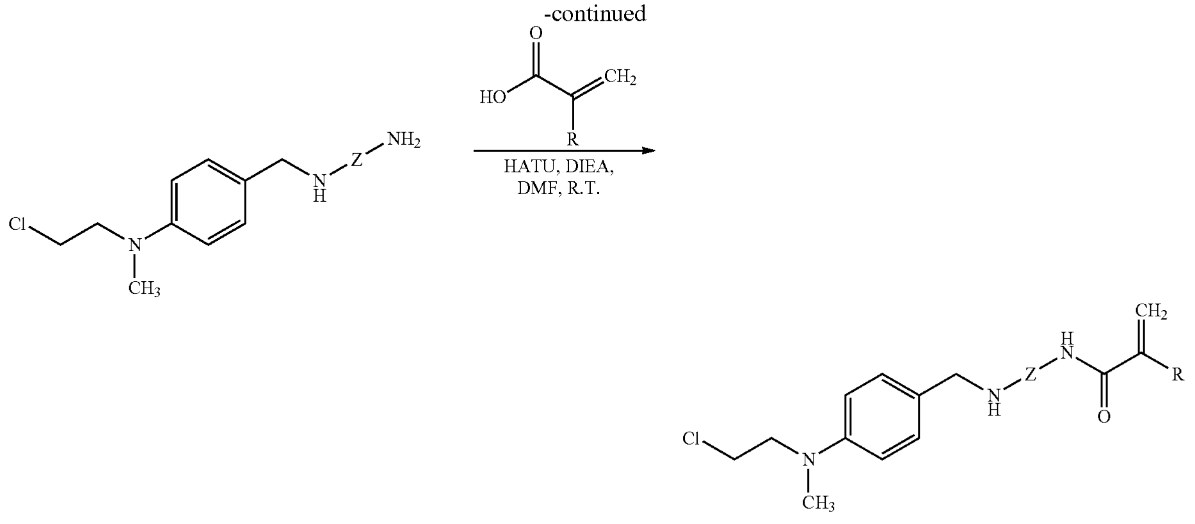

IIA

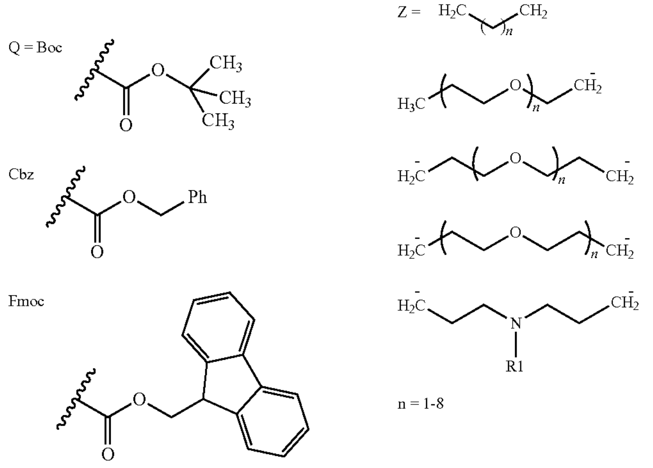

wherein the definitions of Z, Q and n are shown in the above scheme; R is selected from hydrogen, deuterium, halo, —CN, —$NO_2$, and an optionally substituted aliphatic, alicyclic, heteroaliphatic, heterocyclic, aromatic, acyl or heteroaromatic group; and $R^1$ is H, alkyl, acyl or allyl.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiments, $R^1$ is H. In some embodiments, $R^1$ is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, $R^1$ is allyl. In some embodiments, $R^1$ is formyl (methanoyl), acetyl (ethanoyl), propanoyl, butanoyl, propenoyl (acryloyl), or butenoyl (crotonyl).

In some embodiments, acyl is formyl or acetyl.

Other protecting groups in addition to Boc, Cbz and Fmoc may be used.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, RIN, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Such methods for the synthesis of compounds of Formula (IIA) are embraced herein. Examples 20-23 show synthetic routes for compounds IIA-1 through IIA-4.

In some embodiments, a compound of Formula IIA may be prepared by the following route.

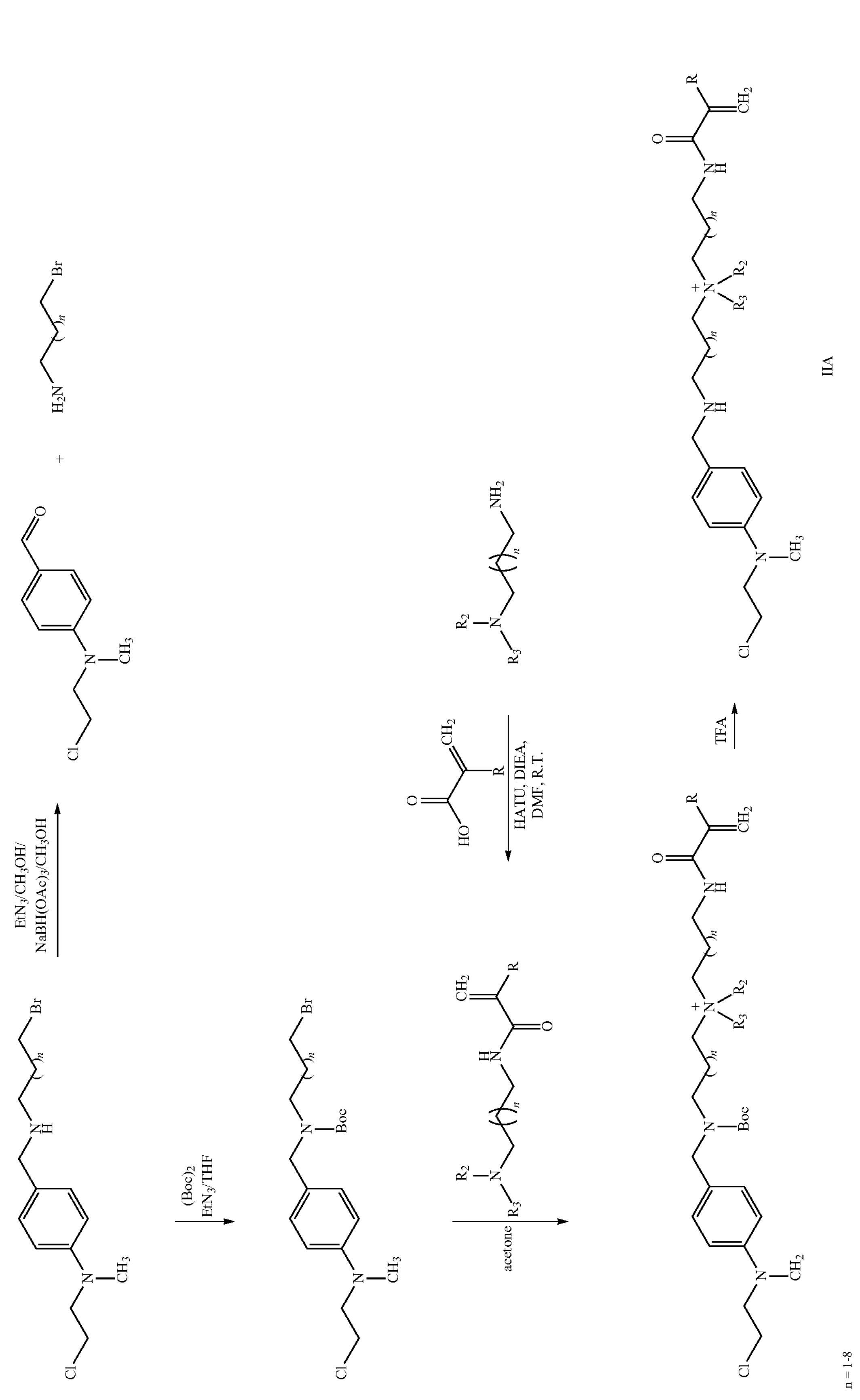
IIA
n = 1-8 wherein each occurrence of n is independently 1-8; R is selected from hydrogen, deuterium, halo, —CN, —$NO^2$, and an optionally substituted aliphatic, alicyclic, heteroaliphatic, heterocyclic, aromatic, acyl or heteroaromatic group; and $R^2$ and $R^3$ are independently selected from H, alkyl, acyl or allyl.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

In some embodiments, $R^2$ or $R^3$ is independently $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R2 or R3 is independently allyl.

In some embodiments, $R^2$ or $R^3$ is independently formyl (methanoyl), acetyl (ethanoyl), propanoyl, butanoyl, propenoyl (acryloyl), or butenoyl (crotonyl).

In some embodiments, acyl is formyl or acetyl.

Such methods for the synthesis of compounds of Formula (IIA) are embraced herein. Examples 24-25 show synthetic routes for compounds IIA-5 through IIA-6.

In some embodiments, a compound of Formula IIB may be prepared by the following route:

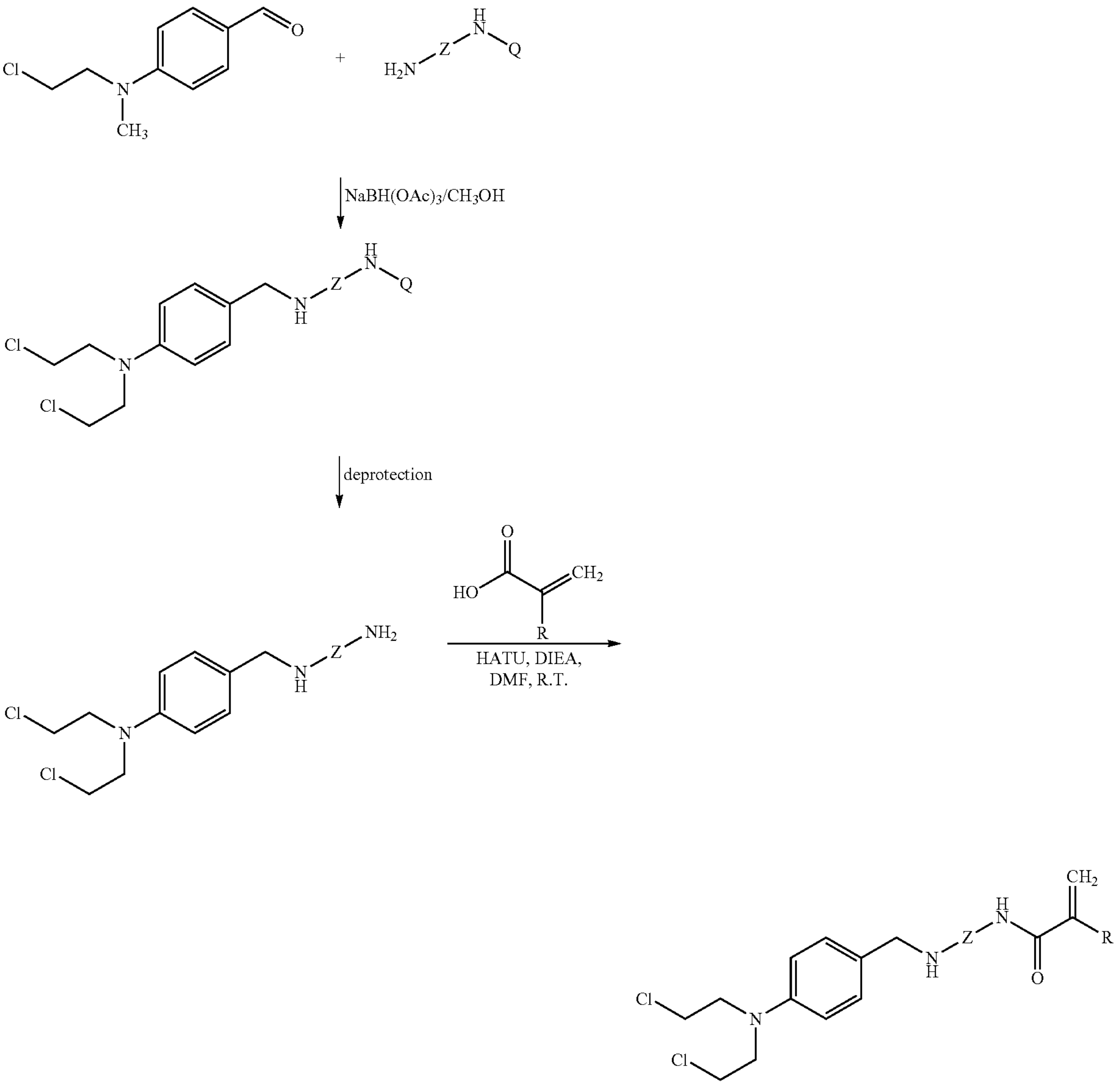

II B

-continued

Q = Boc

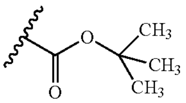

Cbz

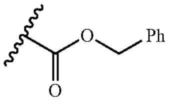

Fmoc

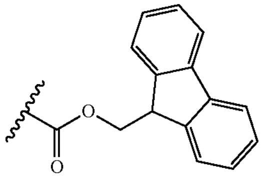

Z =

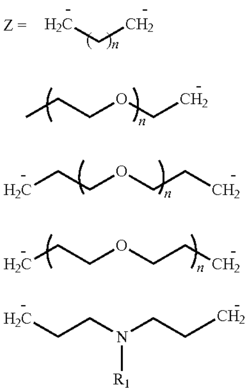

n = 1-8 wherein Z and Q are as defined in the above scheme; R is selected from hydrogen, deuterium, halo, —CN, —$NO_2$, and an optionally substituted aliphatic, alicyclic, heteroaliphatic, heterocyclic, aromatic, acyl or heteroaromatic group; and $R^1$ is H, alkyl, acyl or allyl.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiment, R1 a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R1 is allyl. In some embodiments, R1 is formyl (methanoyl), acetyl (ethanoyl), propanoyl, butanoyl, propenoyl (acryloyl), or butenoyl (crotonyl).

In some embodiments, acyl is formyl or acetyl.

Other protecting groups in addition to Boc, Cbz and Fmoc may be used.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Such methods for the synthesis of compounds of Formula (IIB) are embraced herein. Examples 26-29 show synthetic routes for compounds IIB-1 through IIB-4.

In some embodiments, a compound of Formula IIB may be prepared by the following route:

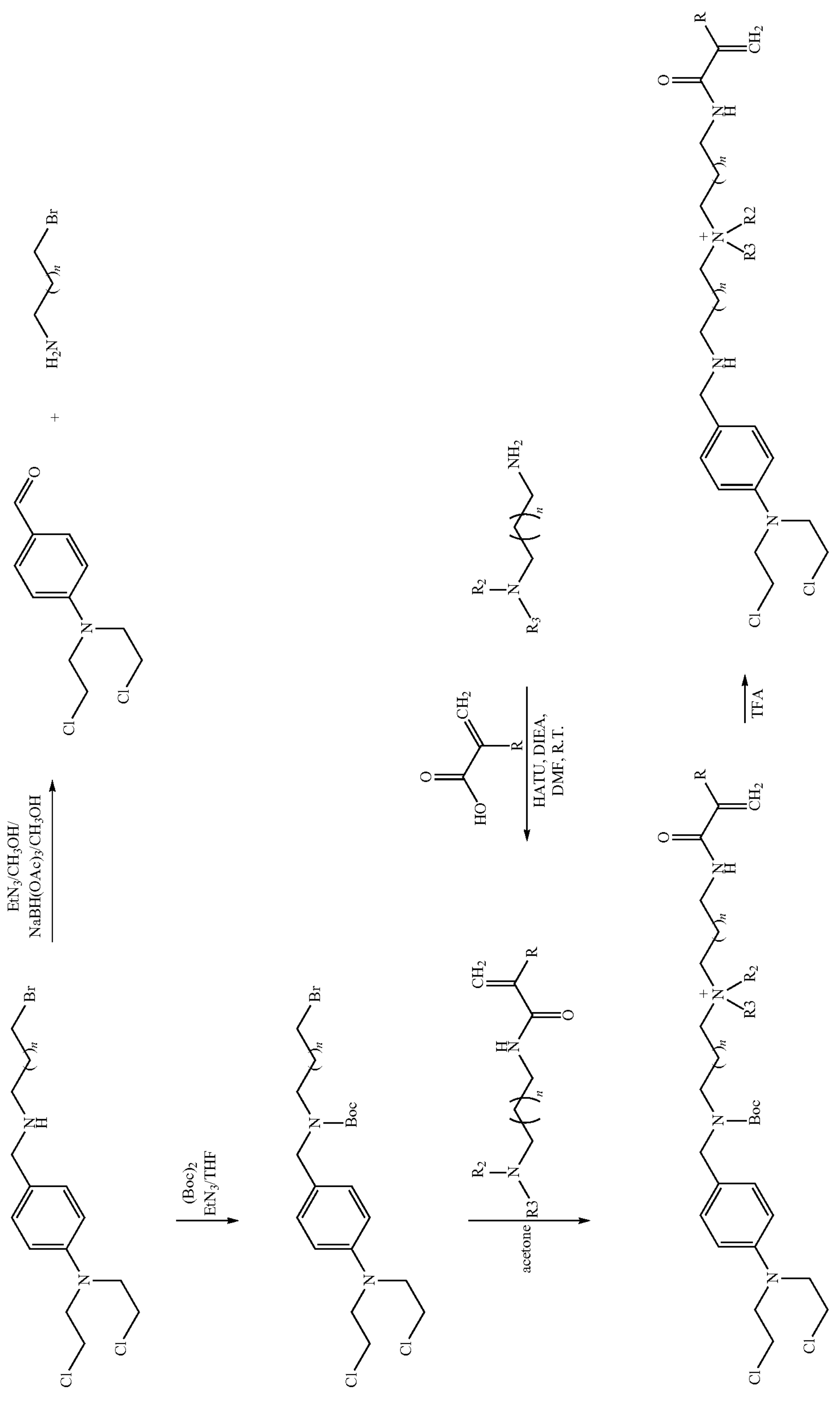
II B
n = 1-8 wherein each occurrence of n is independently 1-8; R is selected from hydrogen, deuterium, halo, —CN, —$NO_2$, and an optionally substituted aliphatic, alicyclic, heteroaliphatic, heterocyclic, aromatic, acyl or heteroaromatic group; and R2 and R3 are independently H, alkyl, acyl or allyl.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiments, R2 and R3 are independently $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R2 or R3 is independently allyl. In some embodiments R2 and R3 are independently formyl (methanoyl), acetyl (ethanoyl), propanoyl, butanoyl, propenoyl (acryloyl), or butenoyl (crotonyl).

In some embodiments, acyl is formyl or acetyl.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Such methods for the synthesis of compounds of Formula (IIB) are embraced herein. Examples 30-31 show synthetic routes for compounds IIB-5 through IIB-6.

In some embodiments, a compound of Formula IIIA may be prepared by the following route.

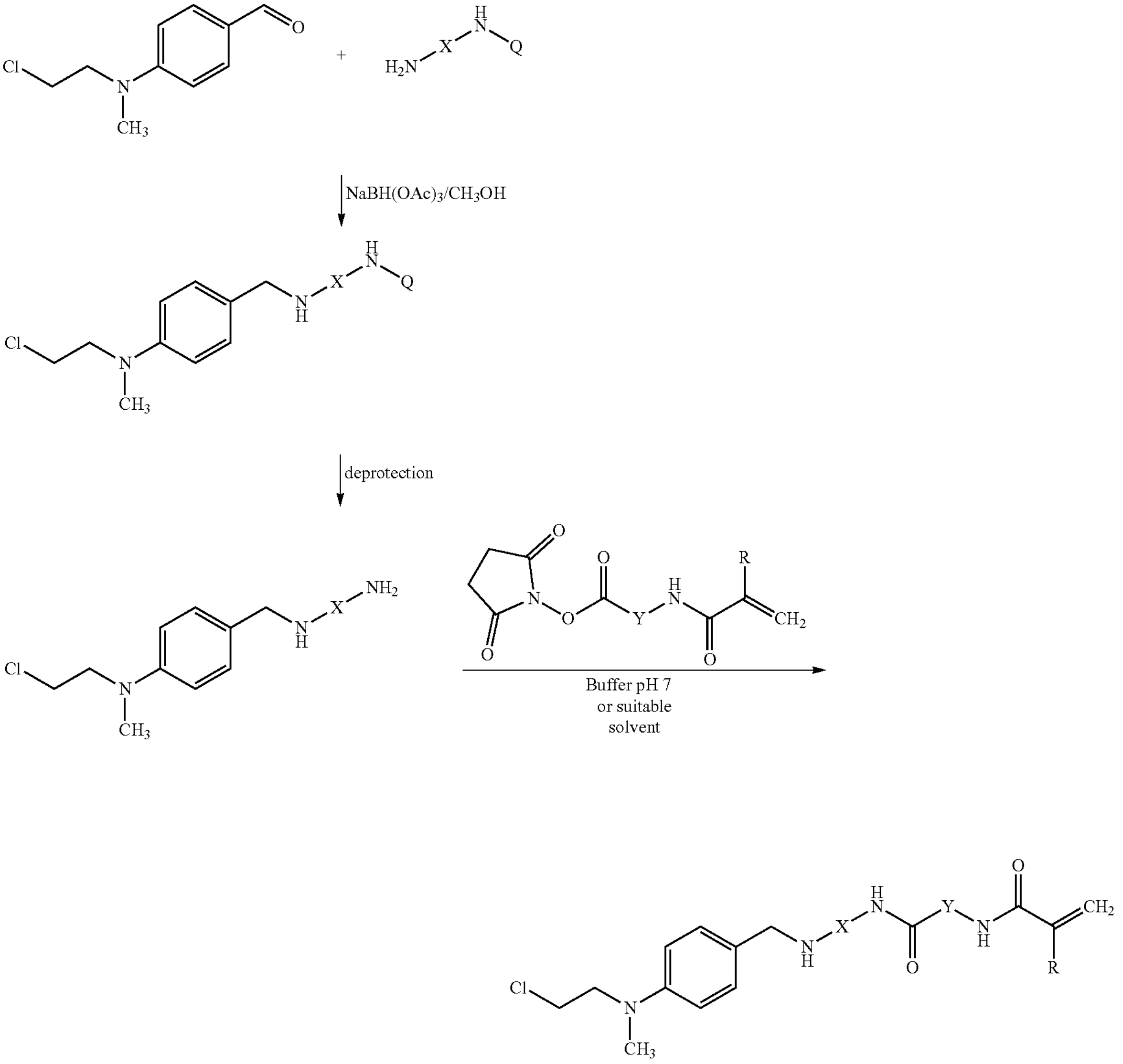

III A

-continued

Q = Boc

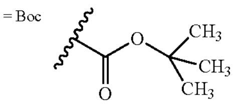

Cbz

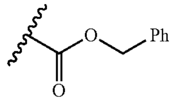

Fmoc

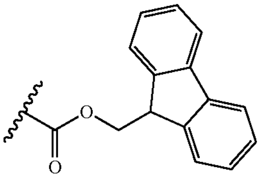

Y =

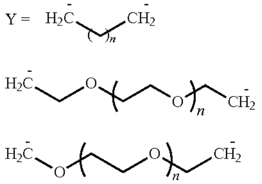

X =

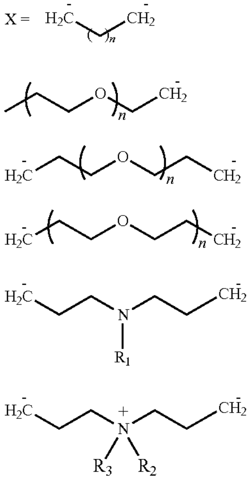

n = 1-8 wherein X, Q, Y and n are as defined above and each n is independently 1-8; R is selected from hydrogen, deuterium, halo, —CN, —$NO_2$, and an optionally substituted aliphatic, alicyclic, heteroaliphatic, heterocyclic, aromatic, acyl or heteroaromatic group; and each occurrence of R1, R2 and R3 are independently selected from H, alkyl, acyl and allyl.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiments, R1, R2 and R3 are independently $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R1, R2 or R3 is allyl.

In some embodiments, R1, R2 and R3 are independently formyl (methanoyl), acetyl (ethanoyl), propanoyl, butanoyl, propenoyl (acryloyl), or butenoyl (crotonyl).

In some embodiments, acyl is formyl or acetyl.

The n in the X moiety and the n in the Y moiety are each independently selected from 1, 2, 3, 4, 5, 6, 7 or 8.

Other protecting groups in addition to Boc, Cbz and Fmoc may be used.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{cc}$, $R^{ff}$, $R^{gg}$, $R^{hh}$, $R^{ii}$, $R^{ij}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Such methods for the synthesis of compounds of Formula (IIIA) are embraced herein. Examples 32-51 show synthetic routes for compounds IIIA-1 through IIIA-20.

In some embodiments, a compound of Formula IIIB may be prepared by the following route:

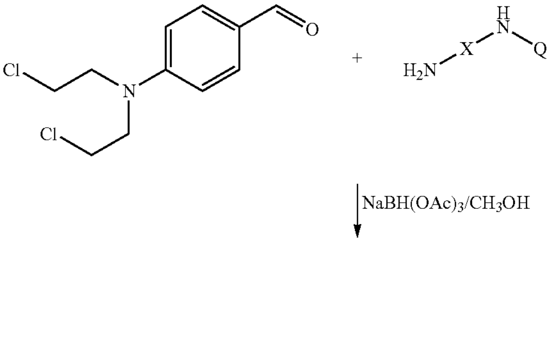

-continued

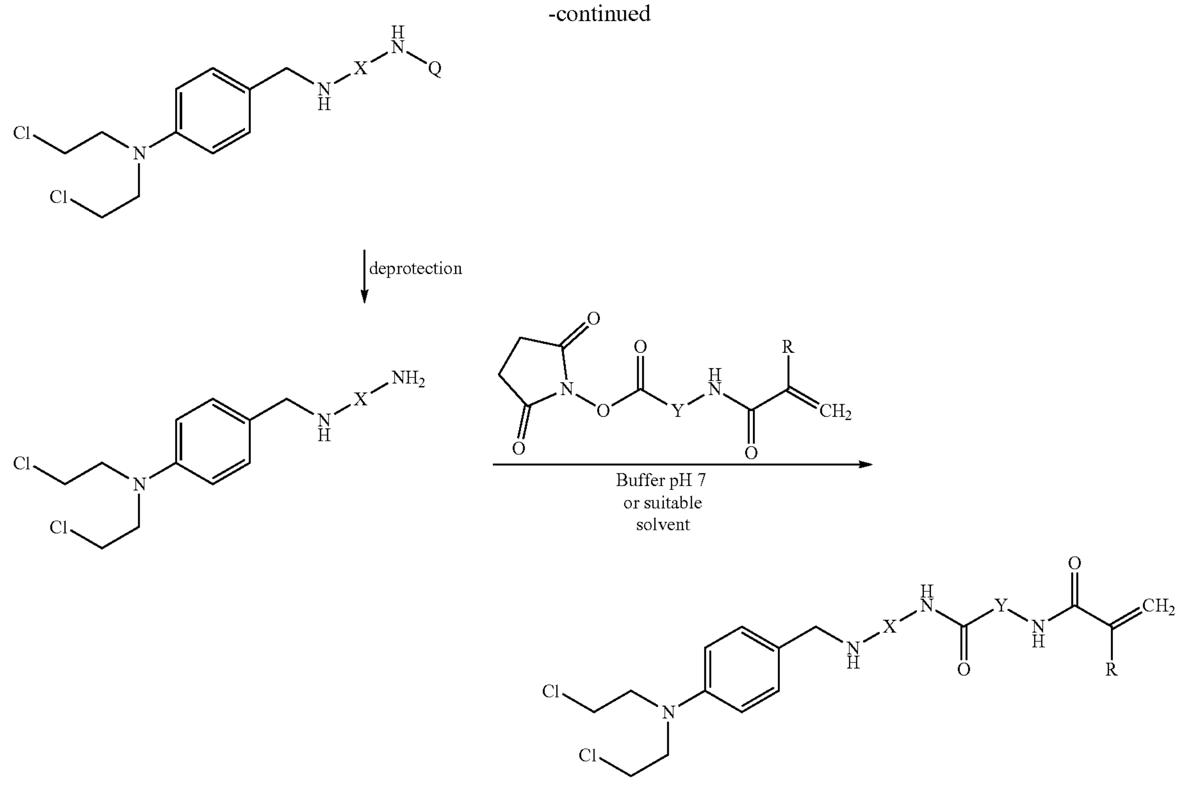

III B

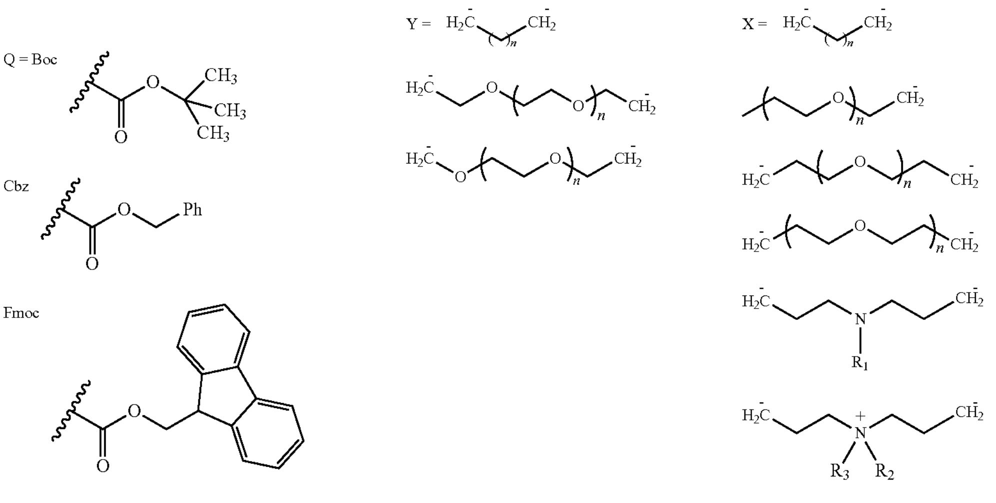

n = 1-8 wherein X, Q, Y and n are as defined above and each n is independently 1-8; R is selected from hydrogen, deuterium, halo, —CN, —$NO_2$, and an optionally substituted aliphatic, alicyclic, heteroaliphatic, heterocyclic, aromatic, acyl or heteroaromatic group; and R1, R2 and R3 are independently H, alkyl, acyl or allyl.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiments, R1, R2 and R3 are independently a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R1, R2 or R3 is allyl.

In some embodiments, $R^2$ and $R^3$ are independently formyl (methanoyl), acetyl (ethanoyl), propanoyl, butanoyl, propenoyl (acryloyl), or butenoyl (crotonyl).

In some embodiments, acyl is formyl or acetyl.

The n in the X moiety and the n in the Y moiety are each independently selected from 1, 2, 3, 4, 5, 6, 7 or 8.

Other protecting groups in addition to Boc, Cbz and Fmoc may be used.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, $-OR^{aa}$, $-NR^{bb}R^{cc}$, $-S(=O)_wR^{dd}$, $-S(=O)_wNR^{ee}R^{ff}$, $-C(=O)R^{gg}$, $-CO_2R^{hh}$, $-CONR^{ii}R^{jj}$, $-NR^{kk}CONR^{ll}R^{mm}$, $-OCONR^{nn}R^{oo}$, or $-NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, $-NO_2$, —OH, $-CH_2F$, $-CHF_2$, $-CF_3$, $-OCH_3$, $-OCH_2F$, $-OCHF_2$, $-OCF_3$, $-NH_2$, $-NHCH_3$, $-N(CH_3)_2$, $-CO_2H$, —SH, $-S(O)_wCH_3$, or an aliphatic, alicyclic, heteroaliphatic, heterocyclic, aromatic, or heteroaromatic; and w is 0, 1, or 2.

Such methods for the synthesis of compounds of Formula (IIIB) are embraced herein. Examples 52-71 show synthetic routes for compounds IIIB-1 through IIIB-20.

Examples

Example 1. Synthetic Methods

The practitioner has a well-established literature of small molecule chemistry to draw upon, in combination with the information contained herein, for guidance on synthetic strategies, protecting groups, and other materials and methods useful for the synthesis of the compounds of this disclosure.

The various references cited herein provide helpful background information on preparing compounds similar to the inventive compounds described herein or relevant intermediates, as well as information on formulation, uses, and administration of such compounds which may be of interest.

Moreover, the practitioner is directed to the specific guidance and examples provided in this document relating to various exemplary compounds and intermediates thereof.

The compounds of this disclosure and their preparation can be understood further by the examples that illustrate some of the processes by which these compounds are prepared or used. It will be appreciated, however, that these examples do not limit the disclosure. Variations of the disclosure, now known or further developed, are considered to fall within the scope of the present disclosure as described herein and as hereinafter claimed.

According to the present disclosure, any available techniques can be used to make or prepare the inventive compounds or compositions including them. For example, a variety of solution phase synthetic methods such as those discussed in detail below may be used. Alternatively or additionally, the inventive compounds may be prepared using any of a variety combinatorial techniques, parallel synthesis and/or solid phase synthetic methods known in the art.

It will be appreciated as described below, that a variety of inventive compounds can be synthesized according to the methods described herein. The starting materials and reagents used in preparing these compounds are either available from commercial suppliers such as Aldrich Chemical Company (Milwaukee, WI), Bachem (Torrance, CA), Sigma (St. Louis, MO), or are prepared by methods well known to a person of ordinary skill in the art following procedures described in such references as Fieser and Fieser 1991, "Reagents for Organic Synthesis", vols 1-17, John Wiley and Sons, New York, NY, 1991; Rodd 1989 "Chemistry of Carbon Compounds", vols. 1-5 and supps, Elsevier Science Publishers, 1989; "Organic Reactions", vols 1-40, John Wiley and Sons, New York, NY, 1991; March 2001, "Advanced Organic Chemistry", 5th ed. John Wiley and Sons, New York, NY; and Larock 1990, "Comprehensive Organic Transformations: A Guide to Functional Group Preparations", $2^{nd}$ ed. VCH Publishers. These schemes are merely illustrative of some methods by which the compounds of this disclosure can be synthesized, and various modifications to these schemes can be made and will be suggested to a person of ordinary skill in the art having regard to this disclosure.

The starting materials, intermediates, and compounds of this disclosure may be isolated and purified using conventional techniques, including filtration, distillation, crystallization, chromatography, and the like. They may be characterized using conventional methods, including physical constants and spectral data.

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance (NMR) or by high-pressure liquid chromatography (HPLC), of a suitably worked up sample of the reaction mixture.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent (e.g., ethyl acetate, dichloromethane, diethyl ether). The desired product containing extracts were washed appropriately with water followed by a saturated solution of brine. On occasions where the product containing extract was deemed to contain residual oxidants, the extract was washed with a 10% solution of sodium sulphite in saturated aqueous sodium bicarbonate solution, prior to the aforementioned washing procedure. On occasions where the product containing extract was deemed to contain residual acids, the extract was washed with saturated aqueous sodium bicarbonate solution, prior to the aforementioned washing procedure (except in those cases where the desired product itself had acidic character). On occasions where the product containing extract was deemed to contain residual bases, the extract was washed with 10% aqueous citric acid solution, prior to the aforementioned washing procedure (except in those cases where the desired product itself had basic character). Post washing, the desired product containing extracts were dried over anhydrous magnesium sulphate, and then filtered. The crude products were then isolated by removal of solvent(s) by rotary evaporation under reduced pressure, at an appropriate temperature (generally less than 45° C.).

General Purification Procedures:

Unless mentioned specifically, chromatographic purification refers to flash column chromatography on silica and/or preparative thin layer chromatography (TLC) plates, using a single solvent or mixed solvent as eluent. Suitably purified desired product containing elutes were combined and concentrated under reduced pressure at an appropriate temperature (generally less than 45° C.) to constant mass. Final compounds were dissolved in 50% aqueous acetonitrile, filtered and transferred to vials, then freeze-dried under high vacuum before submission for biological testing.

Example 2. General Synthesis of Compounds of Formula (I).

The following synthetic route may be used to prepare compounds of Formula (I).

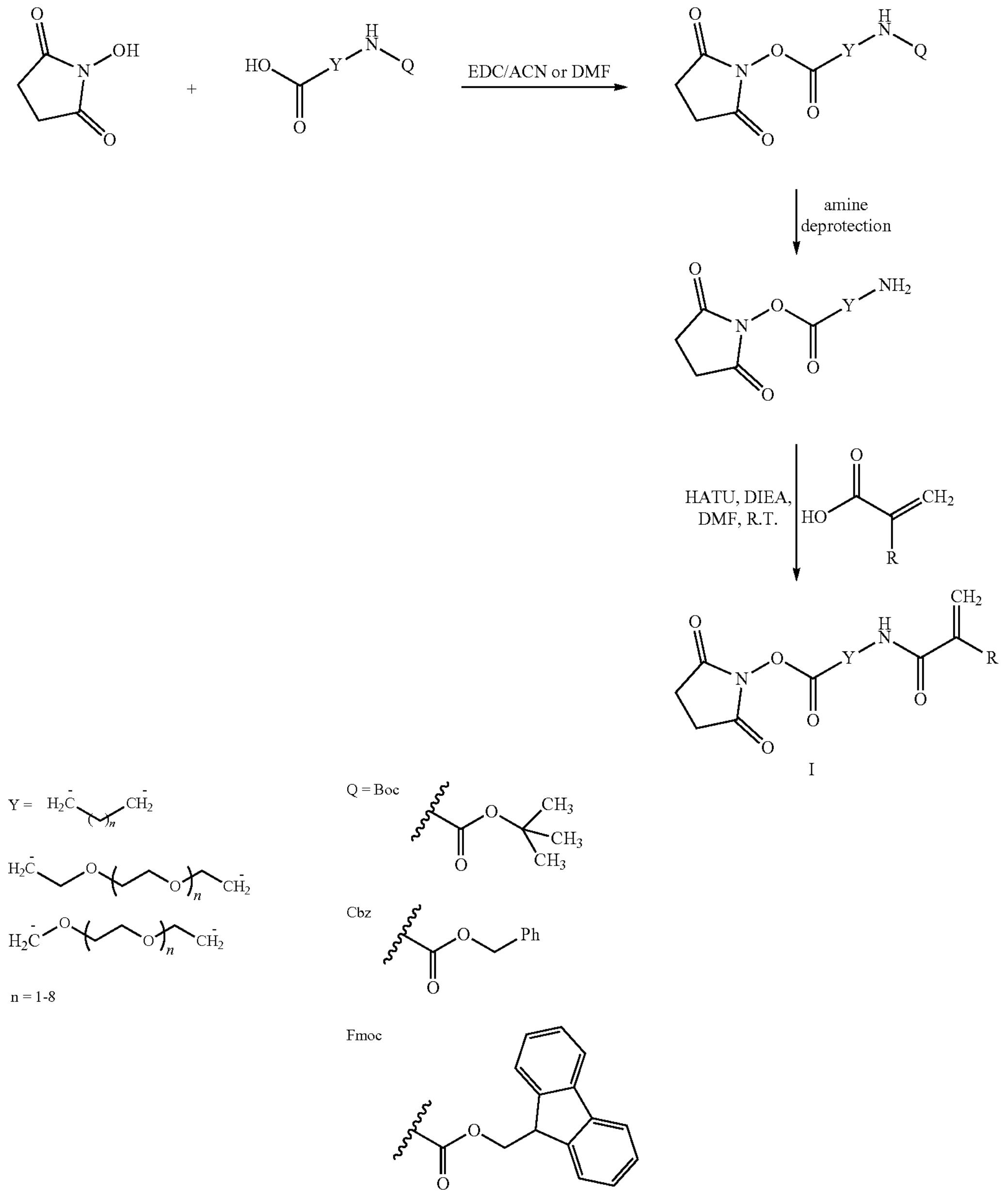

wherein the definitions of Y, Q and n are shown in the above scheme; and R may be selected from hydrogen, deuterium, halo, —CN, —$NO_2$, and an optionally substituted aliphatic, alicyclic, heteroaliphatic, heterocyclic, aromatic, acyl or heteroaromatic group.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiments, acyl is formyl or acetyl.

Other protecting groups in addition to Boc, Cbz and Fmoc may be used.

Non-limiting examples of optional substitutions of R include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wN$-$R^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Example 3. Synthetic Route for Compound I-1
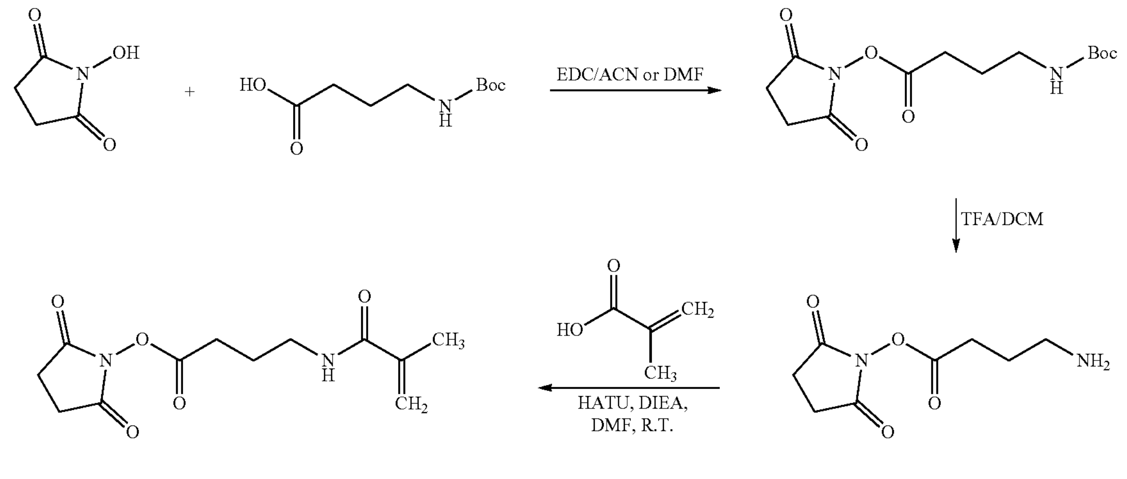
Example 4. Synthetic Route for Compound I-2
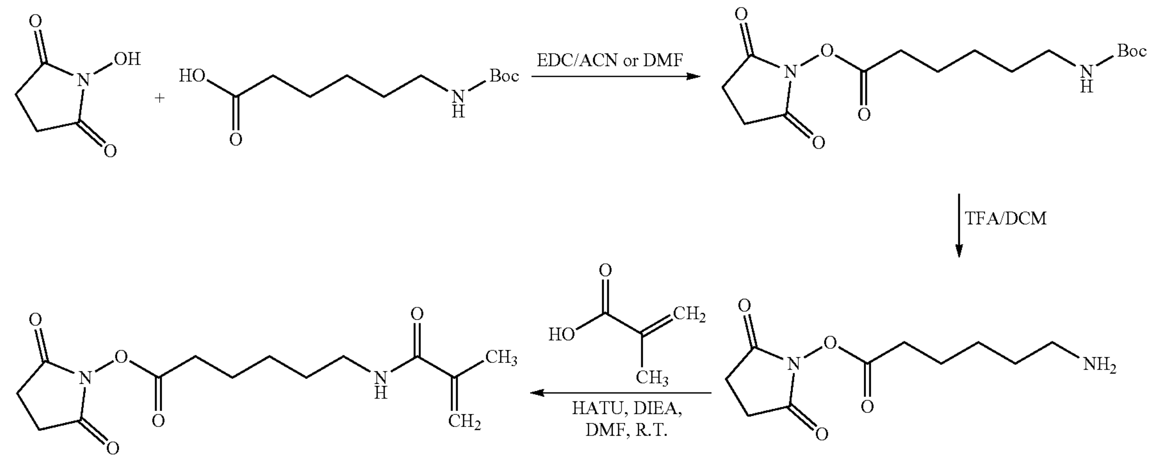
Example 5. Synthetic Route for Compound I-3
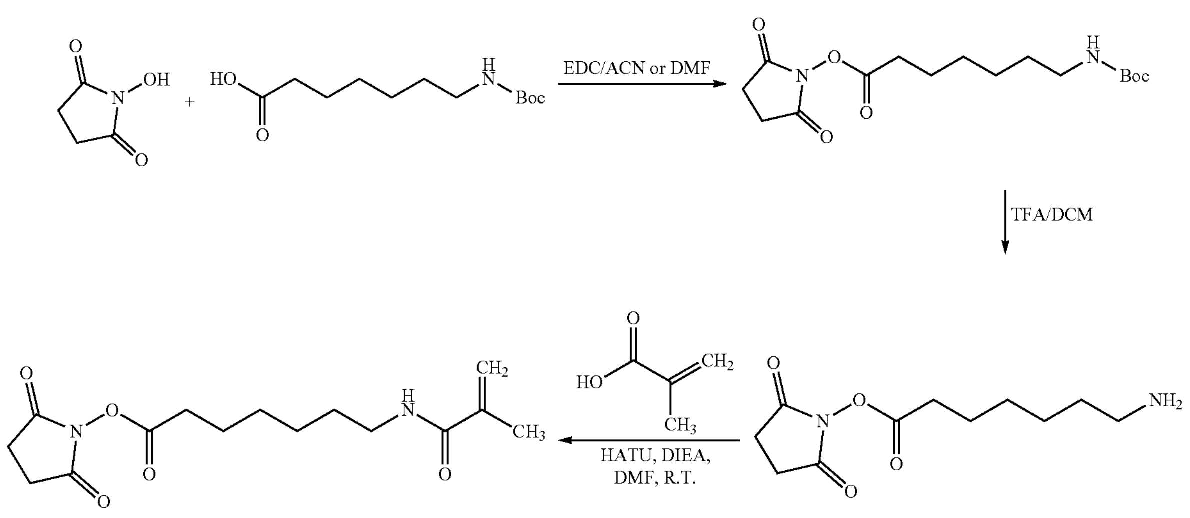

Example 6. Synthetic Route for Compound I-4
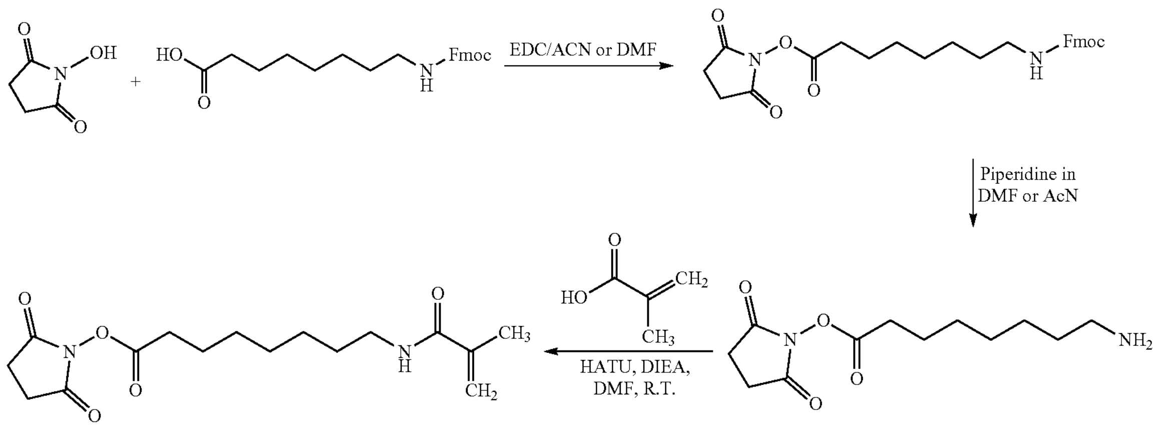
Example 7. Synthetic Route for Compound I-5
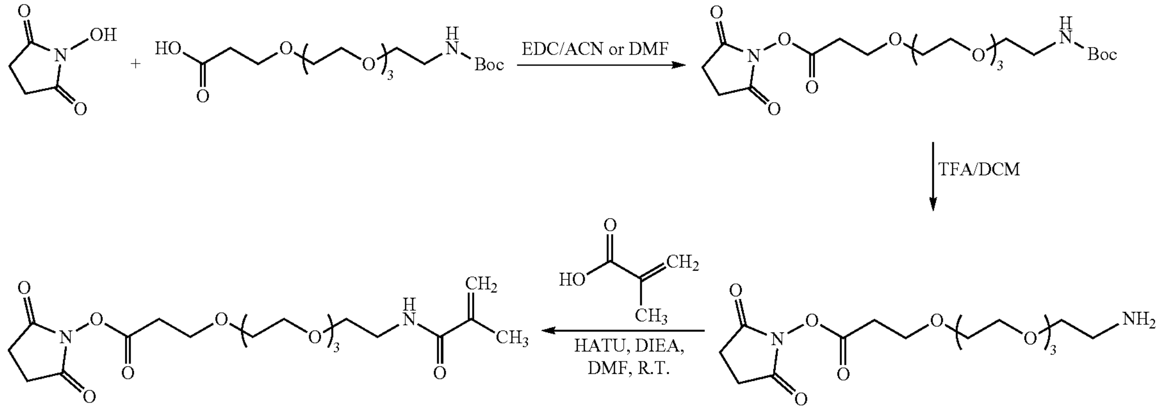
Example 8. Synthetic Route for Compound I-6
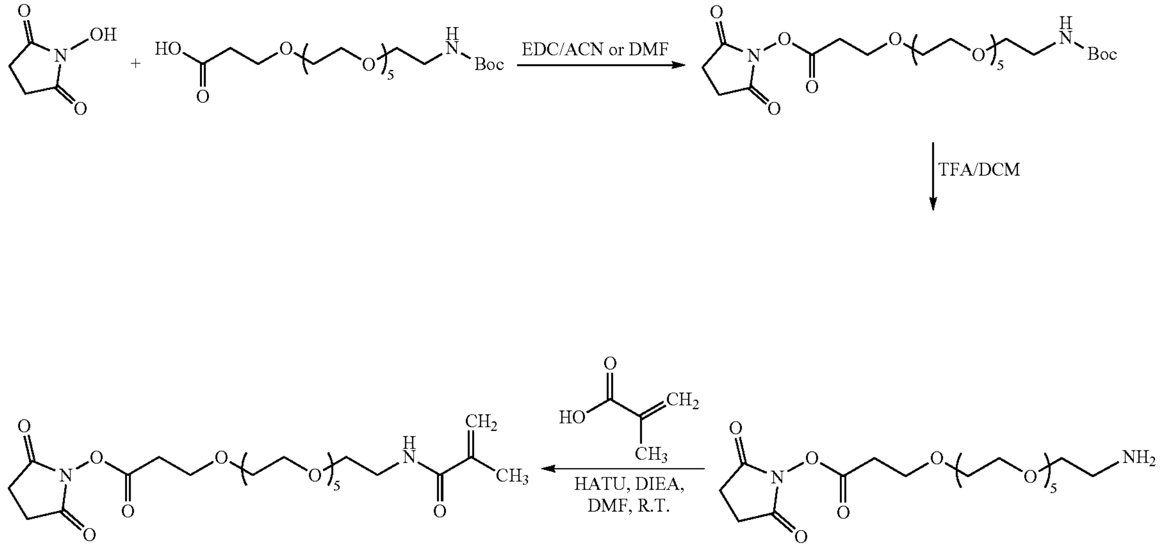

Example 9. Synthetic Route for Compound I-7
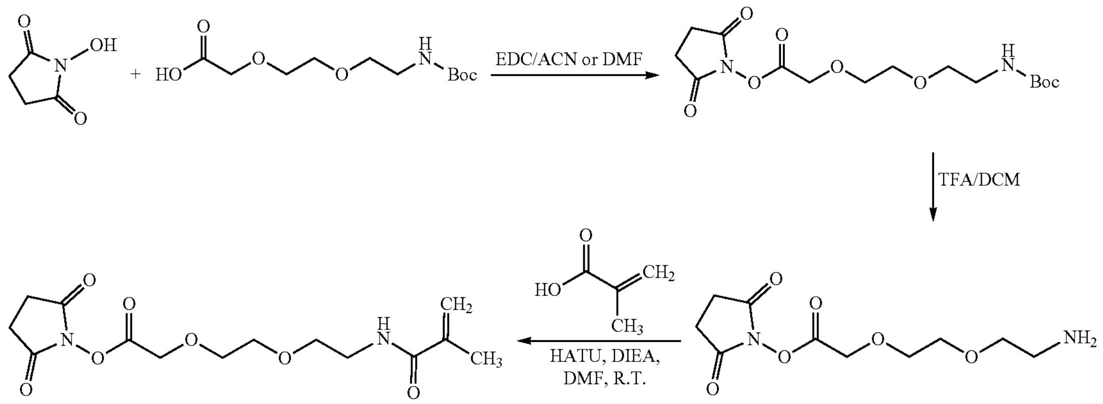
Example 10. Synthetic Route for Compound I-8
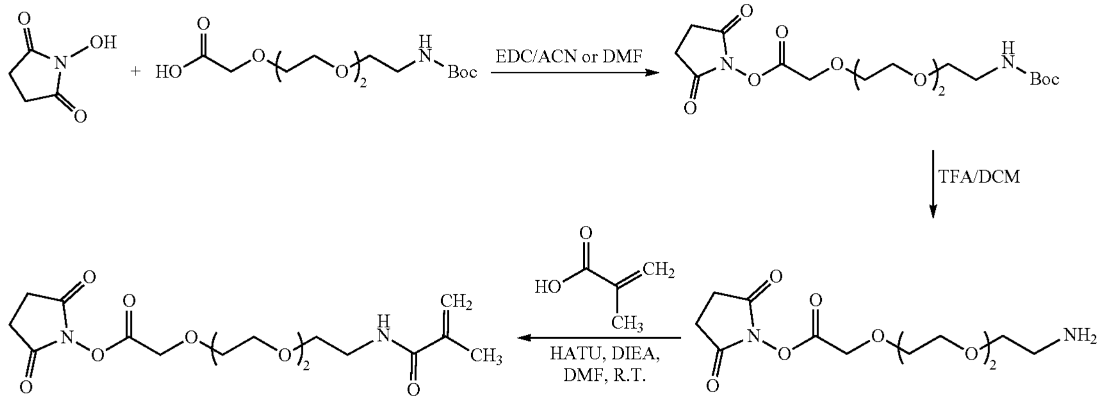
Example 11. Synthetic Route for Compound I-9
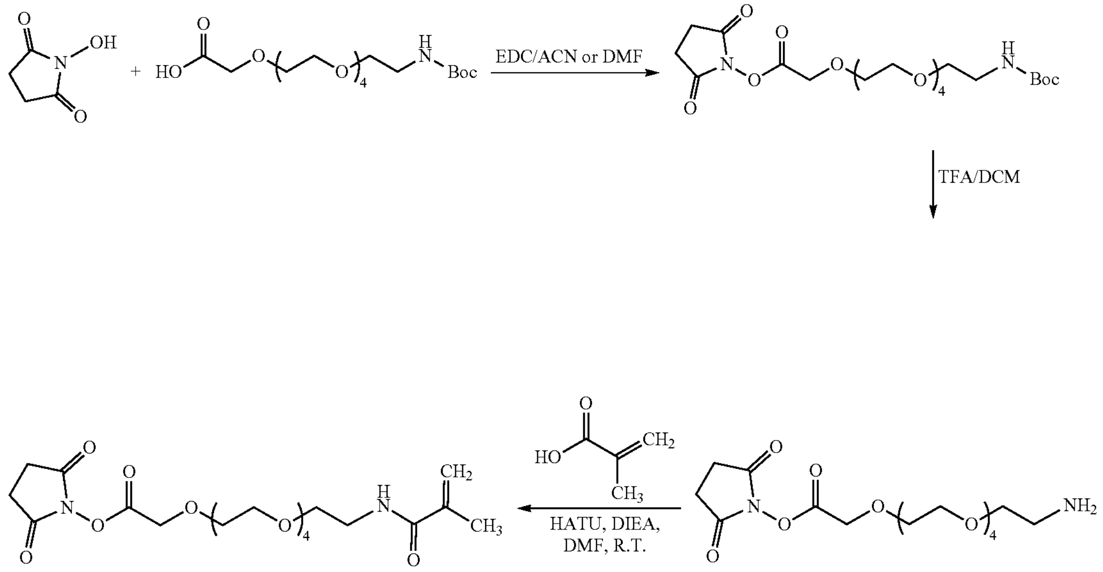

Example 12. Synthetic Route for Compound I-10

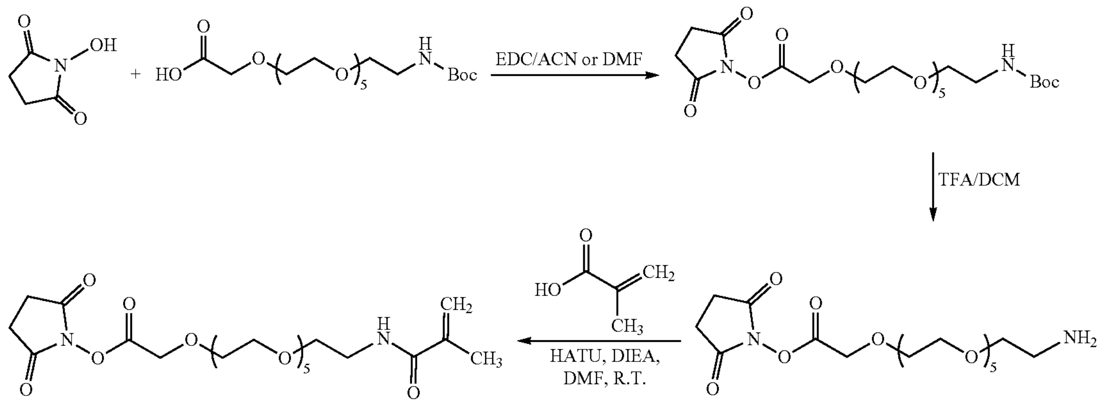

Example 13. Synthetic Route for Compounds of Formulas IIA, IIB, IIIA and IIIB.

The compounds of the formulas shown in the figure below may be prepared by synthetic schemes shown in the ensuing Examples 20-71. The definitions of the substituents are as described elsewhere herein.

II A

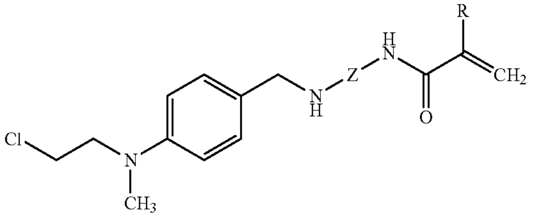

II B

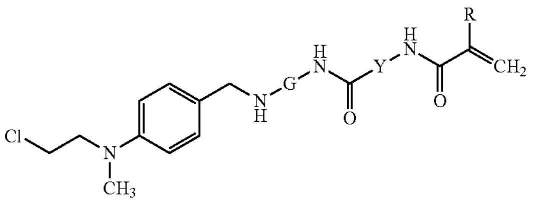

III A

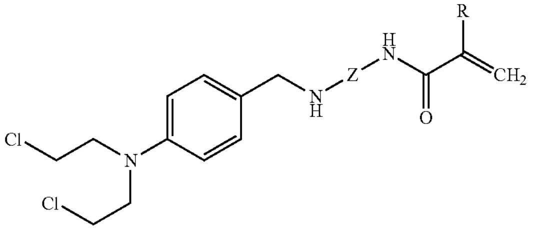

III B

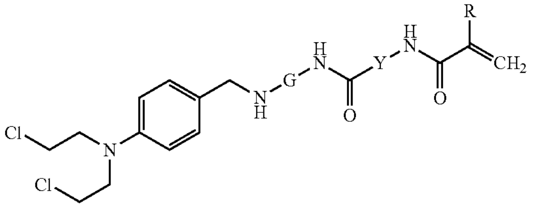

-continued

Z =

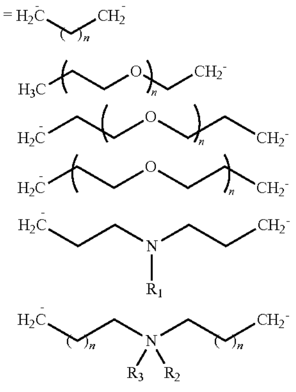

n = 1-8

G =

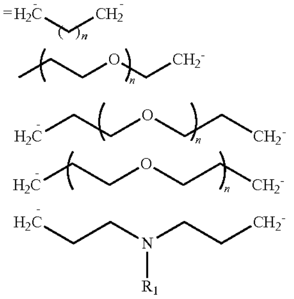

Y =

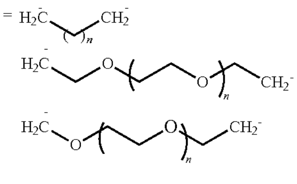

R may be selected from hydrogen, deuterium, halo, —CN, —$NO_2$, and an optionally substituted aliphatic, alicyclic, heteroaliphatic, heterocyclic, aromatic, acyl or heteroaromatic group.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiments, R1, R2 or R3 is independently $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R1, R2 or R3 is independently allyl.

In some embodiments, acyl is formyl or acetyl.

The n in the G moiety and the n in the Z moiety are each independently selected from 1, 2, 3, 4, 5, 6, 7 or 8.

In the Z moiety

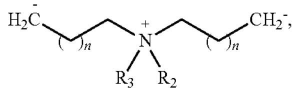

each n is independently selected from 1, 2, 3, 4, 5, 6, 7 or 8; and R3 and R2 are independently selected as described above.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Example 14. Synthetic Route for Compounds of Formula IIA

The scheme shown in the figure below may be used to prepare compounds in Examples 20-23. The definitions of the substituents are as described elsewhere herein.

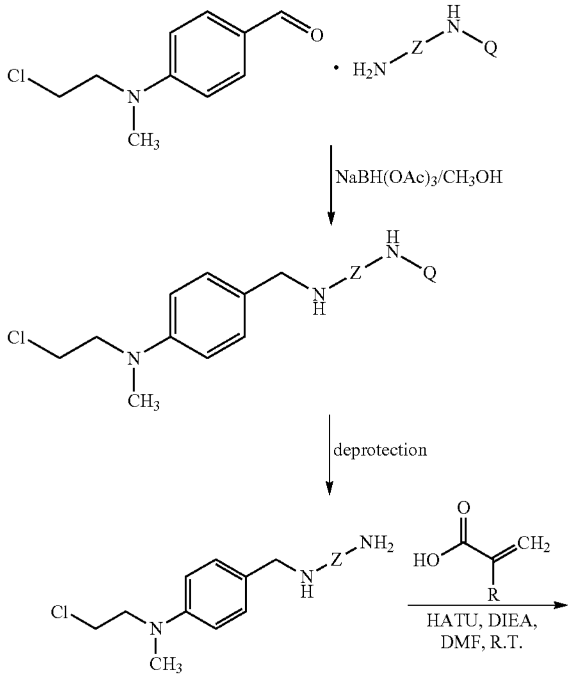

-continued

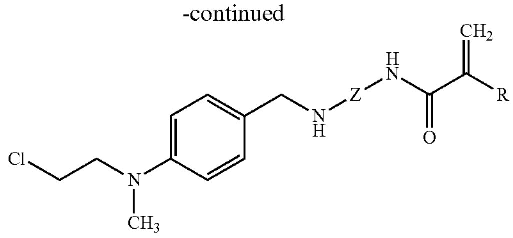

II A

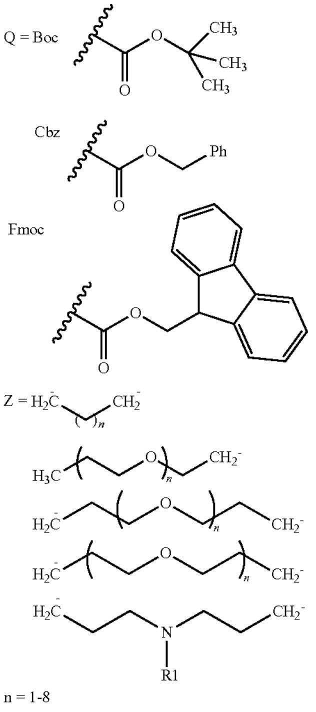

R may be selected from hydrogen, deuterium, halo, —CN, —$NO_2$, and an optionally substituted aliphatic, alicyclic, heteroaliphatic, heterocyclic, aromatic, acyl or heteroaromatic group.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiments, R1 is formyl (methanoyl), acetyl (ethanoyl), propanoyl, butanoyl, propenoyl (acryloyl), or butenoyl (crotonyl).

In some embodiments, acyl is formyl or acetyl.

Other protecting groups in addition to Boc, Cbz and Fmoc may be used.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Example 15. Synthetic Route for Compounds of Formula IIA

The scheme shown in the figure below may be used to prepare compounds in Examples 24-25. The definitions of the substituents are as described elsewhere herein.

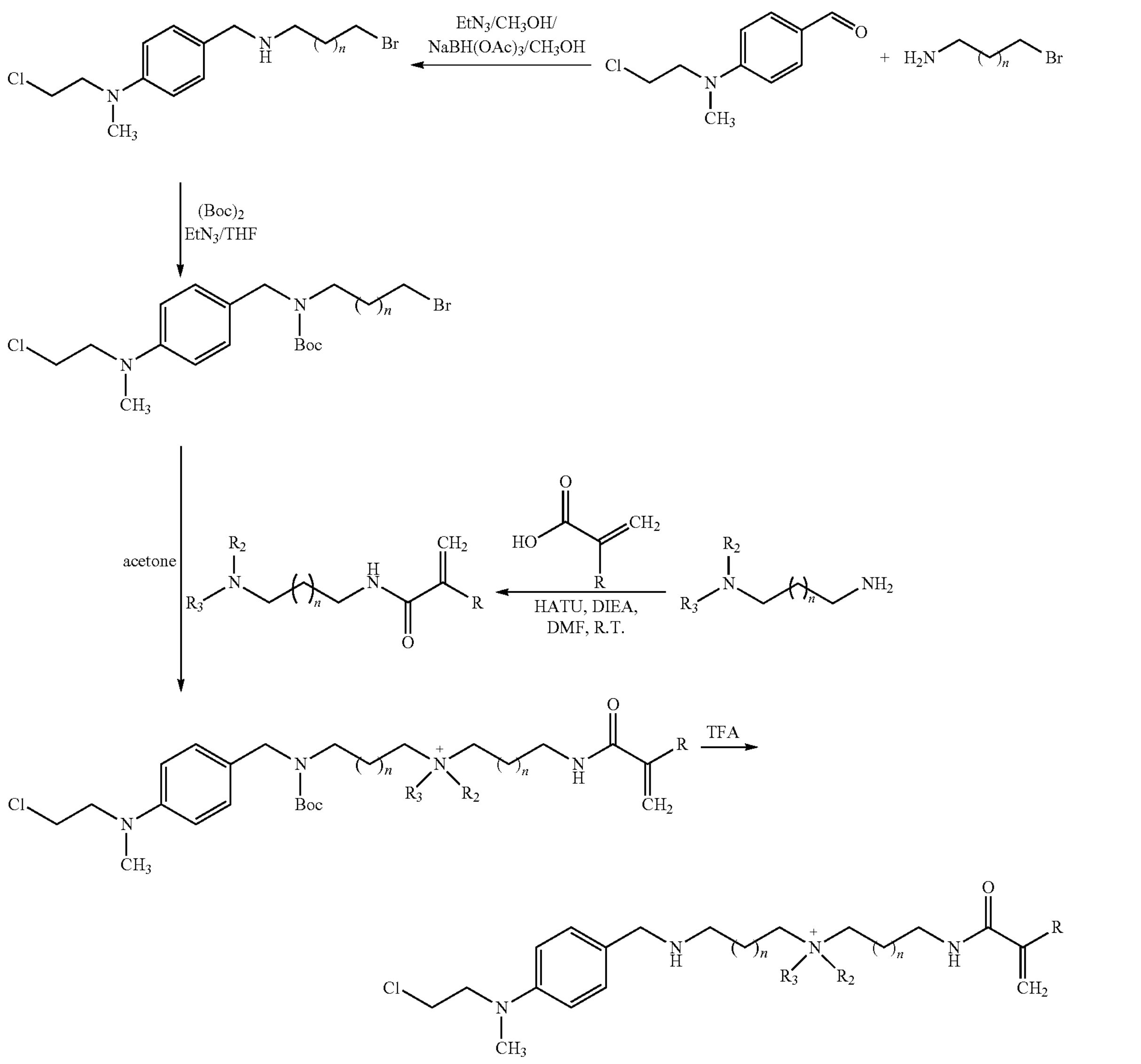

II A n = 1-8

In addition to the above independent selections of each occurrence of n, R may be independently selected from hydrogen, deuterium, halo, —CN, —$NO_2$, and an optionally substituted aliphatic, alicyclic, heteroaliphatic, heterocyclic, aromatic, acyl or heteroaromatic group.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiments, R2 or R3 is independently $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R2 or R3 is independently allyl.

In some embodiments, acyl is formyl or acetyl.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Example 16. Synthetic Route for Compounds of Formula IIB

The scheme shown in the figure below may be used to prepare compounds in Examples 26-29. The definitions of the substituents are as described elsewhere herein.

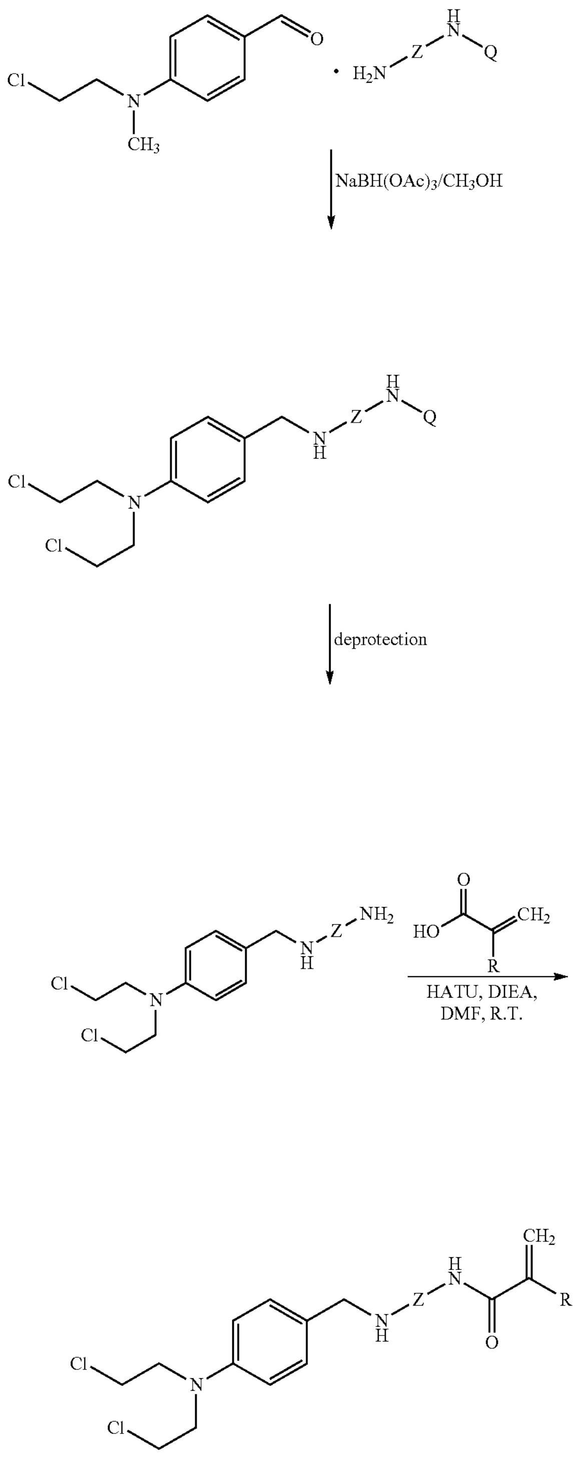

II B

-continued

Q = Boc 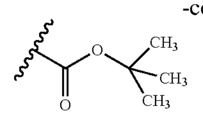

Cbz 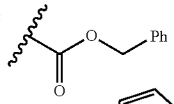

Fmoc 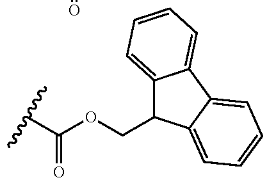

Z = 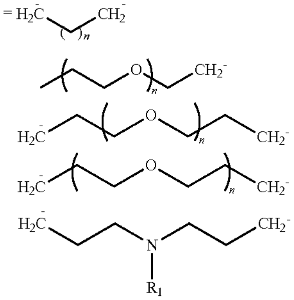

n = 1-8

R may be selected from hydrogen, deuterium, halo, —CN, —$NO_2$, and an optionally substituted aliphatic, alicyclic, heteroaliphatic, heterocyclic, aromatic, acyl or heteroaromatic group.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiment, R1 a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R1 is allyl. In some embodiments, R1 is formyl (methanoyl), acetyl (ethanoyl), propanoyl, butanoyl, propenoyl (acryloyl), or butenoyl (crotonyl).

In some embodiments, acyl is formyl or acetyl.

Other protecting groups in addition to Boc, Cbz and Fmoc may be used.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Example 17. Synthetic Route for Compounds of Formula IIB

The scheme shown in the figure below may be used to prepare compounds in Examples 30-31. The definitions of the substituents are as described elsewhere herein.

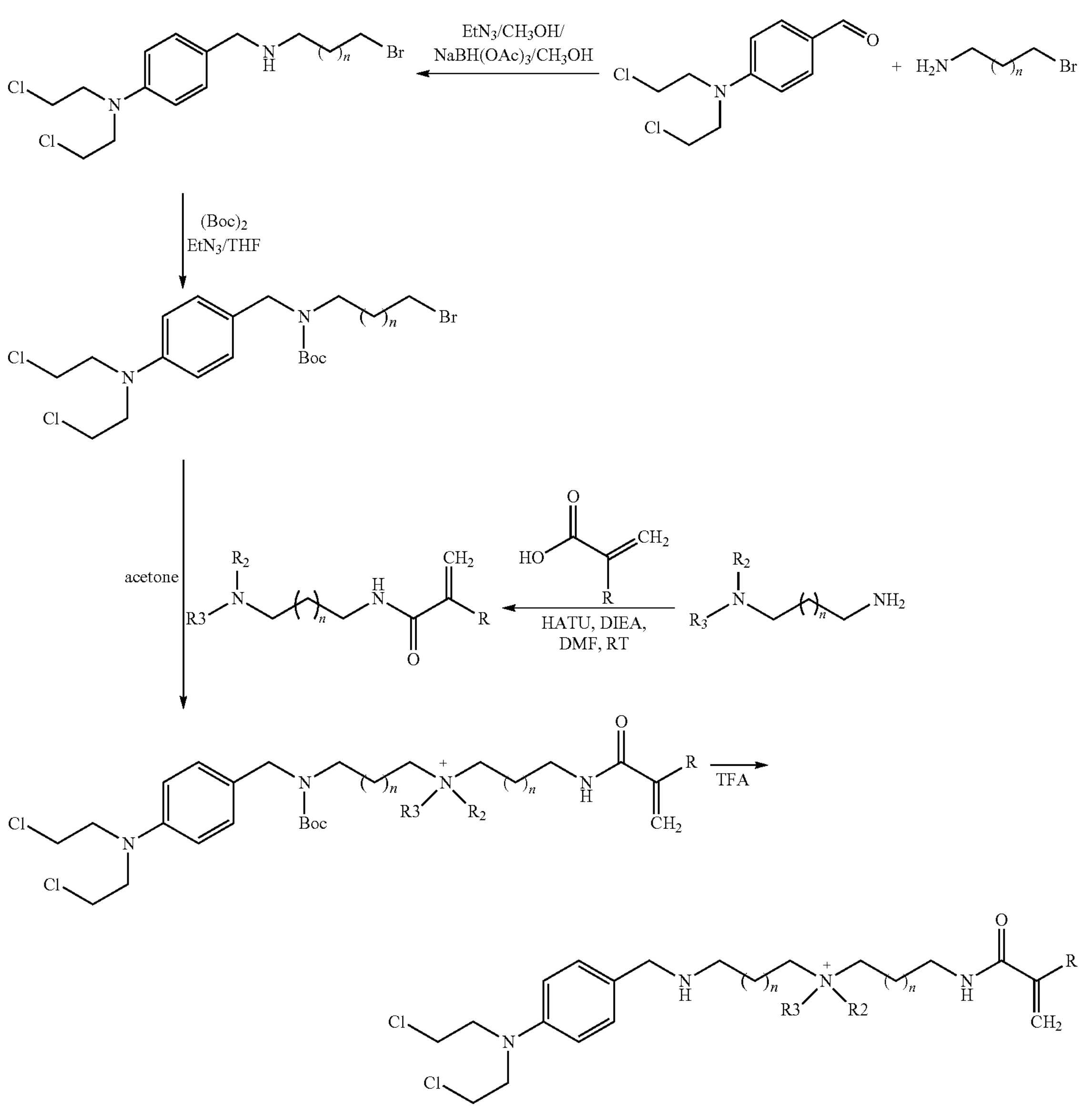

II B n = 1-8

In addition to the above independent selection of each occurrence of n, R may be selected from hydrogen, deuterium, halo, —CN, —$NO_2$, and an optionally substituted aliphatic, alicyclic, heteroaliphatic, heterocyclic, aromatic, acyl or heteroaromatic group.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiments, R2 and R3 are independently $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R2 or R3 is independently allyl. In some embodiments R2 and R3 are independently formyl (methanoyl), acetyl (ethanoyl), propanoyl, butanoyl, propenoyl (acryloyl), or butenoyl (crotonyl).

In some embodiments, acyl is formyl or acetyl.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Example 18. Synthetic Route for Compounds of Formula IIIA

The scheme shown in the figure below may be used to prepare compounds in Examples 32-51. The definitions of the substituents are as described elsewhere herein.

In addition to the above independent selections of each occurrence of n, R may be selected from hydrogen, deuterium, halo, —CN, —$NO_2$, and an optionally substituted aliphatic, alicyclic, heteroaliphatic, heterocyclic, aromatic, acyl or heteroaromatic group.

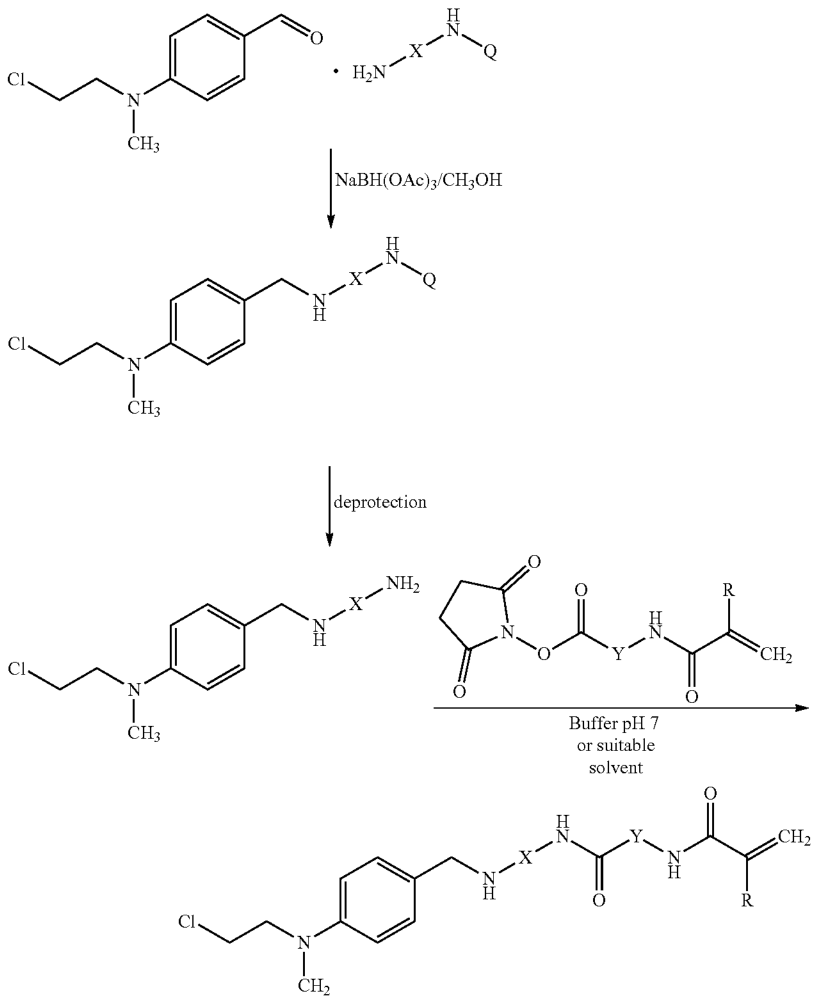

III A

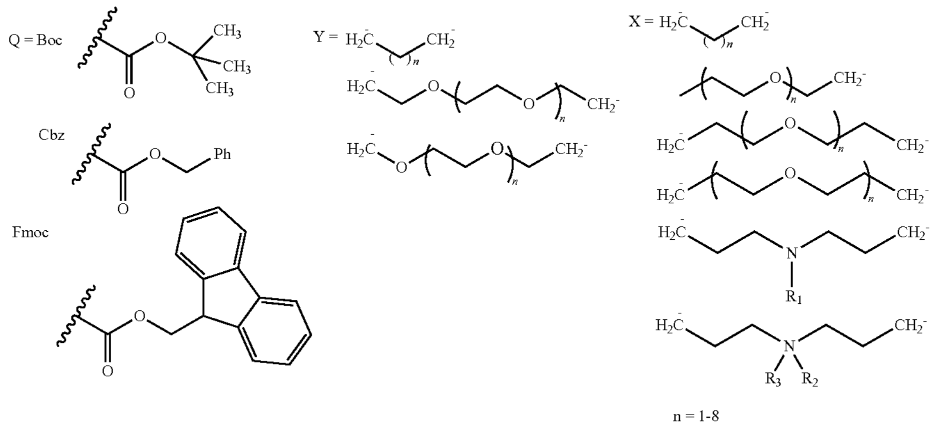

n = 1-8

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiments, R1, R2 and R3 are independently $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R1, R2 or R3 is allyl.

In some embodiments, acyl is formyl or acetyl.

Other protecting groups in addition to Boc, Cbz and Fmoc may be used.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Example 19. Synthetic Route for Compounds of Formula IIIB

The scheme shown in the figure below may be used to prepare compounds in Examples 52-71. The definitions of the substituents are as described elsewhere herein.

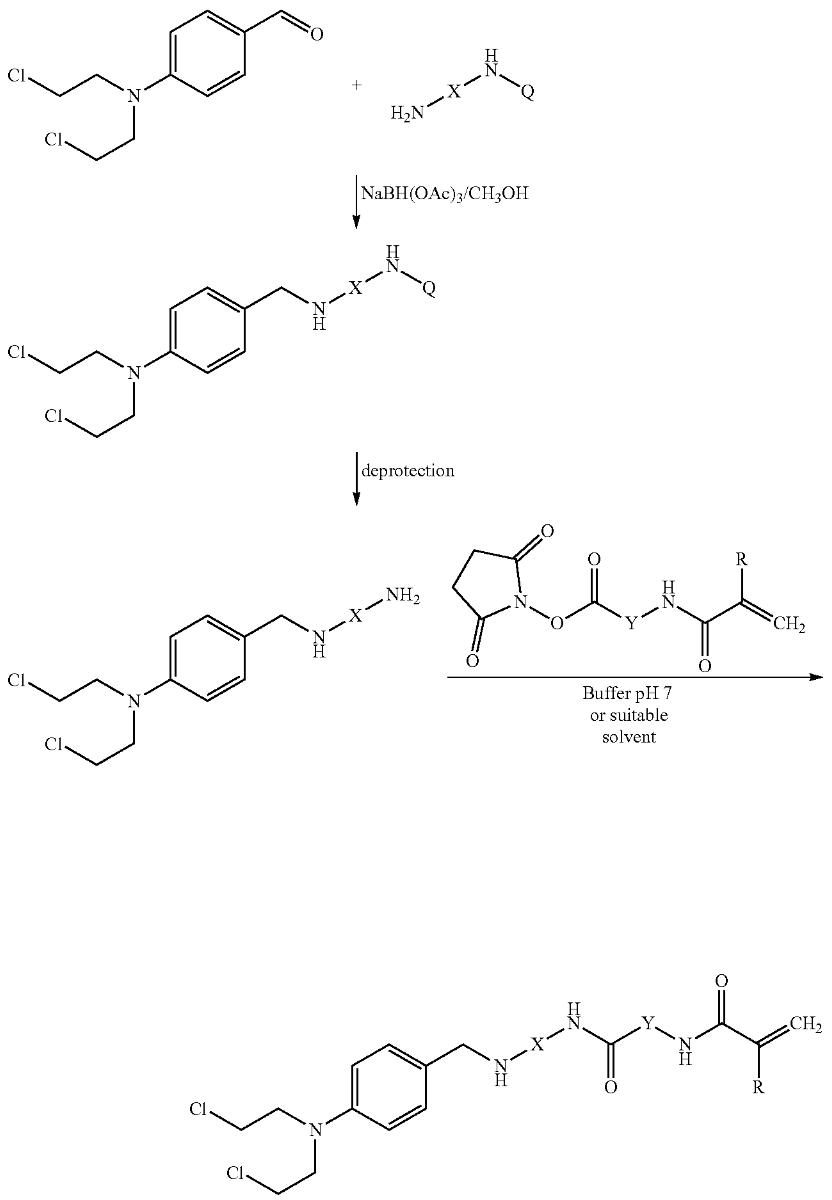

III B

-continued

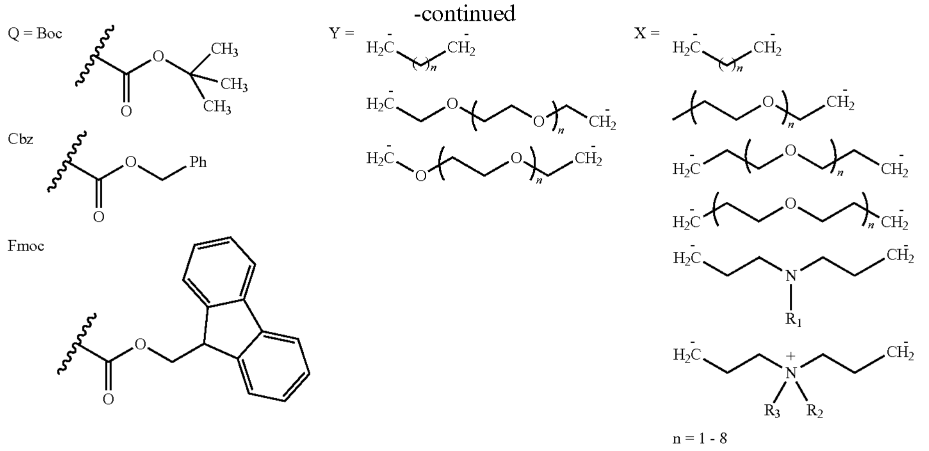

R may be selected from hydrogen, deuterium, halo, —CN, —$NO_2$, and an optionally substituted aliphatic, alicyclic, heteroaliphatic, heterocyclic, aromatic, acyl or heteroaromatic group.

In some embodiments, R is a $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R is allyl.

In some embodiments, R1, R2 and R3 are independently $C_{1-6}$ alkyl. In some embodiments, $C_{1-6}$ alkyl is methyl, ethyl, propyl, butyl, pentyl or hexyl. In some embodiments propyl is n-propyl or 2-propyl. In some embodiments butyl is n-butyl, 2-butyl or tert-butyl. In some embodiments, R1, R2 or R3 is allyl.

In some embodiments, acyl is formyl or acetyl.

Other protecting groups in addition to Boc, Cbz and Fmoc may be used.

Non-limiting examples of optional substitutions of each R independently include hydrogen, deuterium, halo, —CN, —$NO_2$, aliphatic, alicyclic, heteroaliphatic, heterocyclic, aromatic, heteroaromatic, —$OR^{aa}$, —$NR^{bb}R^{cc}$, —$S(=O)_wR^{dd}$, —$S(=O)_wNR^{ee}R^{ff}$, —$C(=O)R^{gg}$, —$CO_2R^{hh}$, —$CONR^{ii}R^{jj}$, —$NR^{kk}CONR^{ll}R^{mm}$, —$OCONR^{nn}R^{oo}$, or —$NR^{kk}CO_2R^{pp}$; wherein $R^{aa}$, $R^{bb}$, $R^{cc}$, $R^{dd}$, $R^{ee}$, $R^{ff}$, $R^{gg}$, $R^{hh}$, $R^{ii}$, $R^{jj}$, $R^{kk}$, $R^{ll}$, $R^{mm}$, $R^{nn}$, $R^{oo}$, and $R^{pp}$, for each occurrence, is independently selected from hydrogen, deuterium, halo, —CN, —$NO_2$, —OH, —$CH_2F$, —$CHF_2$, —$CF_3$, —$OCH_3$, —$OCH_2F$, —$OCHF_2$, —$OCF_3$, —$NH_2$, —$NHCH_3$, —$N(CH_3)_2$, —$CO_2H$, —SH, —$S(O)_wCH_3$, or an aliphatic, alicyclic, heteroaliphatic, heterocyclic, aromatic, or heteroaromatic; and w is 0, 1, or 2.

Example 20. Synthetic Route for Compound IIA-1

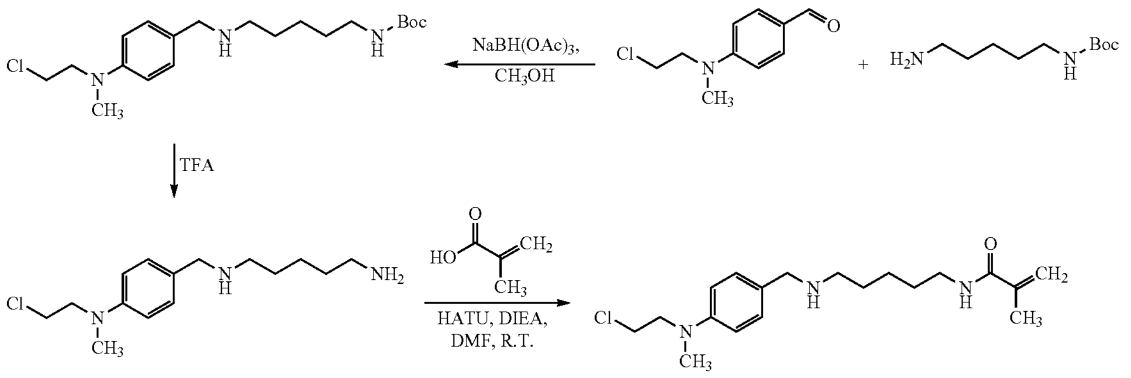

Example 21. Synthetic Route for Compound IIA-2

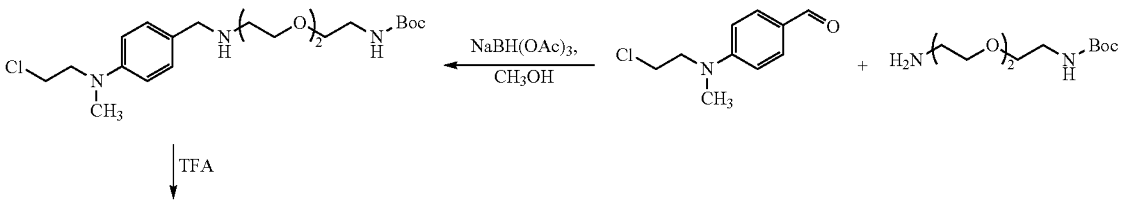

-continued
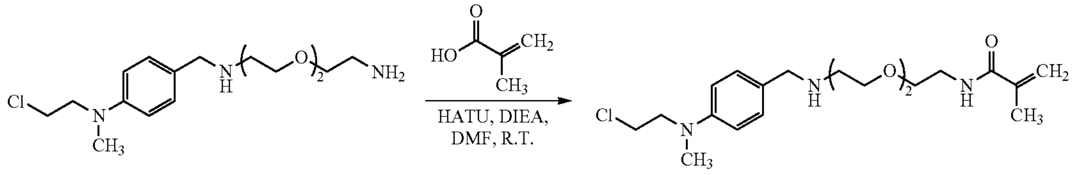
Example 22. Synthetic Route for Compound IIA-3
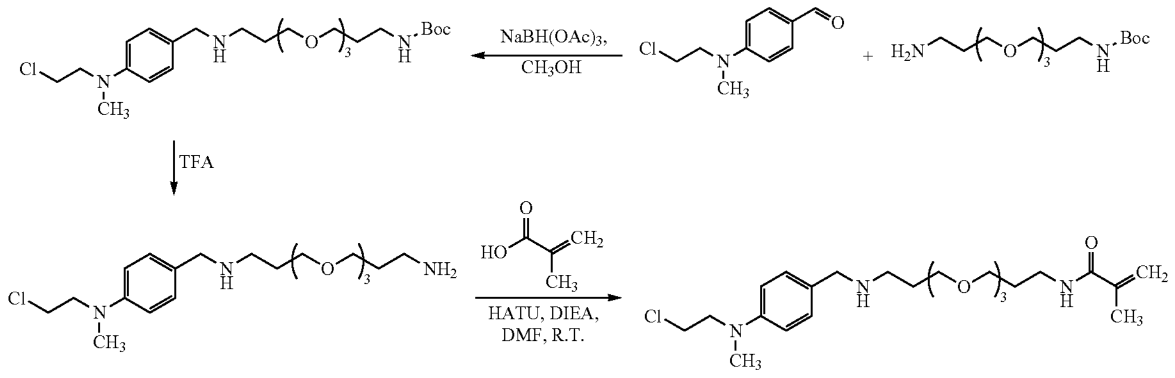
Example 23. Synthetic Route for Compound IIA-4

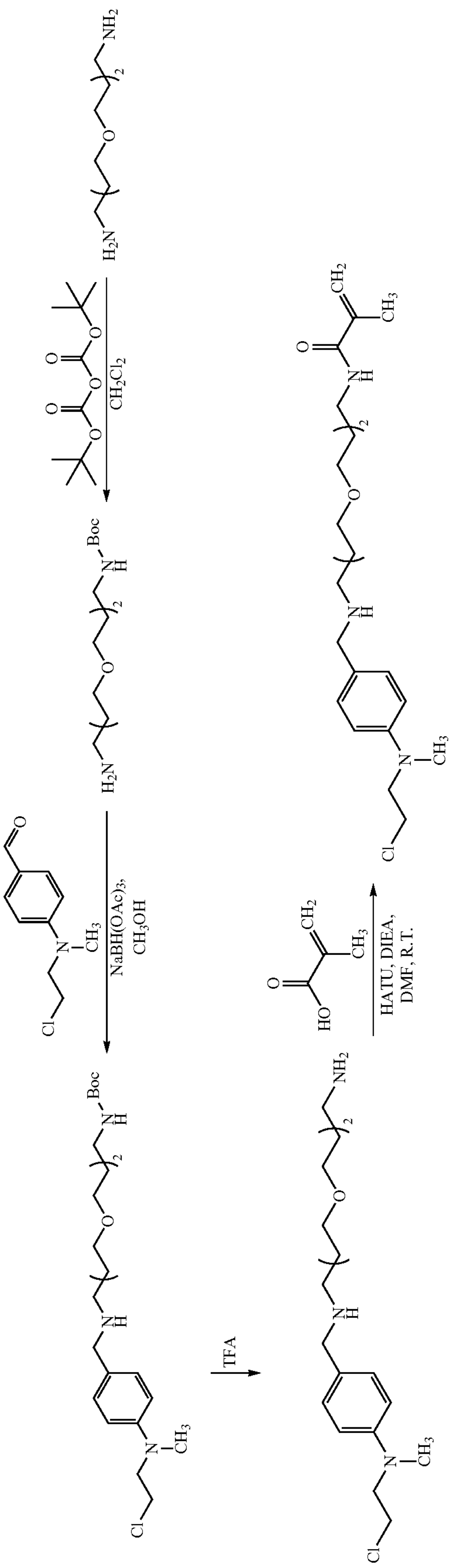
$CH_2Cl_2$
$NaBH(OAc)_3$,
$CH_3OH$
TFA
HATU, DIEA,
DMF, R.T.

Example 24. Synthetic Route for Compound IIA-5

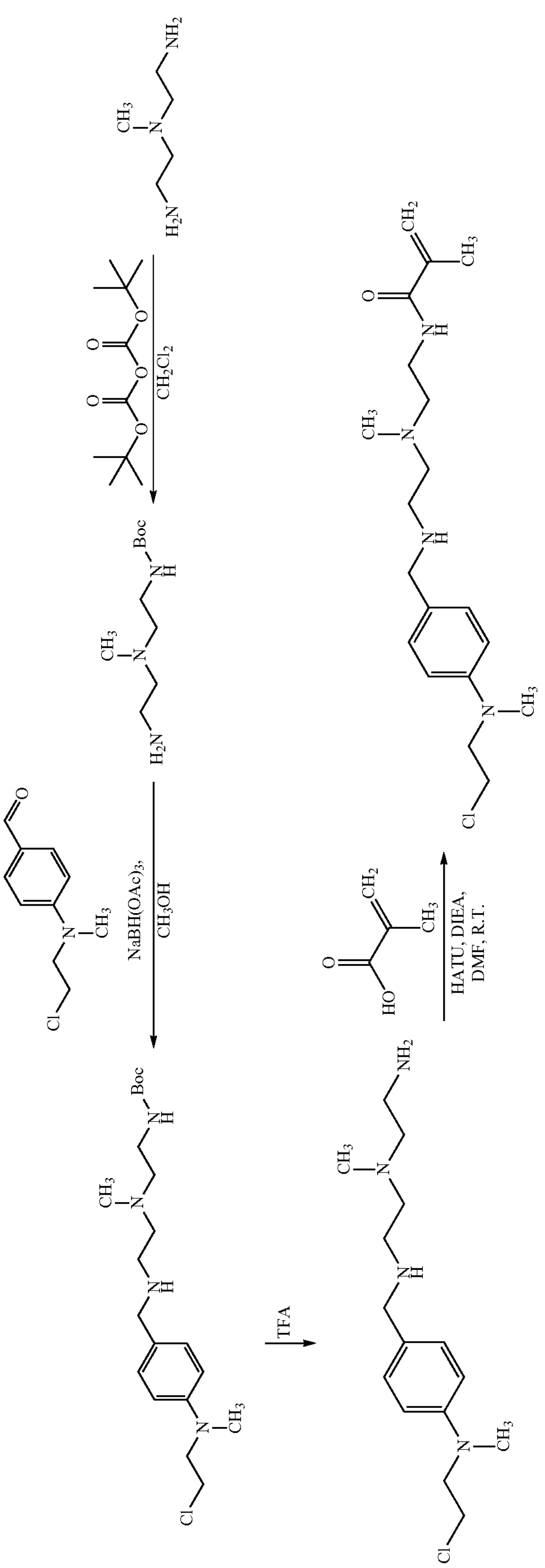
CH2Cl2
NaBH(OAc)3,
CH3OH
TFA
HATU, DIEA,
DMF, R.T.

Example 25. Synthetic Route for Compound IIA-6
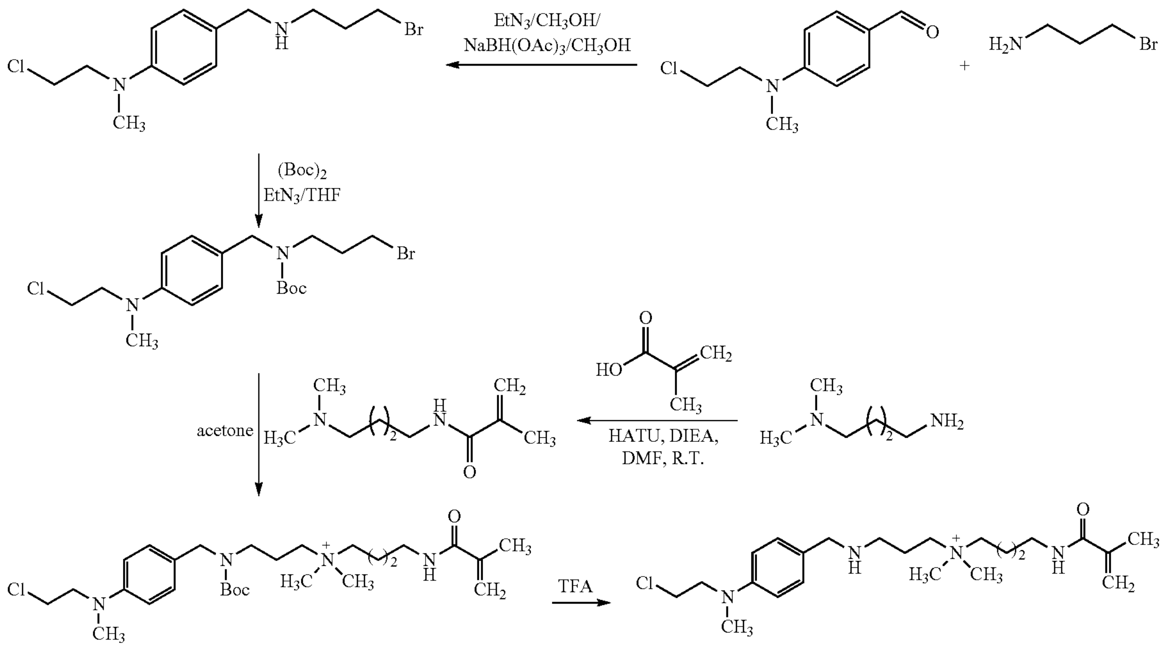
Example 26. Synthetic Route for Compound IIB-1
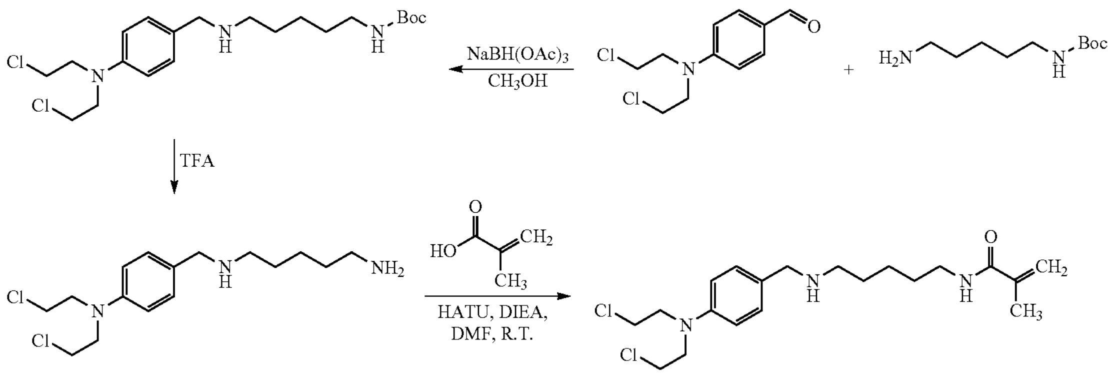
Example 27. Synthetic Route for Compound IIB-2
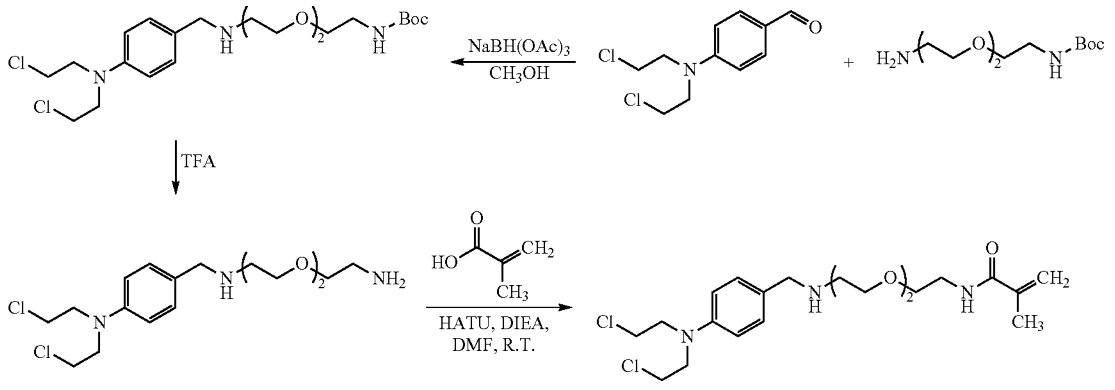

Example 28. Synthetic Route for Compound IIB-3
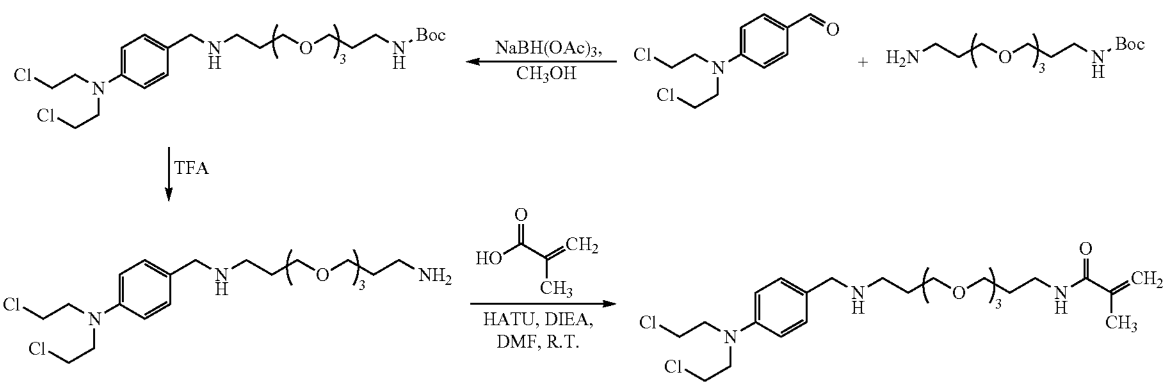
Example 29. Synthetic Route for Compound IIB-4

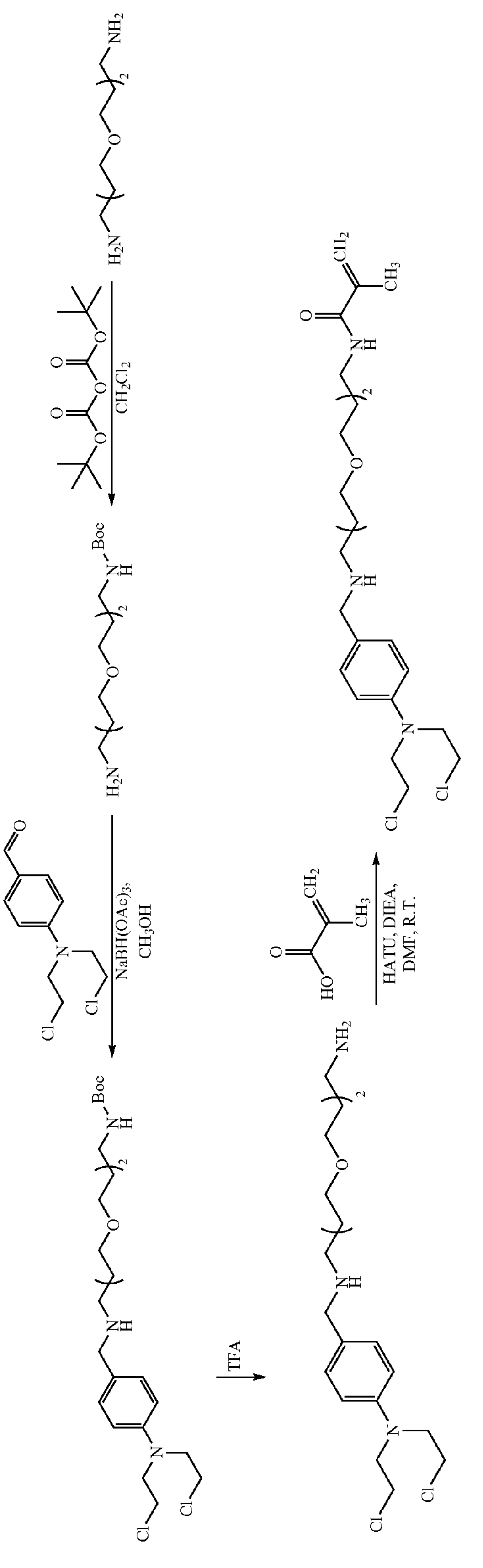
CH$_2$Cl$_2$
NaBH(OAc)$_3$,
CH$_3$OH
TFA
HATU, DIEA,
DMF, R.T.

Example 30. Synthetic Route for Compound IIB-5

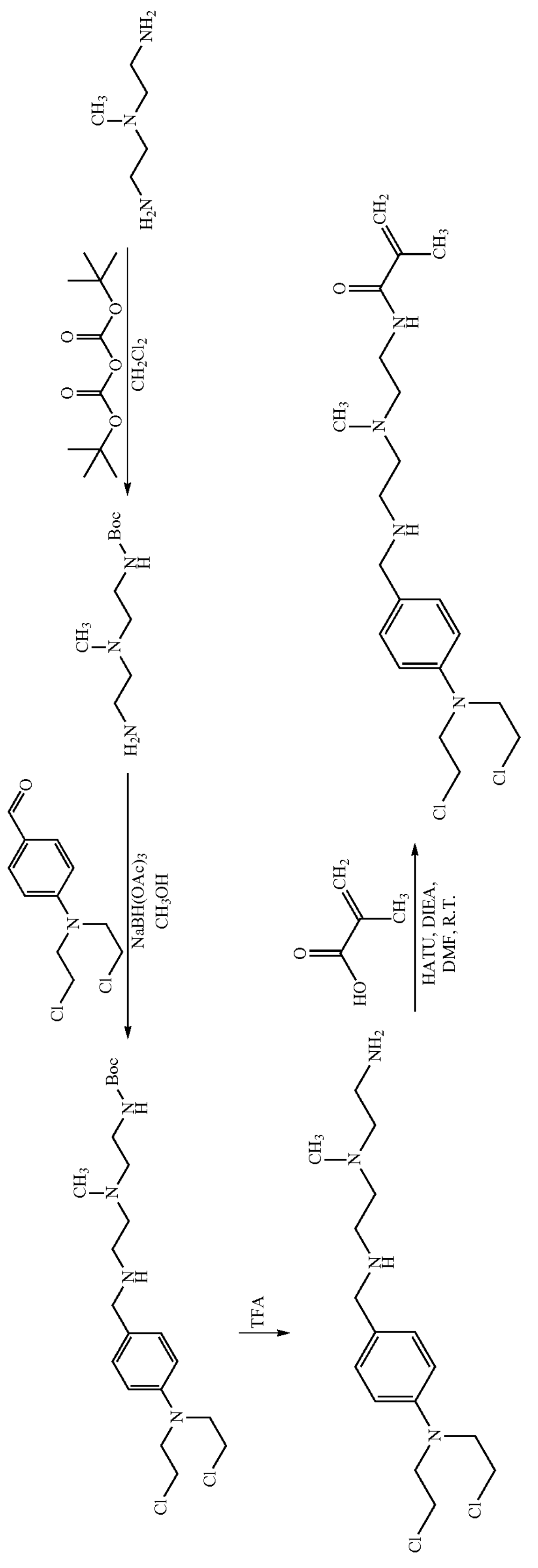
CH2Cl2
NaBH(OAc)3
CH3OH
TFA
HATU, DIEA,
DMF, R.T.

Example 31. Synthetic Route for Compound IIB-6
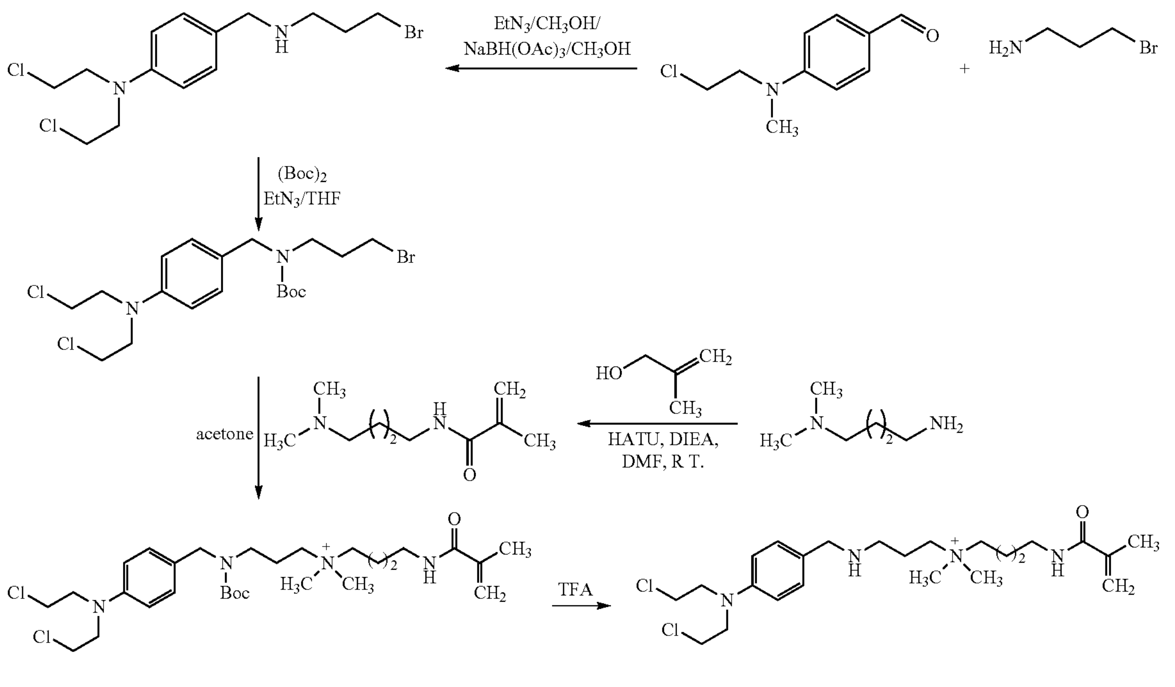
Example 32. Synthetic Route for Compound IIIA-1
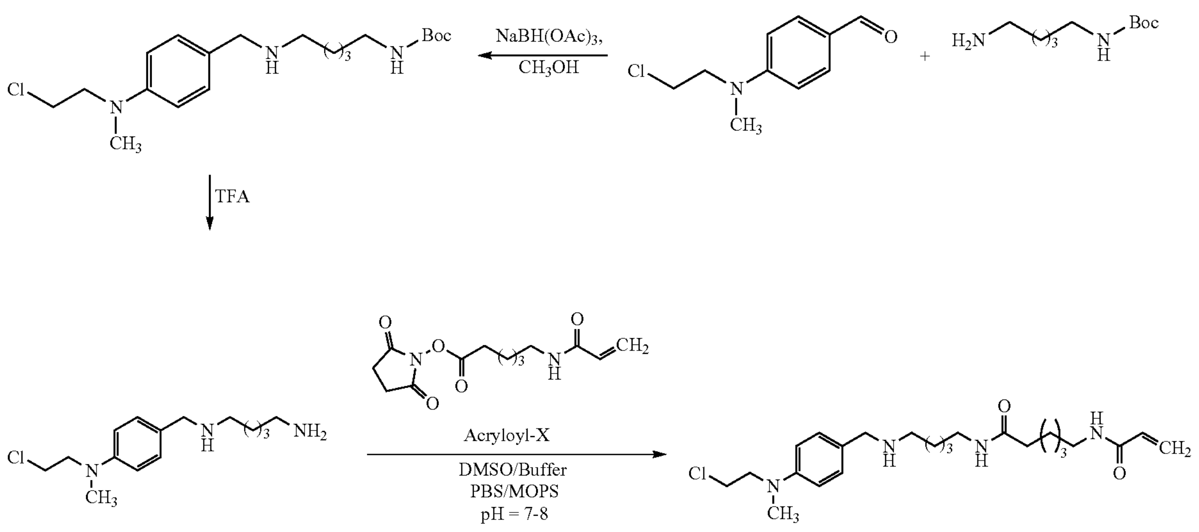
Example 33. Synthetic Route for Compound IIIA-2
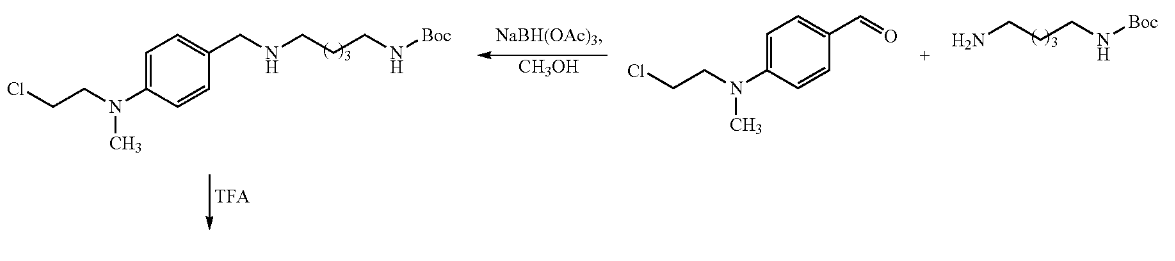

-continued
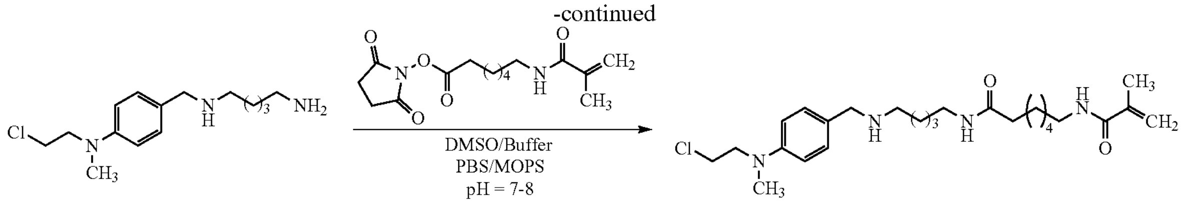
Example 34. Synthetic Route for Compound IIIA-3

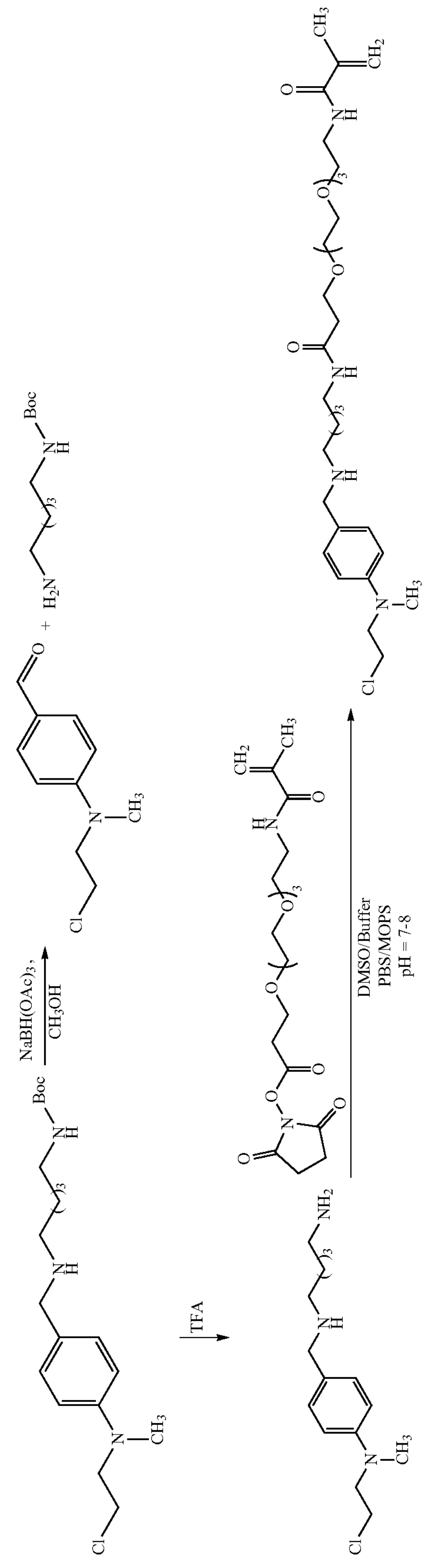
NaBH(OAc)$_3$,
CH$_3$OH
TFA
DMSO/Buffer
PBS/MOPS
pH = 7-8

Example 35. Synthetic Route for Compound IIIA-4
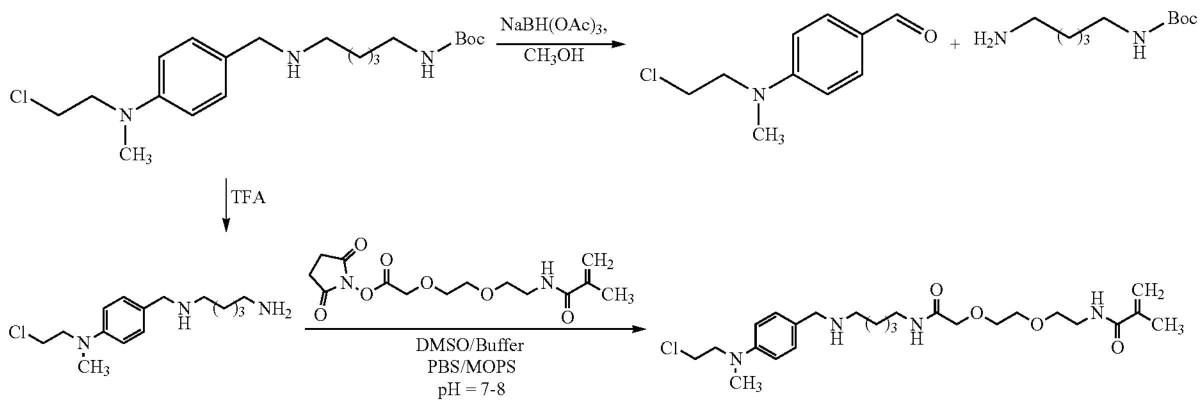
Example 36. Synthetic Route for Compound IIIA-5

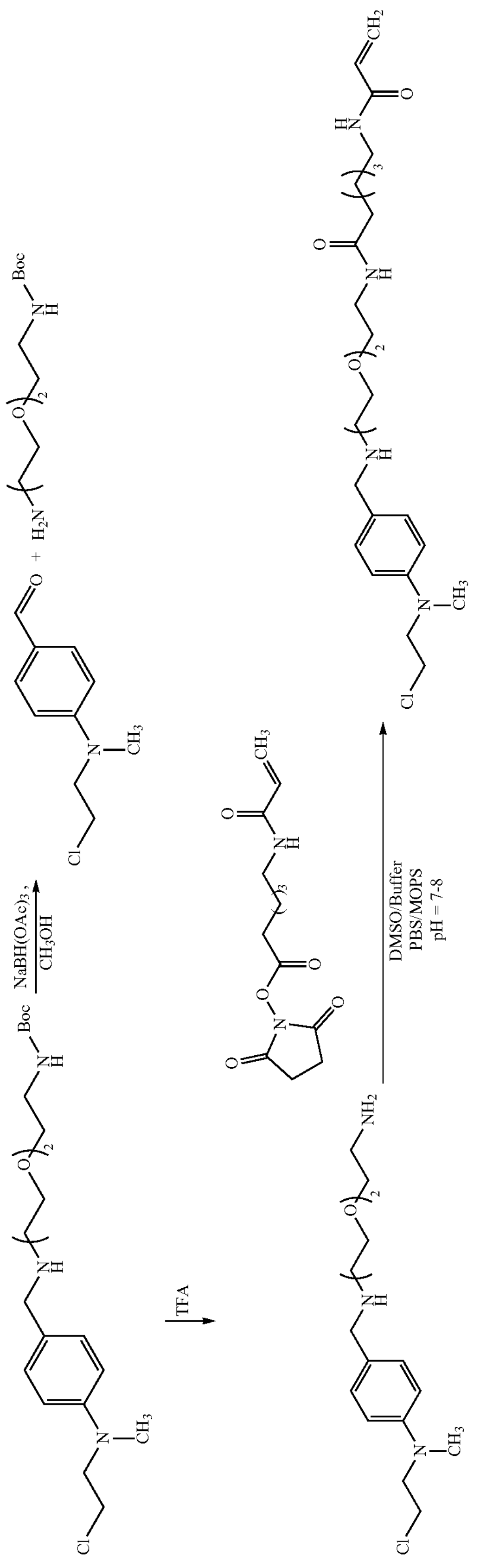
NaBH(OAc)3,
CH3OH
TFA
DMSO/Buffer
PBS/MOPS
pH = 7-8

Example 37. Synthetic Route for Compound IIIA-6

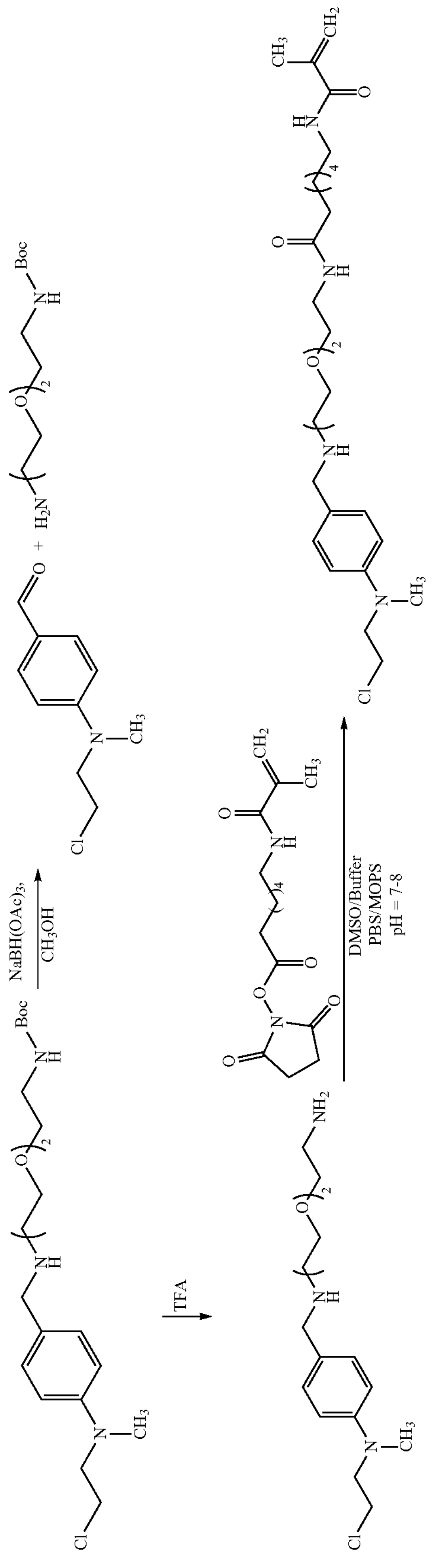
$NaBH(OAc)_3$,
$CH_3OH$
TFA
DMSO/Buffer
PBS/MOPS
pH = 7-8

Example 38. Synthetic Route for Compound IIIA-7

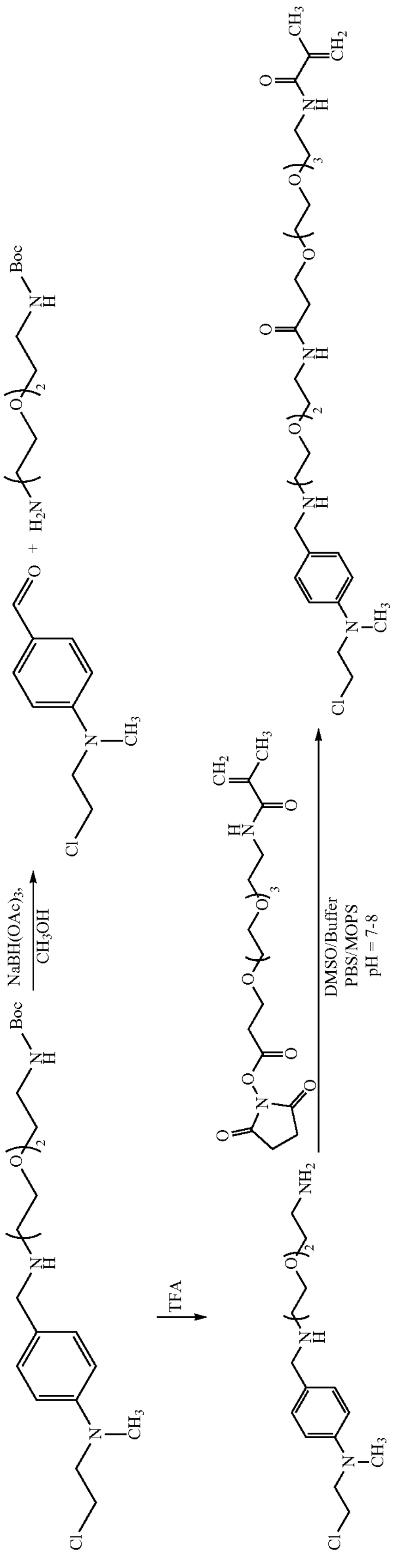
NaBH(OAc)$_3$,
$CH_3OH$
TFA
DMSO/Buffer
PBS/MOPS
pH = 7-8

Example 39. Synthetic Route for Compound IIIA-8

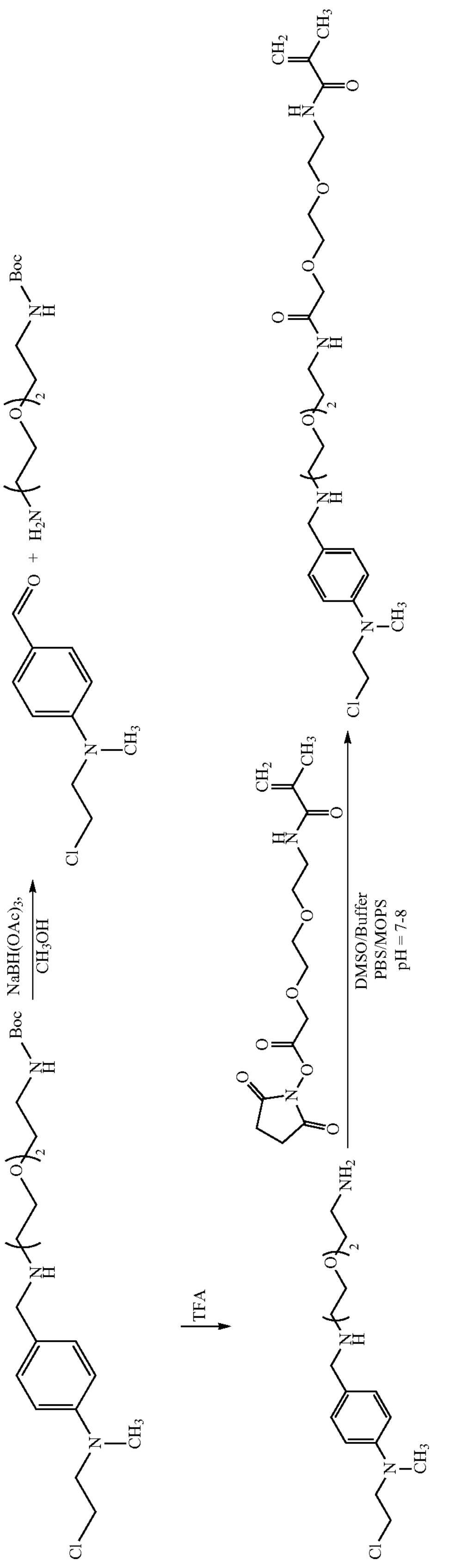
NaBH(OAc)$_3$,
$CH_3OH$
TFA
DMSO/Buffer
PBS/MOPS
pH = 7-8

Example 40. Synthetic Route for Compound IIIA-9

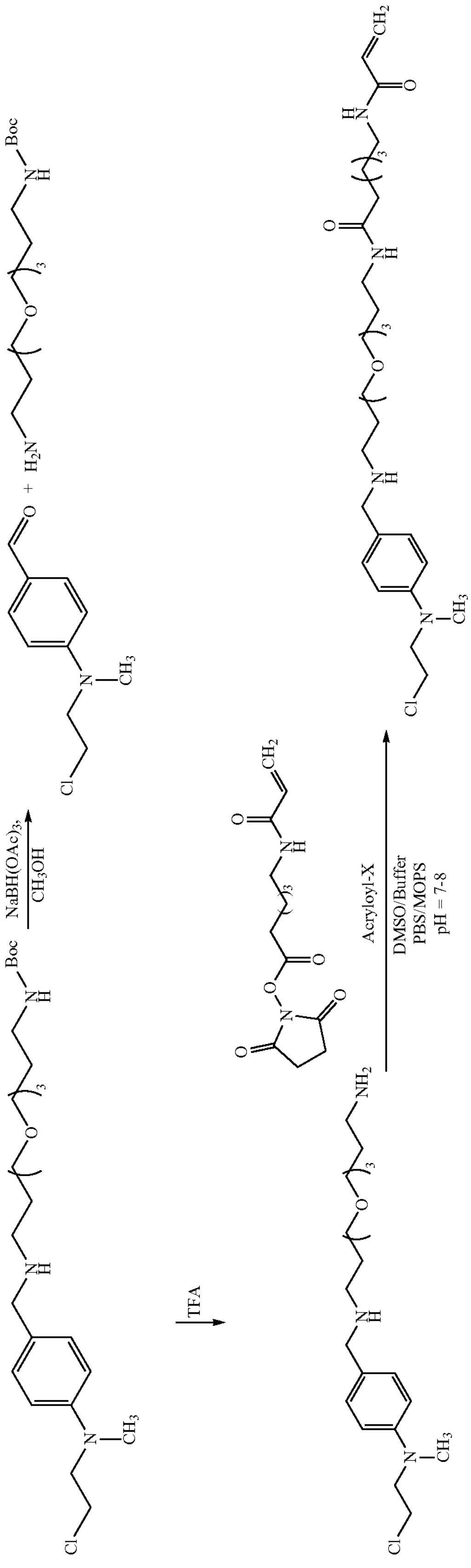
$NaBH(OAc)_3$,
$CH_3OH$
TFA
Acryloyl-X
DMSO/Buffer
PBS/MOPS
pH = 7-8

Example 41. Synthetic Route for Compound IIIA-10

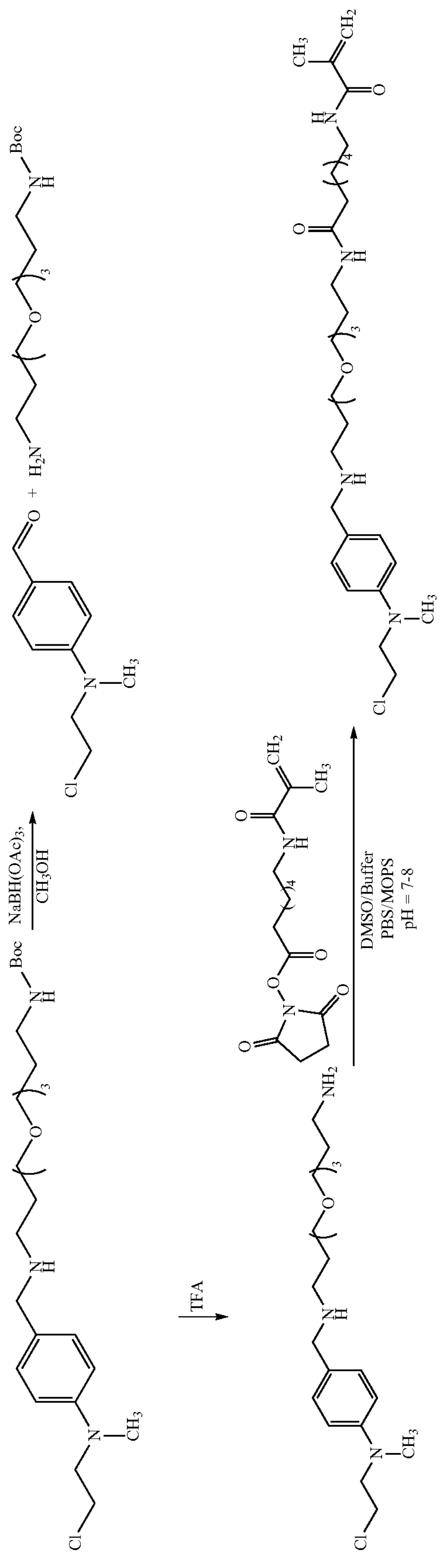
NaBH(OAc)$_3$,
$CH_3OH$
TFA
DMSO/Buffer
PBS/MOPS
pH = 7-8

Example 42. Synthetic Route for Compound IIIA-11

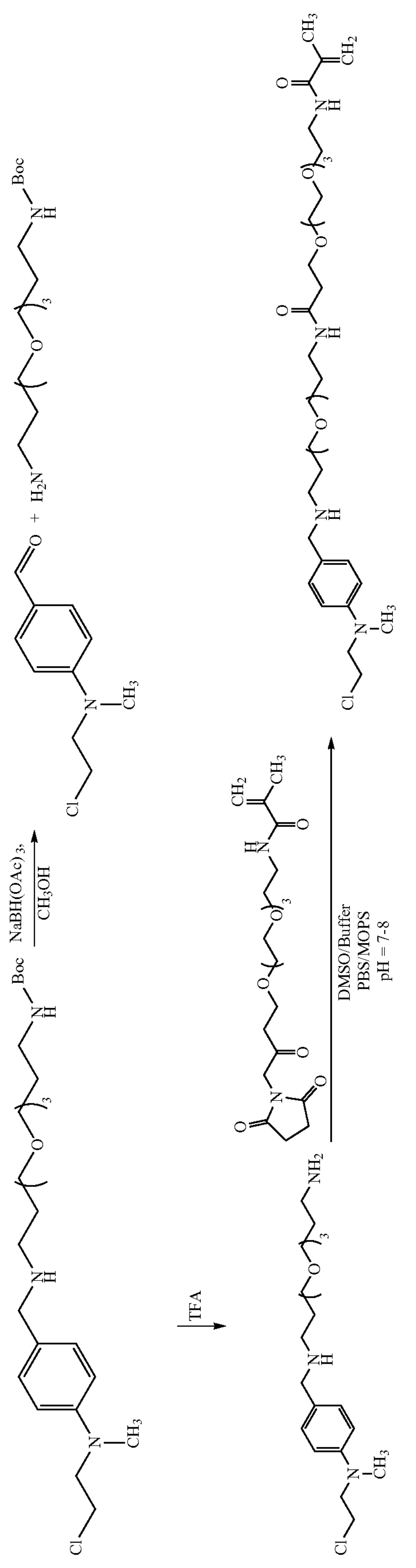
NaBH(OAc)$_3$,
CH$_3$OH
TFA
DMSO/Buffer
PBS/MOPS
pH = 7-8

Example 43. Synthetic Route for Compound IIIA-12

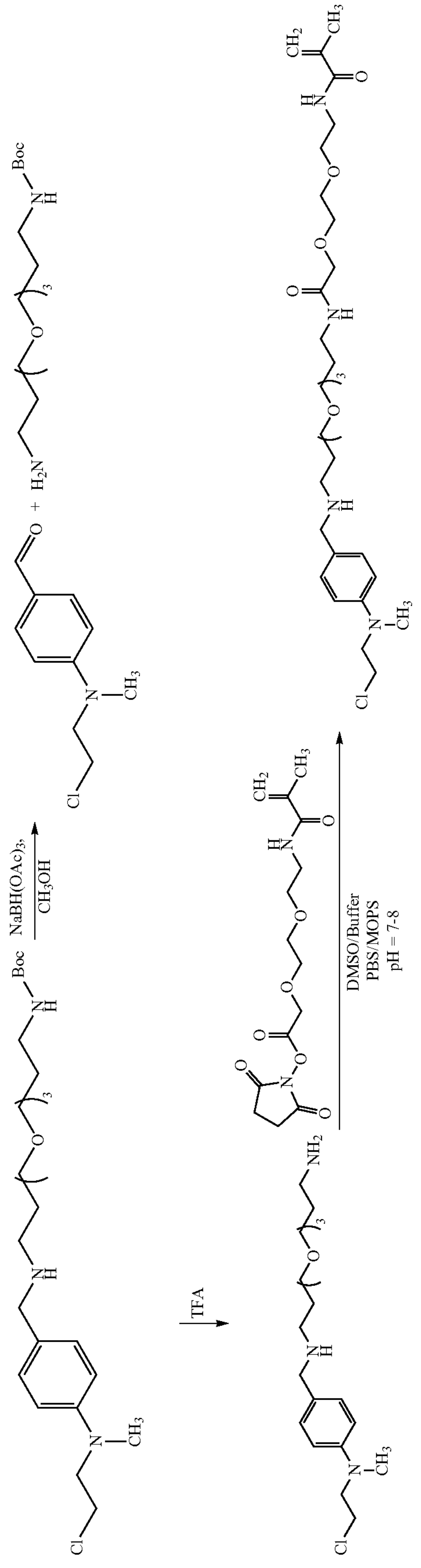
NaBH(OAc)3,
CH3OH
TFA
DMSO/Buffer
PBS/MOPS
pH = 7-8

Example 44. Synthetic Route for Compound IIIA-13

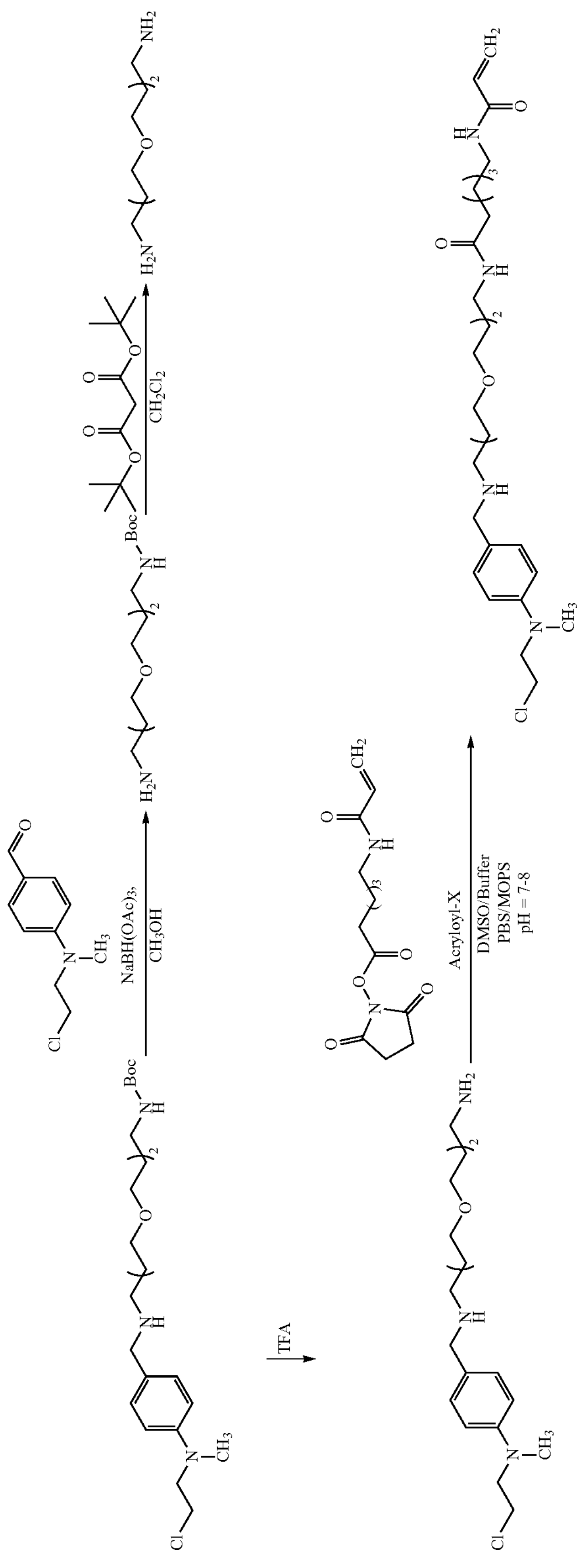
NaBH(OAc)$_3$,
CH$_3$OH
CH$_2$Cl$_2$
TFA
Acryloyl-X
DMSO/Buffer
PBS/MOPS
pH = 7-8

Example 45. Synthetic Route for Compound IIIA-14

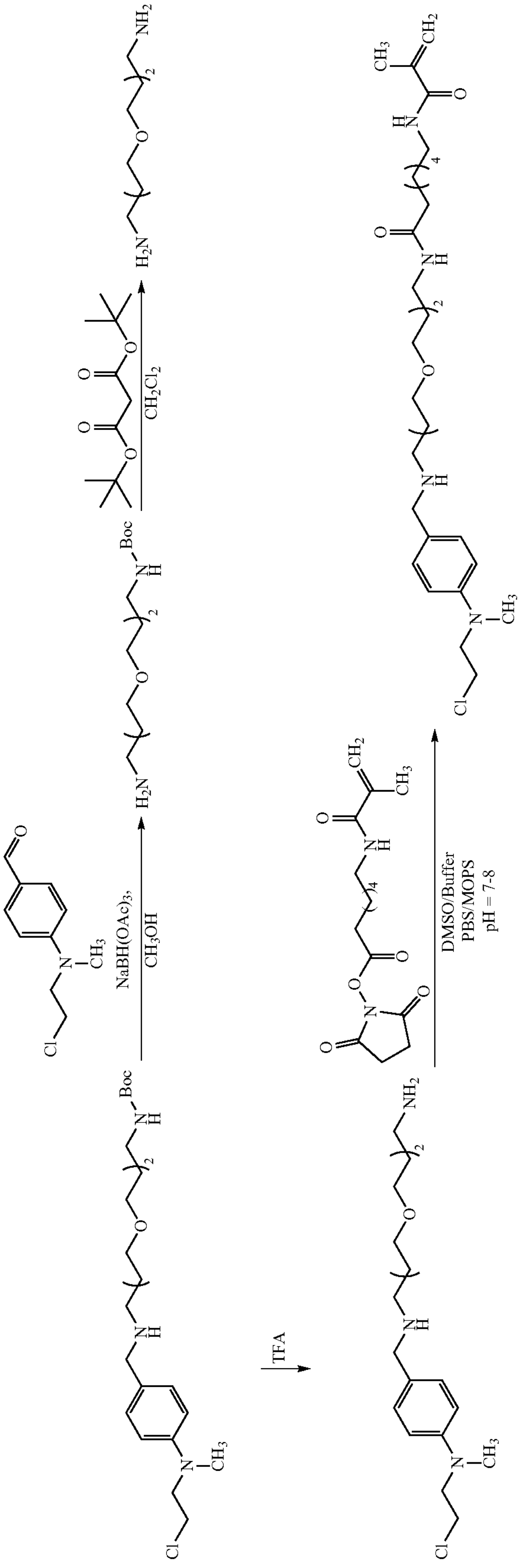
NaBH(OAc)$_3$,
$CH_3OH$
$CH_2Cl_2$
TFA
DMSO/Buffer
PBS/MOPS
pH = 7-8

Example 46. Synthetic Route for Compound IIIA-15

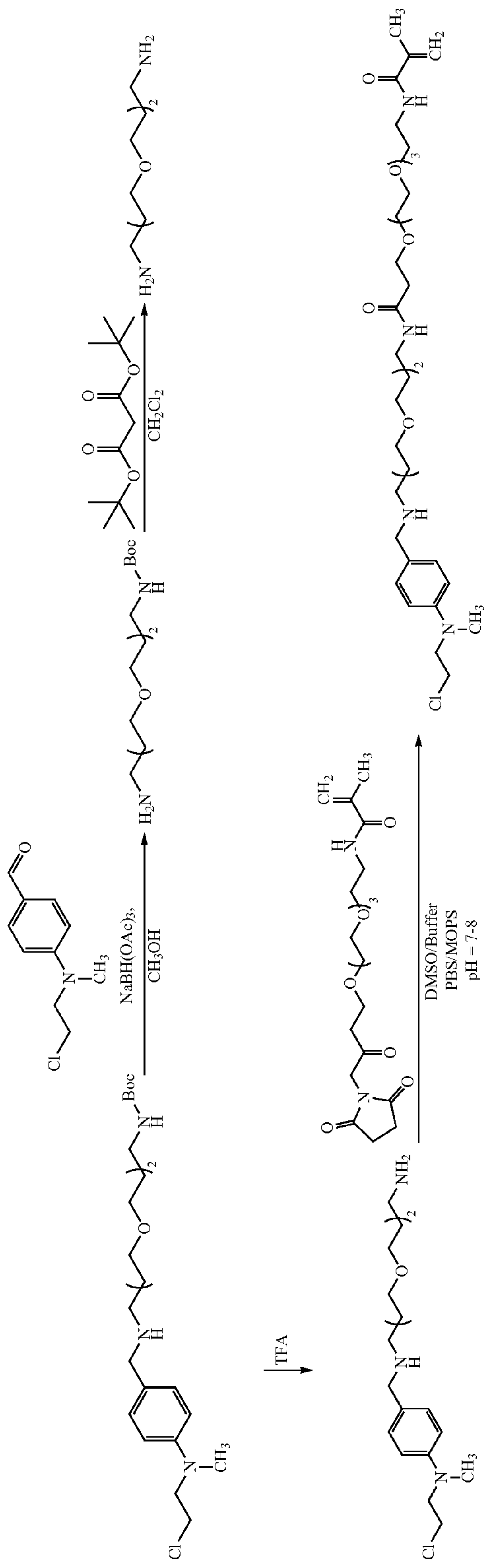
NaBH(OAc)3,
CH3OH
CH2Cl2
TFA
DMSO/Buffer
PBS/MOPS
pH = 7-8

Example 47. Synthetic Route for Compound IIIA-16

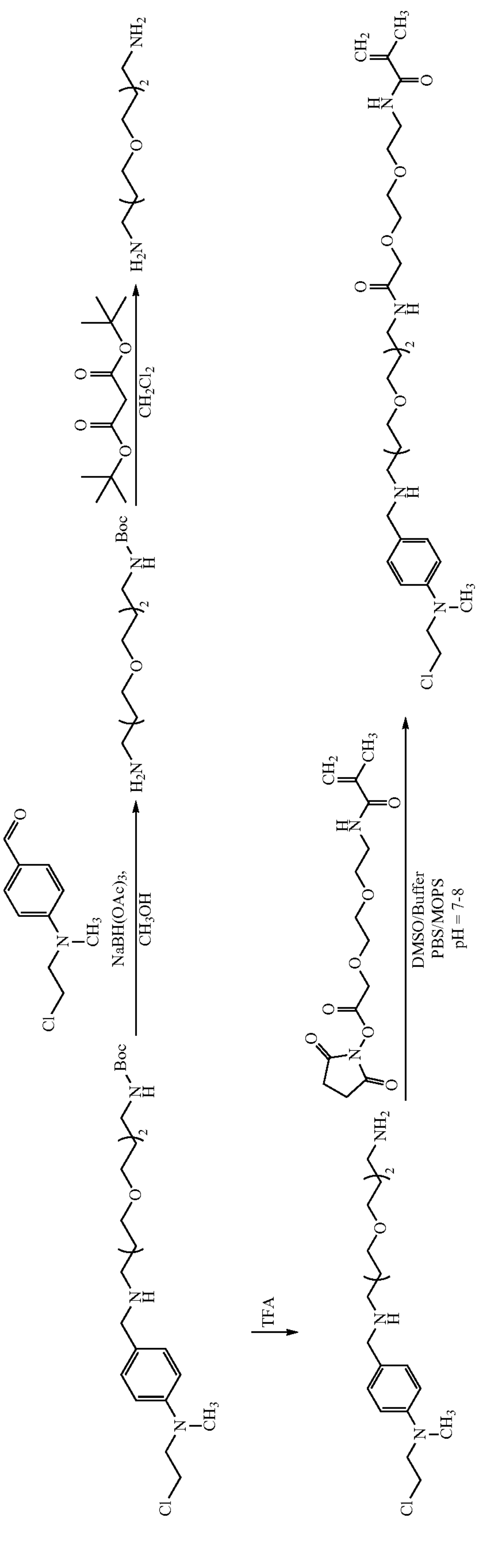
NaBH(OAc)$_3$,
$CH_3OH$
$CH_2Cl_2$
TFA
DMSO/Buffer
PBS/MOPS
pH = 7-8

Example 48. Synthetic Route for Compound IIIA-17

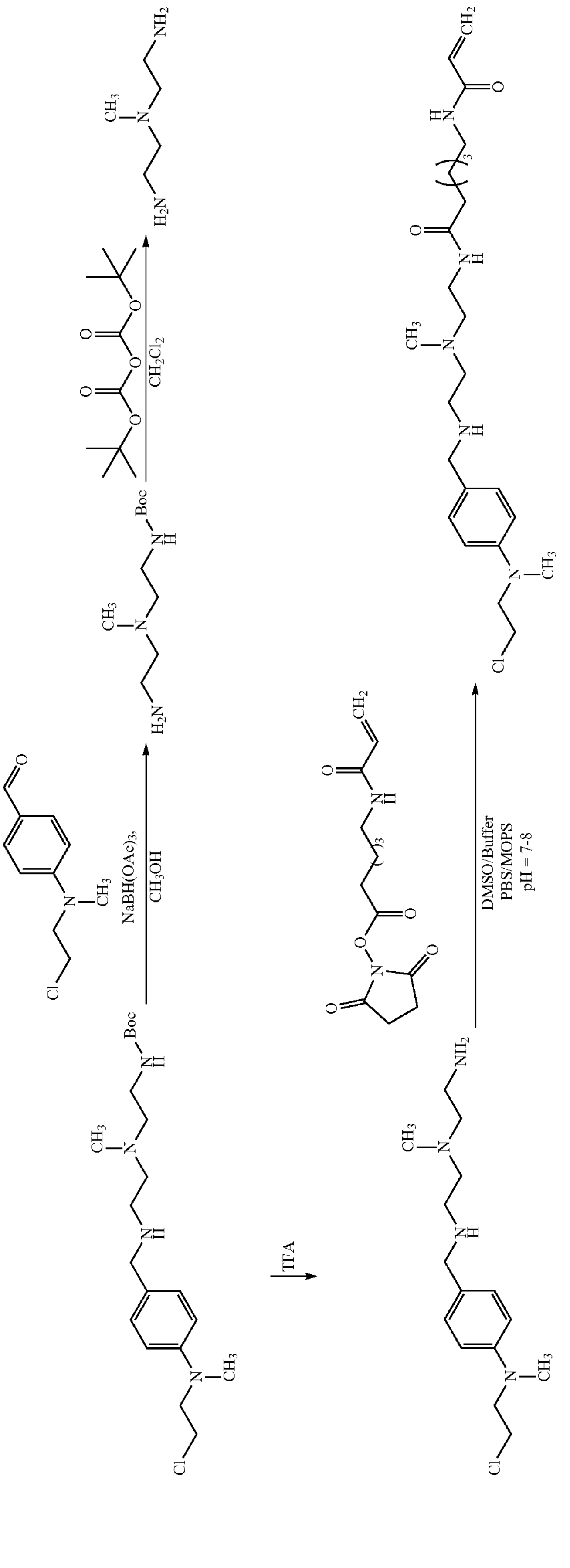
NaBH(OAc)3,
CH3OH
CH2Cl2
TFA
DMSO/Buffer
PBS/MOPS
pH = 7-8

Example 49. Synthetic Route for Compound IIIA-18
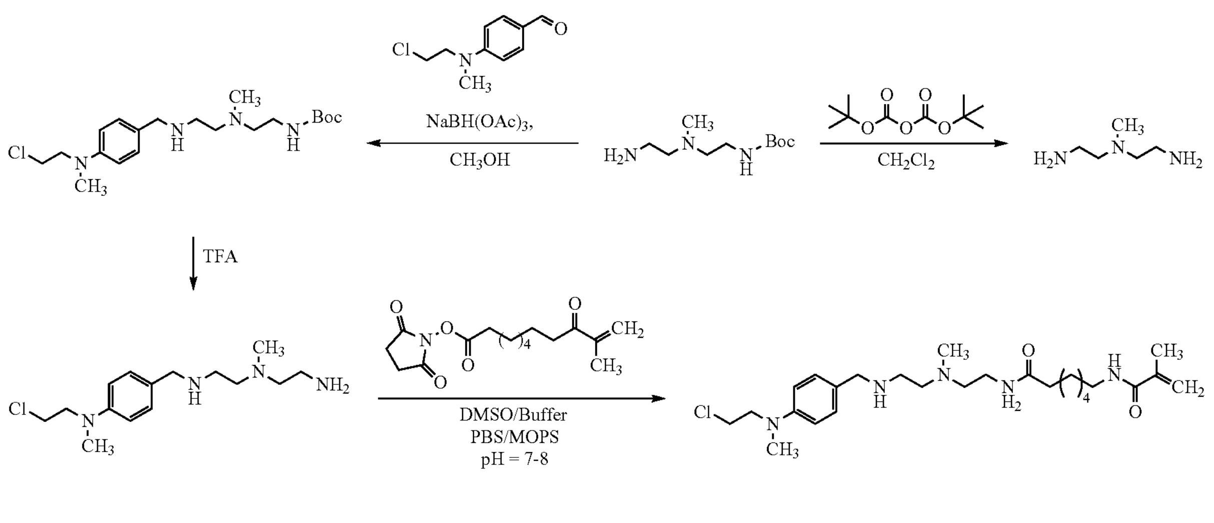
Example 50. Synthetic Route for Compound IIIA-19
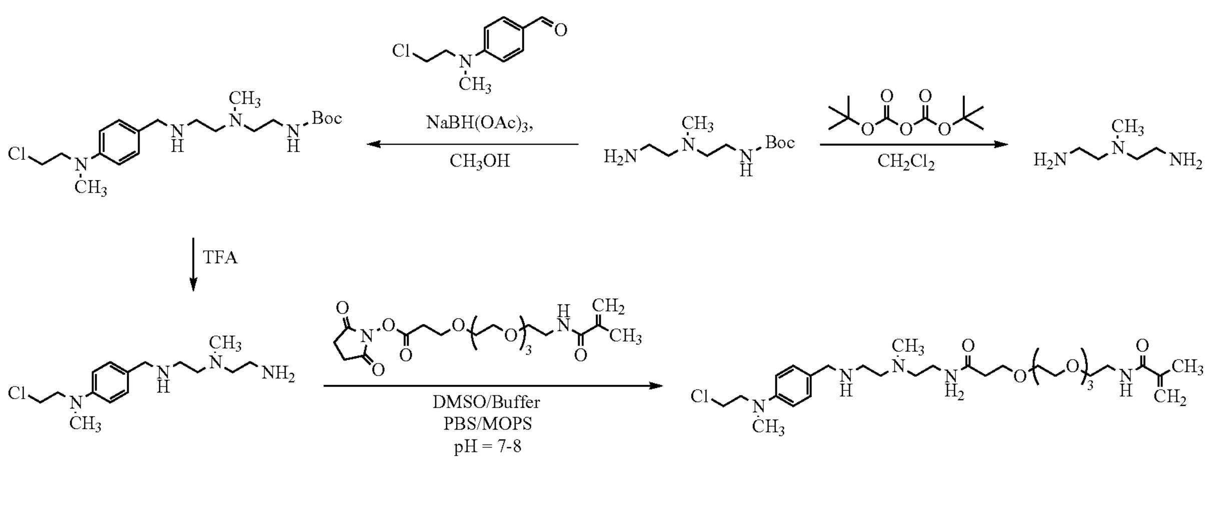
Example 51. Synthetic Route for Compound IIIA-20
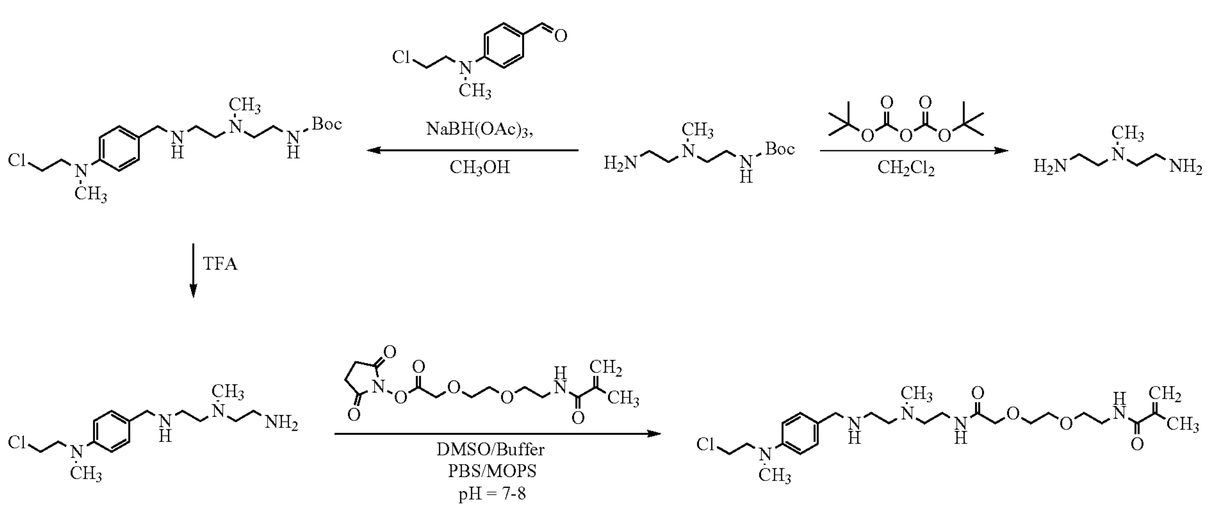

Example 52. Synthetic Route for Compound IIIB-1
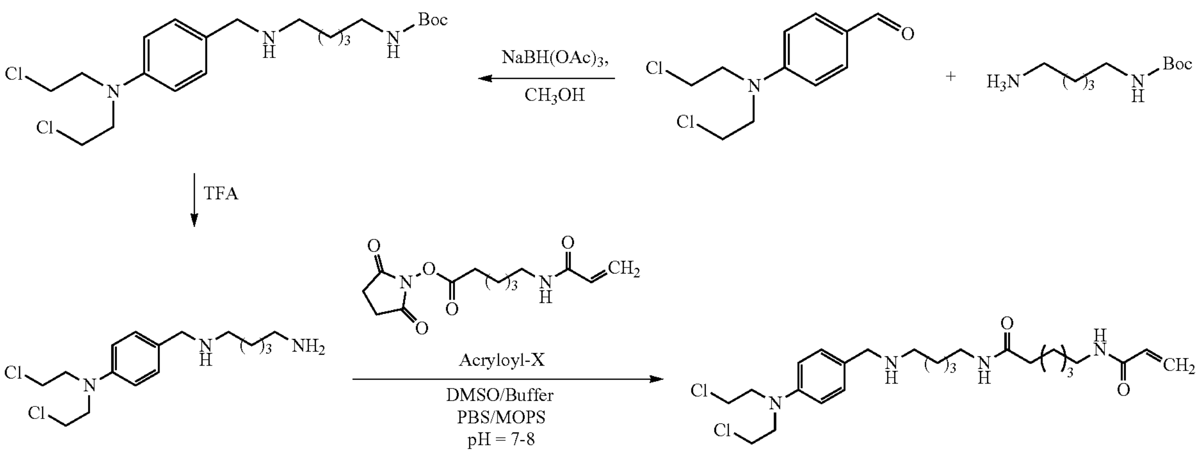
Example 53. Synthetic Route for Compound IIIB-2
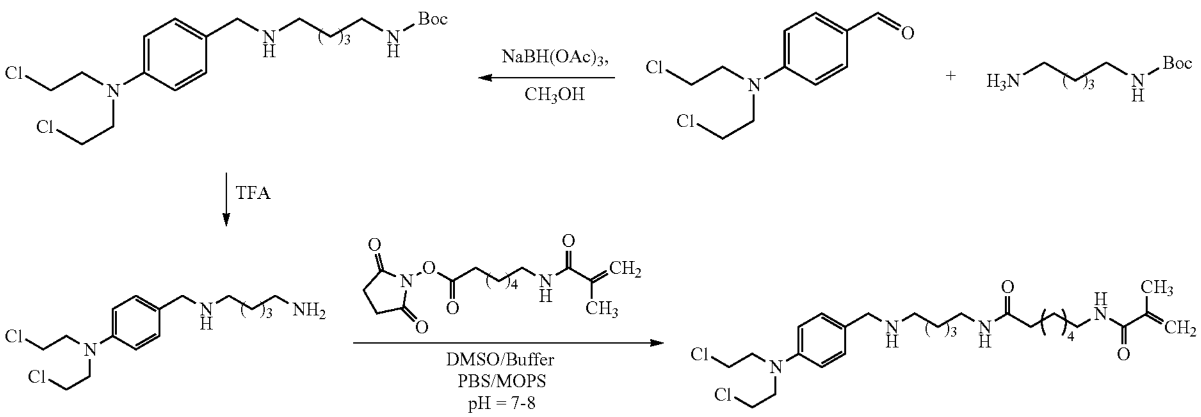
Example 54. Synthetic Route for Compound IIIB-3
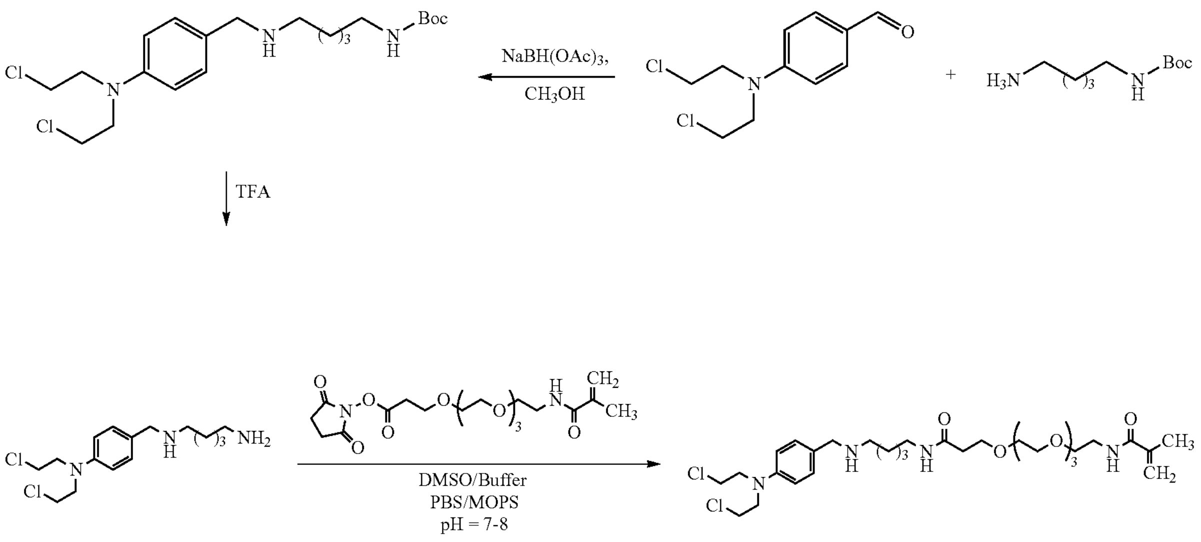

Example 55. Synthetic Route for Compound IIIB-4
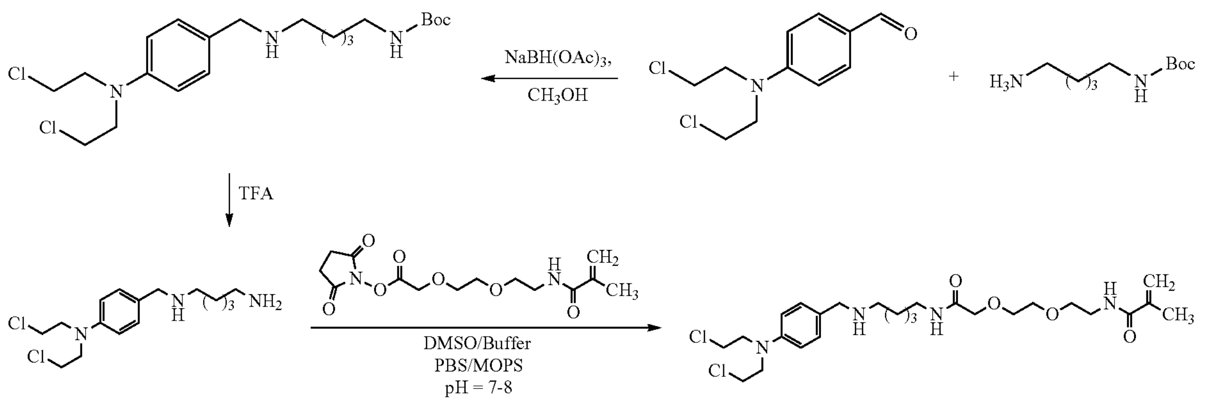
Example 56. Synthetic Route for Compound IIIB-5
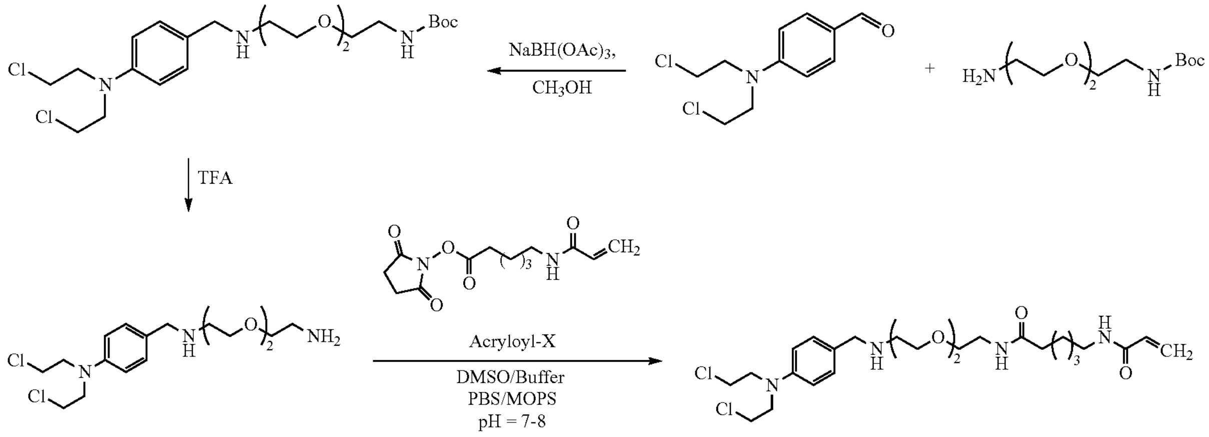
Example 57. Synthetic Route for Compound IIIB-6
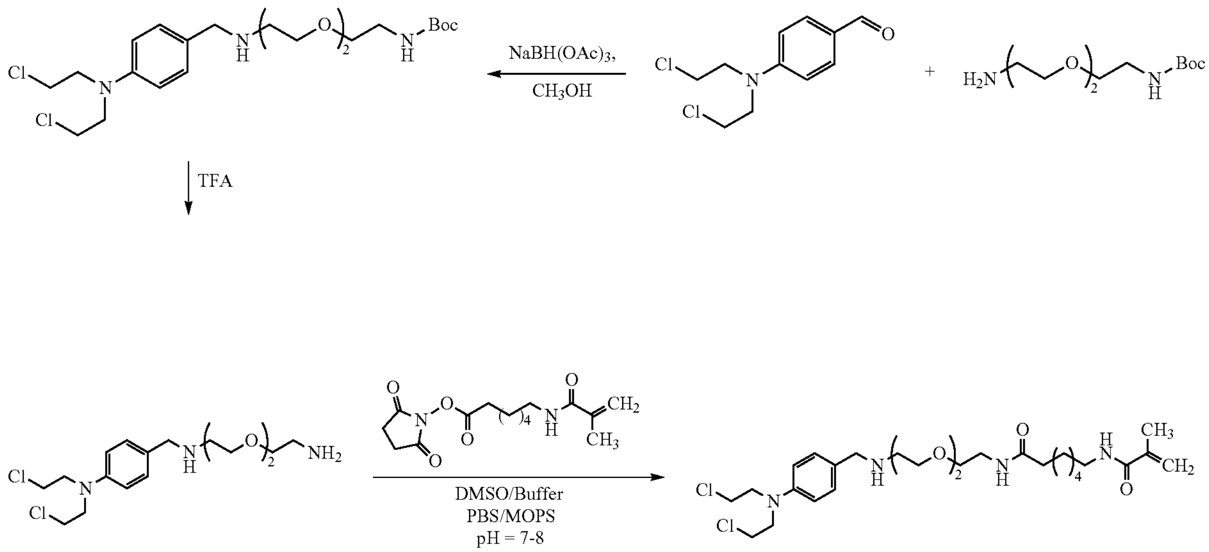

Example 58. Synthetic Route for Compound IIIB-7
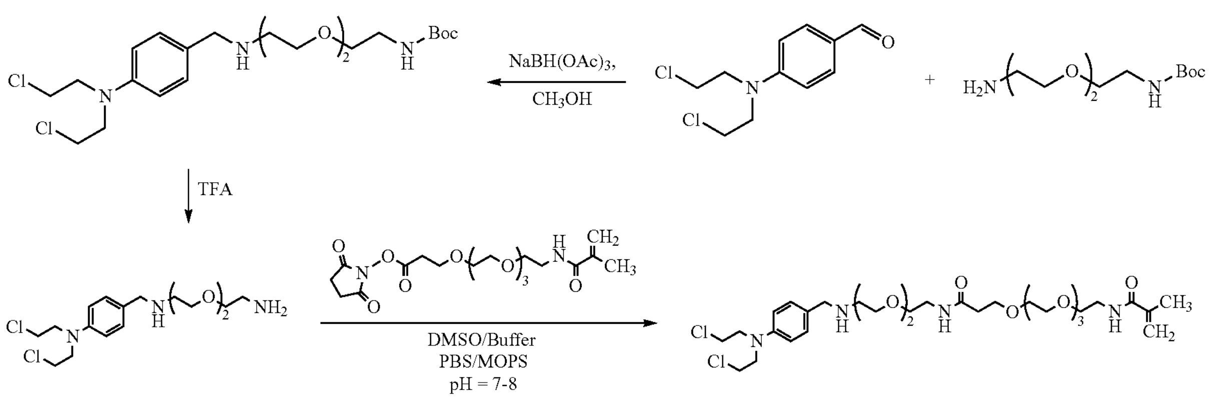
Example 59. Synthetic Route for Compound IIIB-8
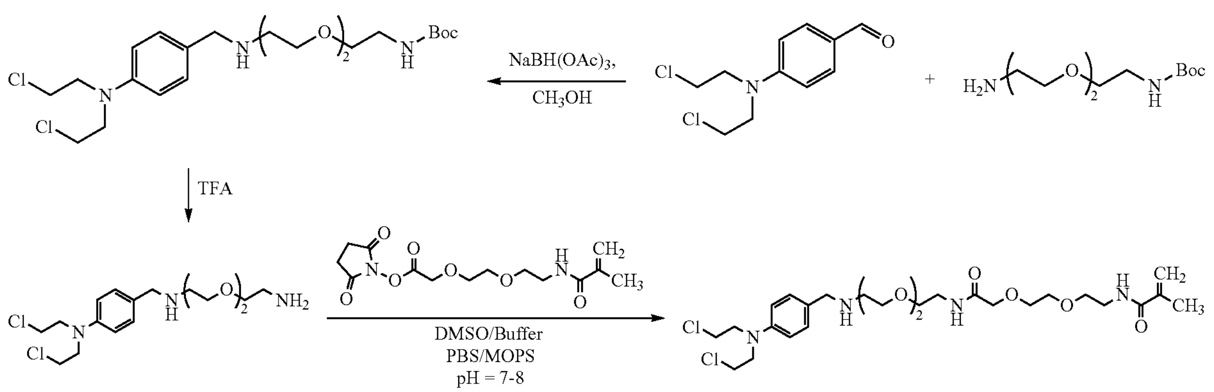
Example 60. Synthetic Route for Compound IIIB-9
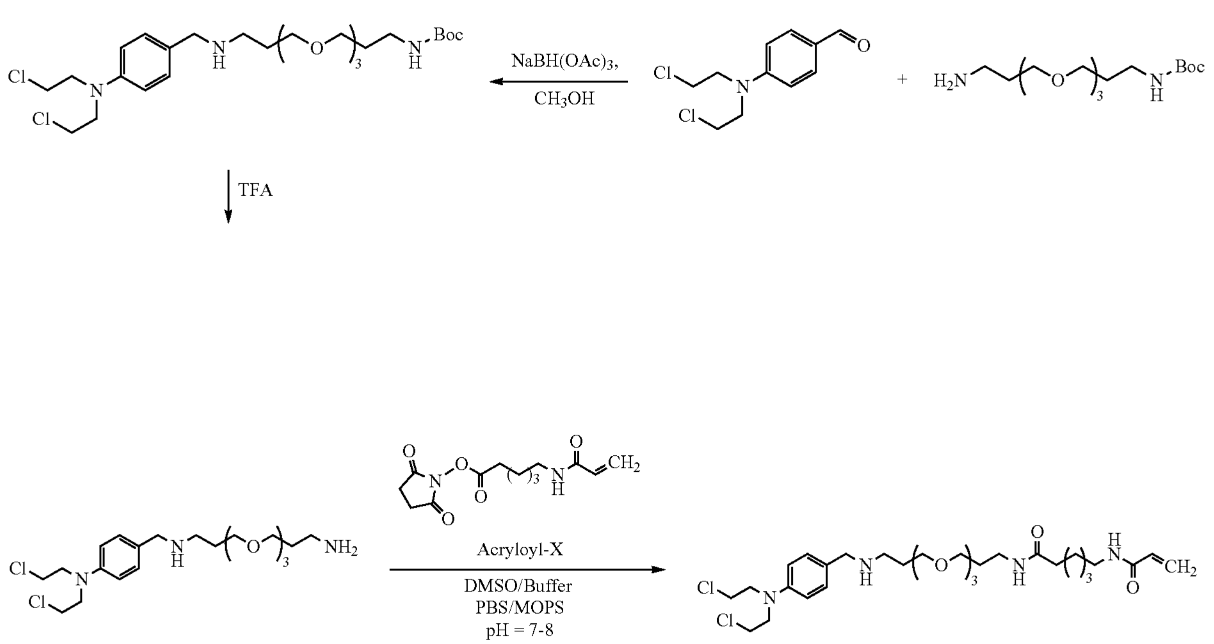

Example 61. Synthetic Route for Compound IIIB-10
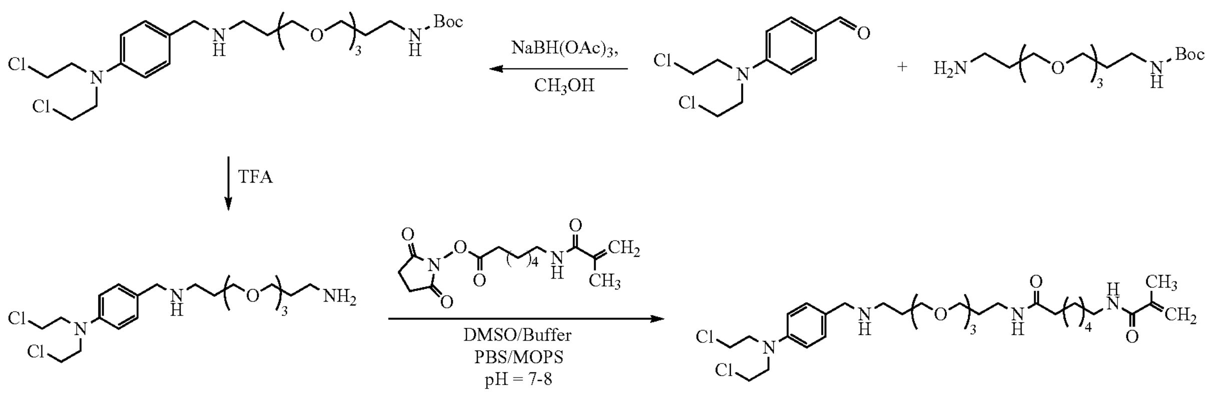
Example 62. Synthetic Route for Compound IIIB-11
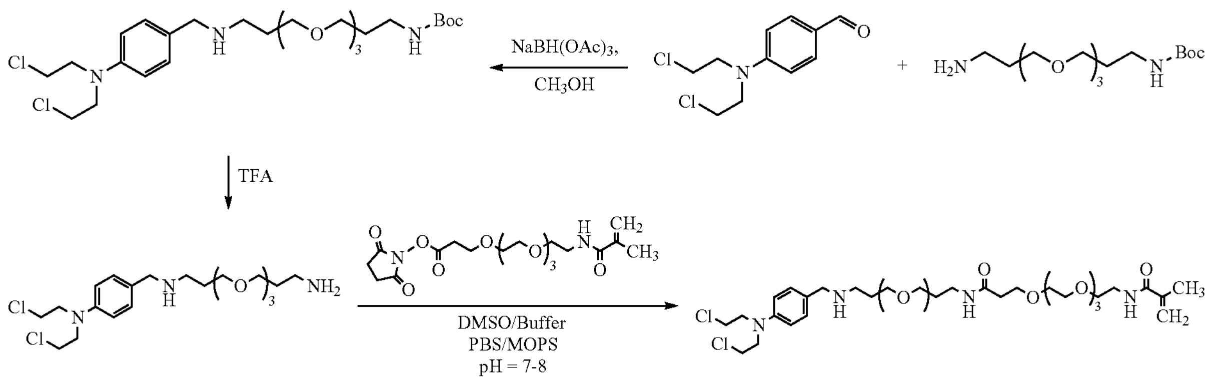
Example 63. Synthetic Route for Compound IIIB-12
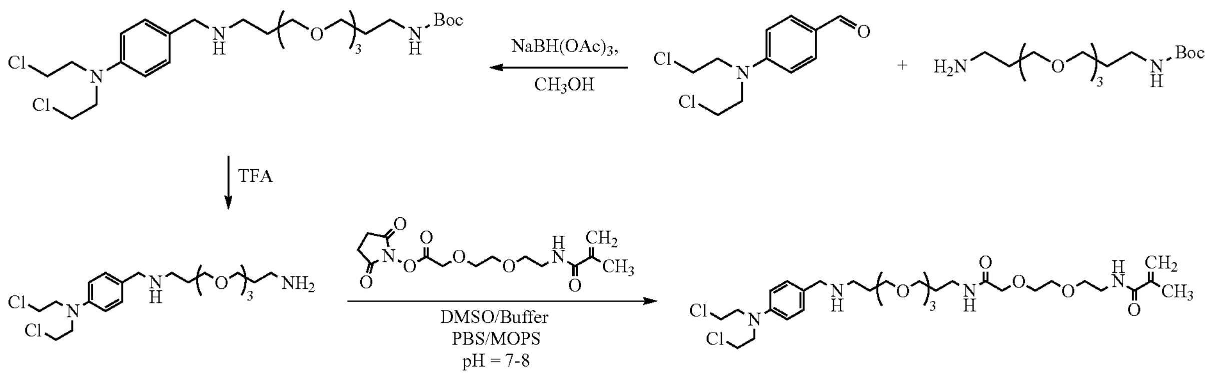
Example 64. Synthetic Route for Compound IIIB-13

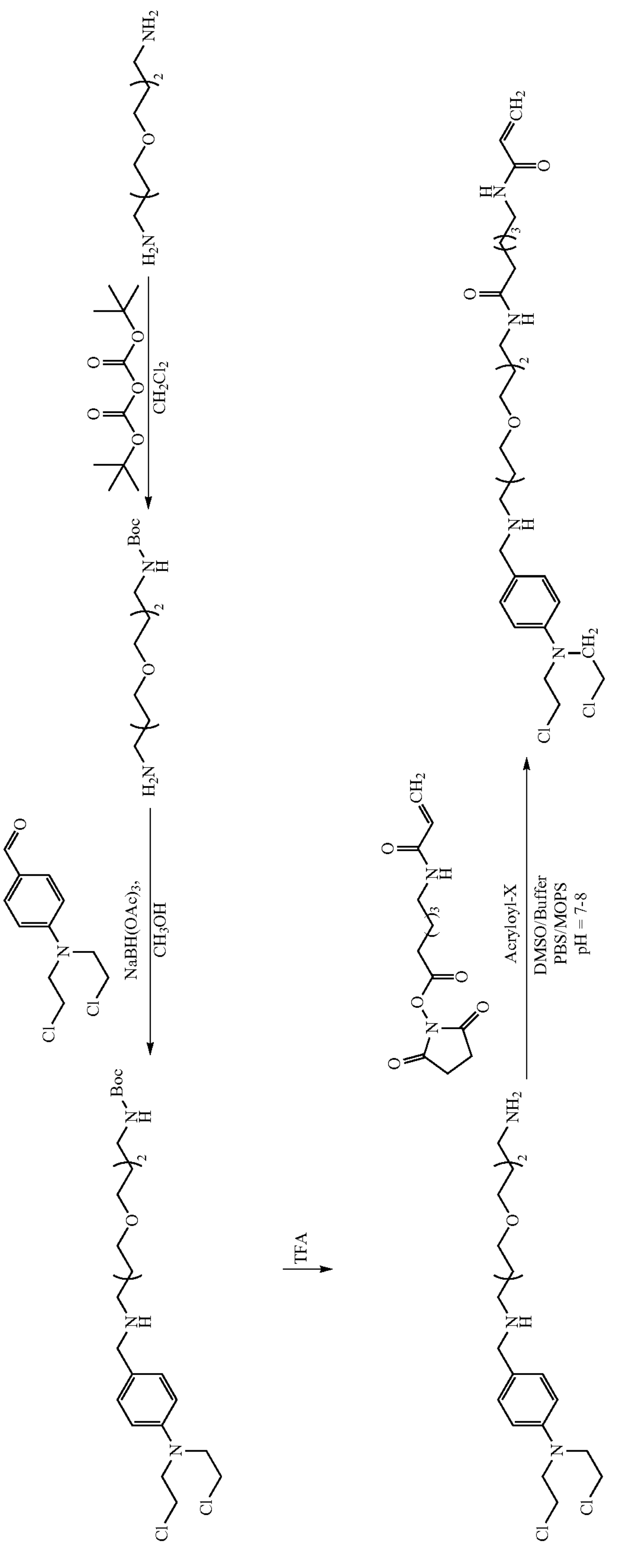
$CH_2Cl_2$
$NaBH(OAc)_3$,
$CH_3OH$
TFA
Acryloyl-X
DMSO/Buffer
PBS/MOPS
pH = 7-8

Example 65. Synthetic Route for Compound IIIB-14

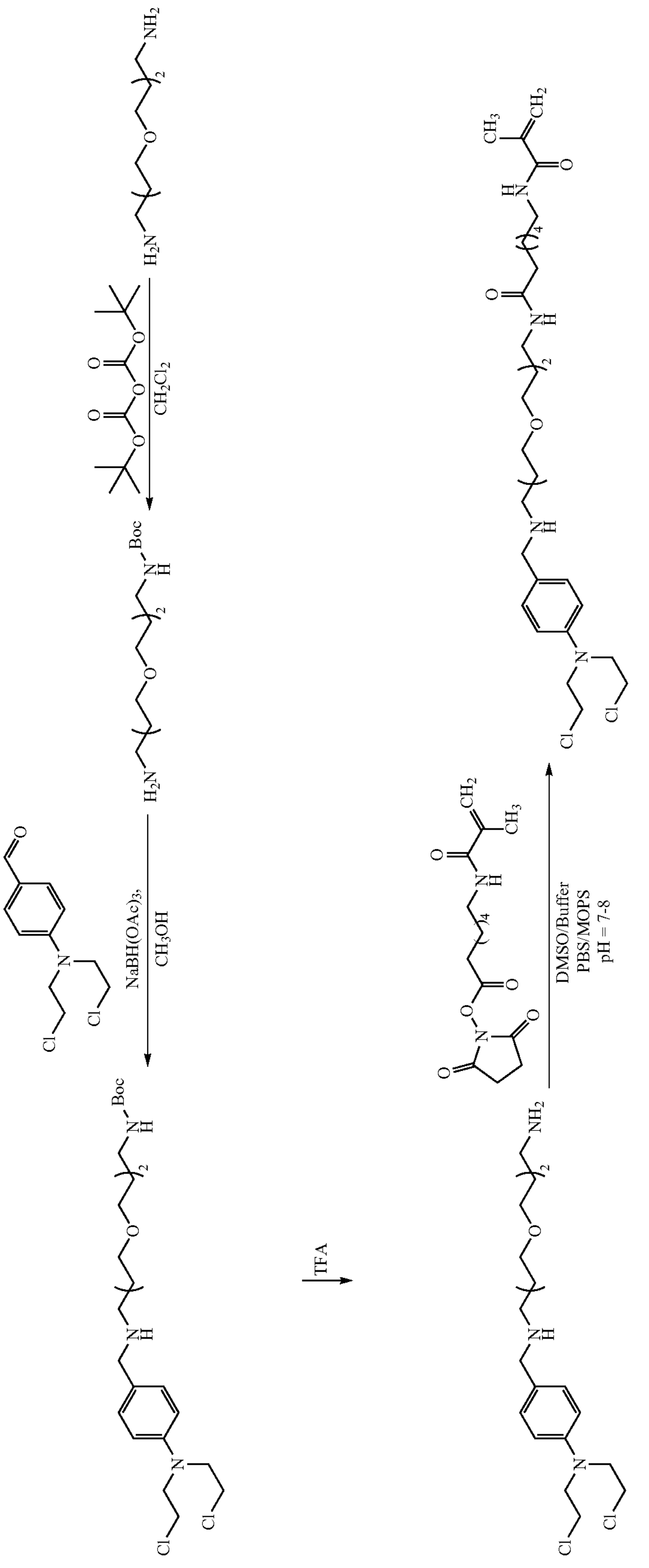
CH2Cl2
NaBH(OAc)3,
CH3OH
TFA
DMSO/Buffer
PBS/MOPS
pH = 7-8

Example 66. Synthetic Route for Compound IIIB-15

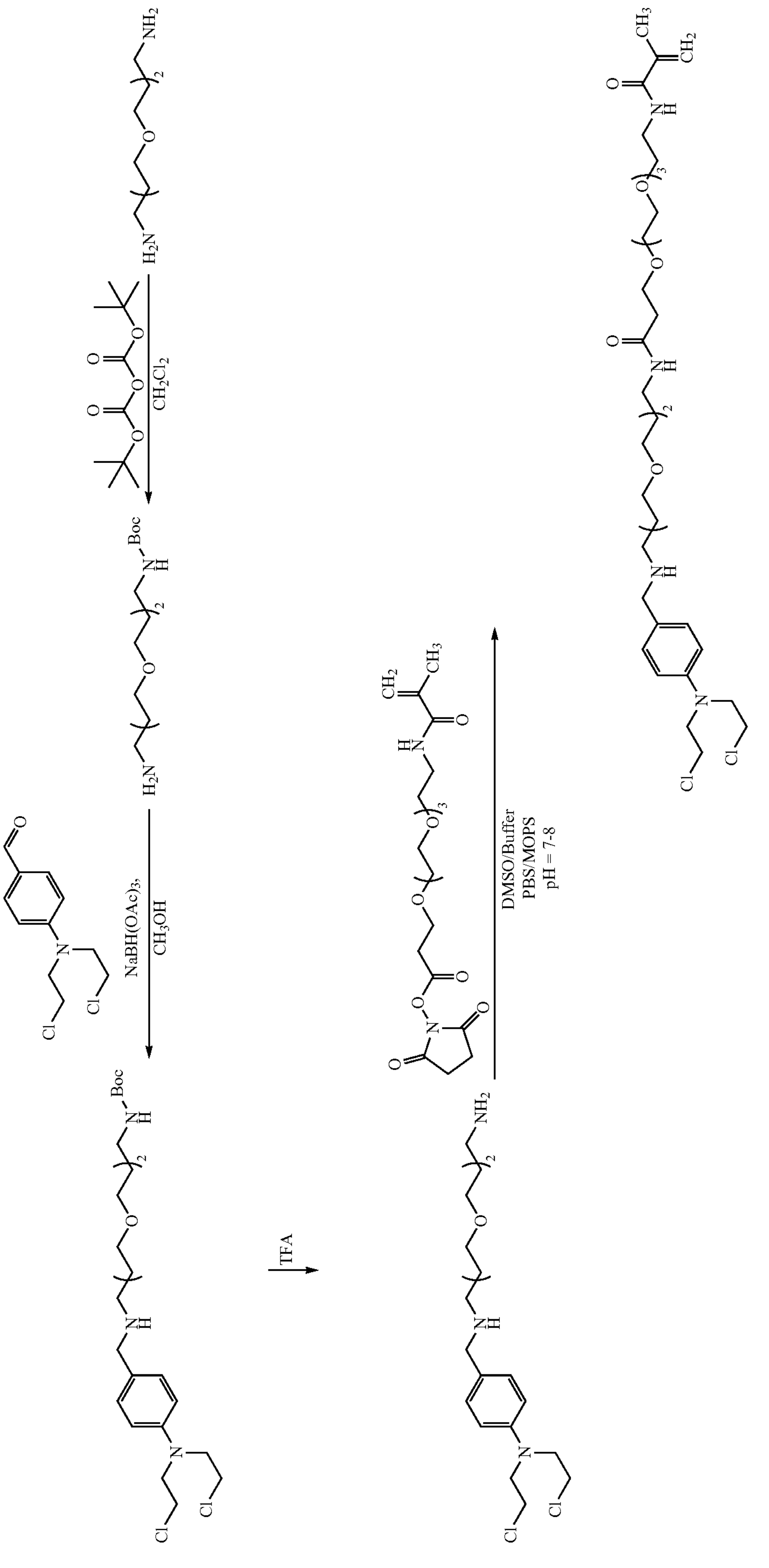
CH2Cl2
NaBH(OAc)3,
CH3OH
TFA
DMSO/Buffer
PBS/MOPS
pH = 7-8

Example 67. Synthetic Route for Compound IIIB-16

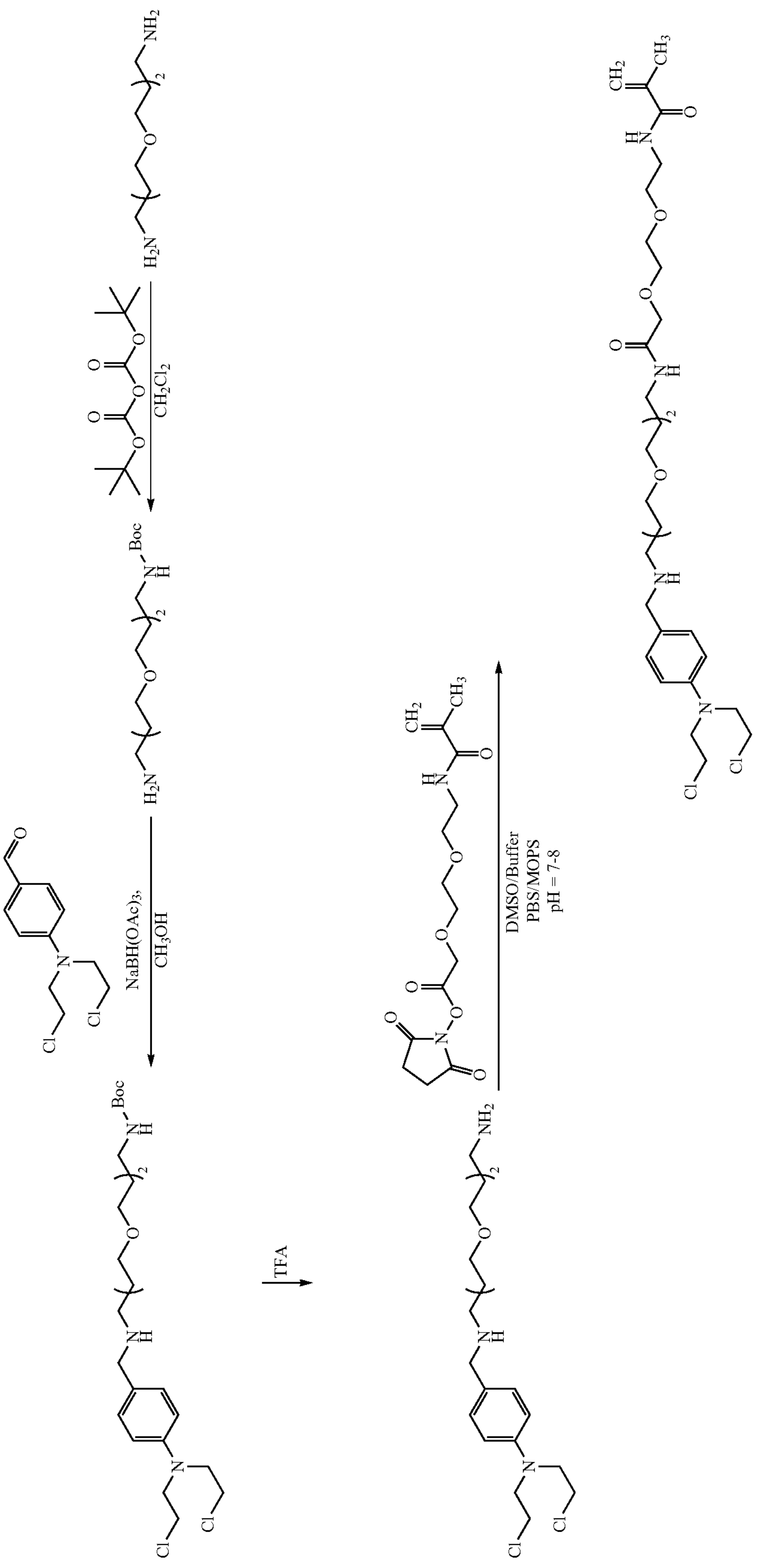
CH2Cl2
NaBH(OAc)3,
CH3OH
TFA
DMSO/Buffer
PBS/MOPS
pH = 7-8

Example 68. Synthetic Route for Compound IIIB-17

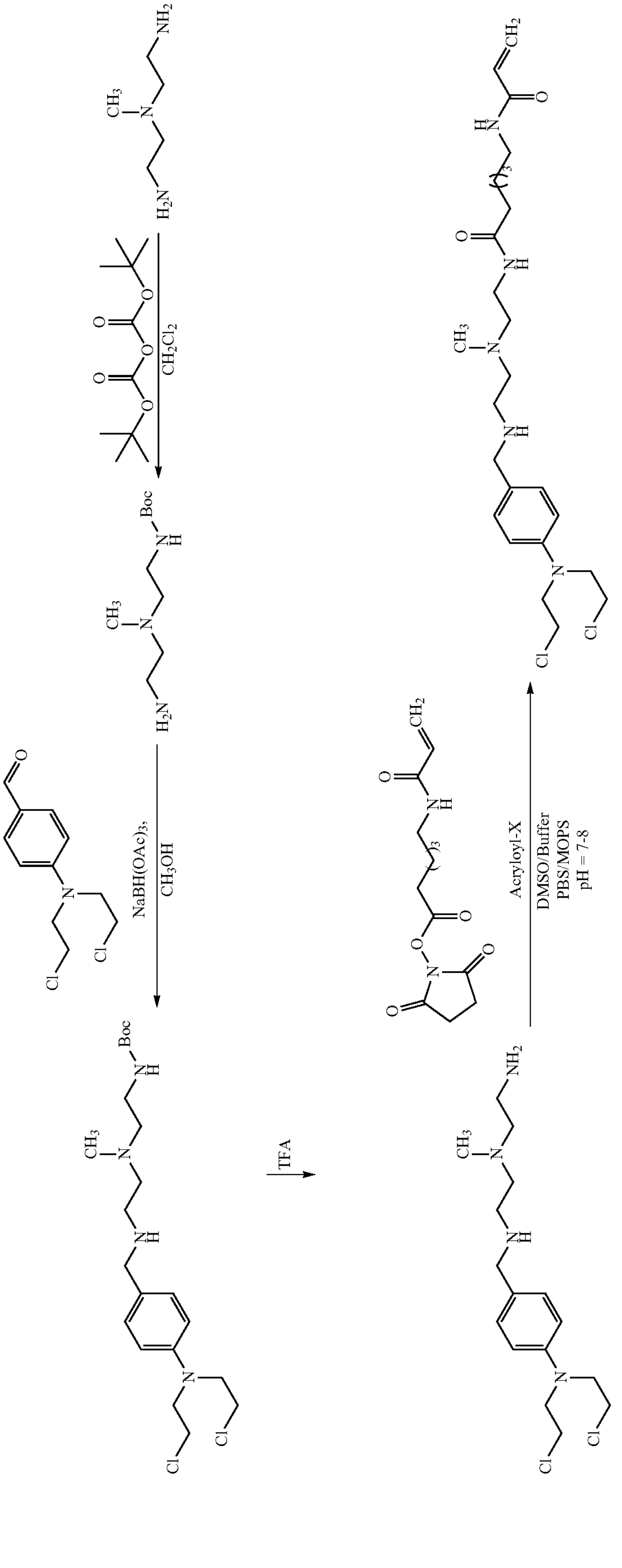
$CH_2Cl_2$
NaBH(OAc)$_3$,
$CH_3OH$
TFA
Acryloyl-X
DMSO/Buffer
PBS/MOPS
pH = 7-8

Example 69. Synthetic Route for Compound IIIB-18

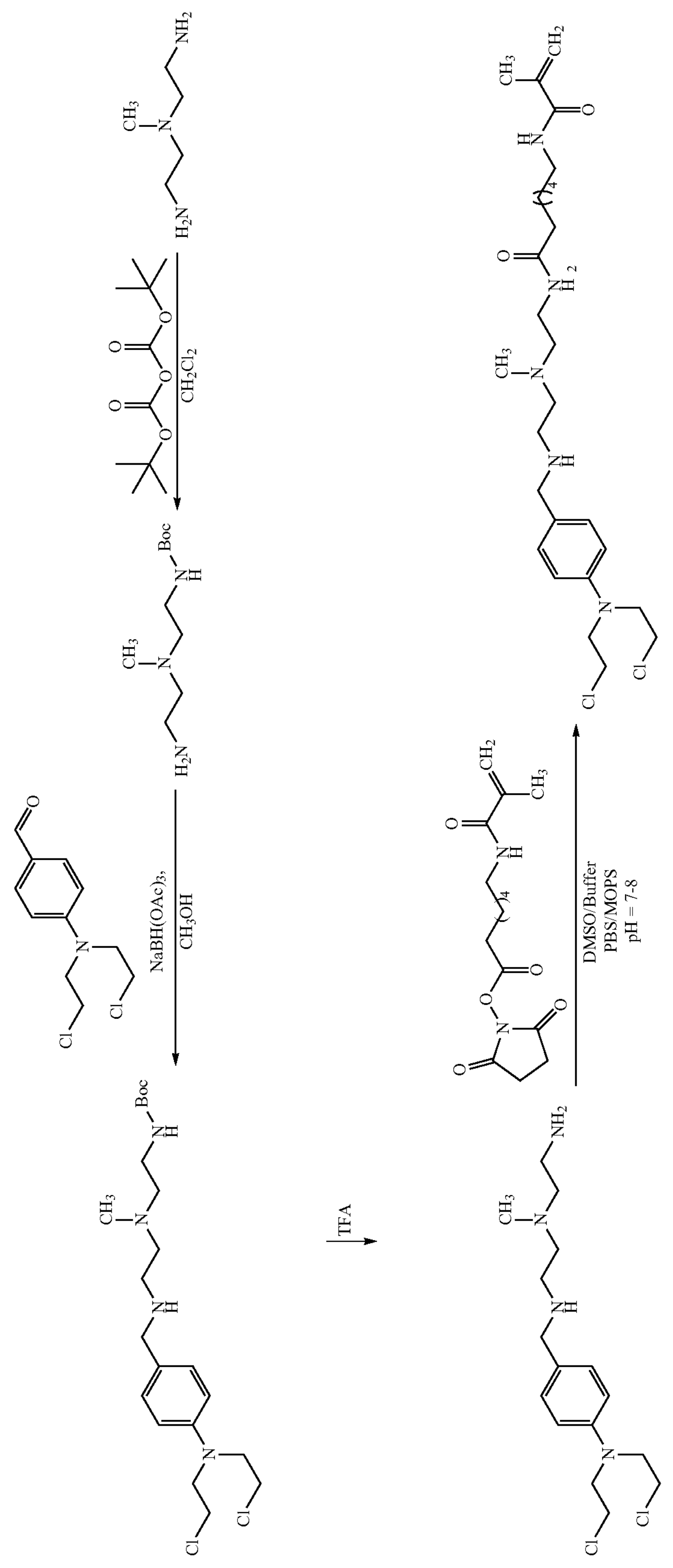
CH2Cl2
NaBH(OAc)3,
CH3OH
TFA
DMSO/Buffer
PBS/MOPS
pH = 7-8

Example 70. Synthetic Route for Compound IIIB-19

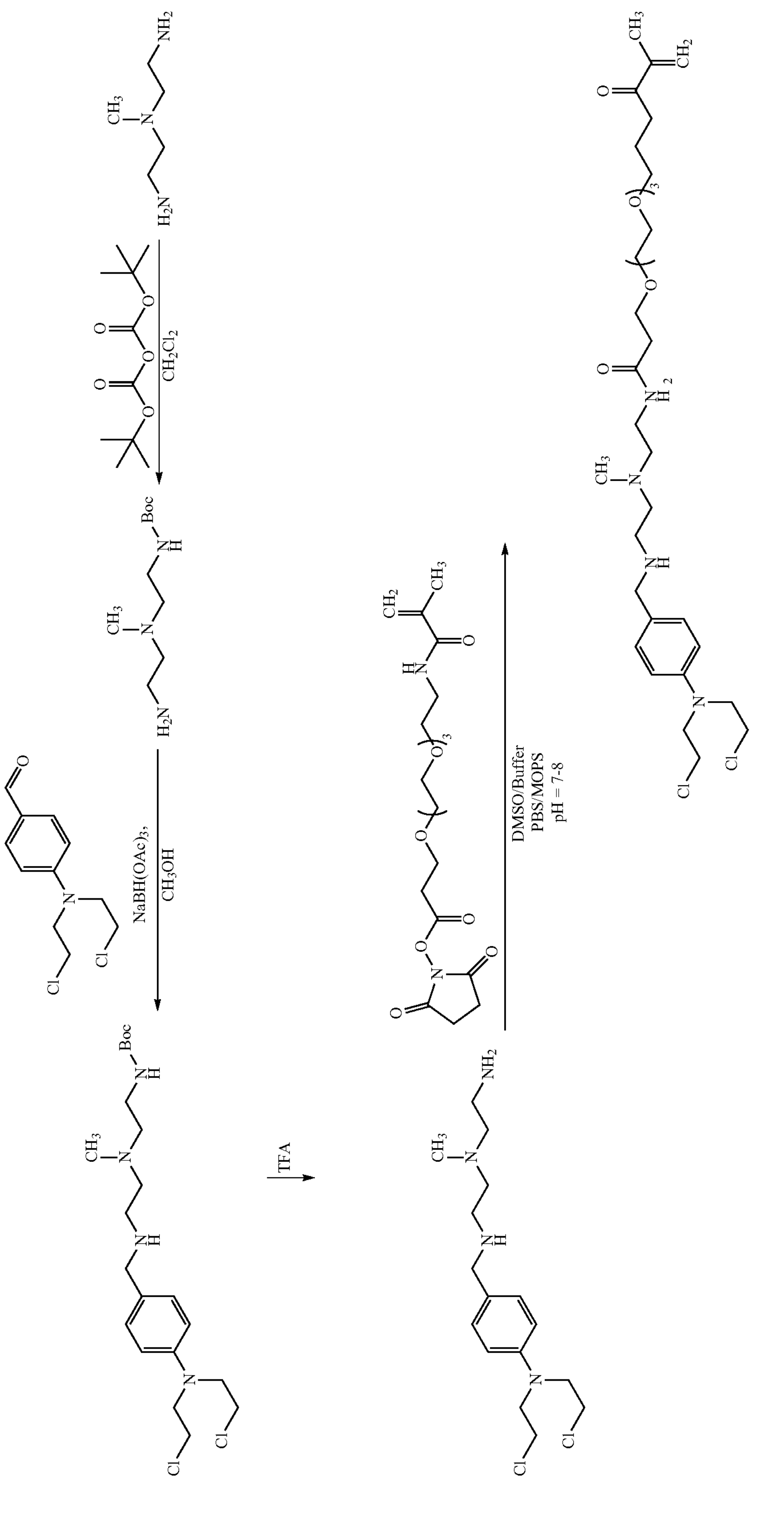
$CH_2Cl_2$
NaBH(OAc)$_3$,
$CH_3OH$
TFA
DMSO/Buffer
PBS/MOPS
pH = 7-8

Example 71. Synthetic Route for Compound IIIB-20

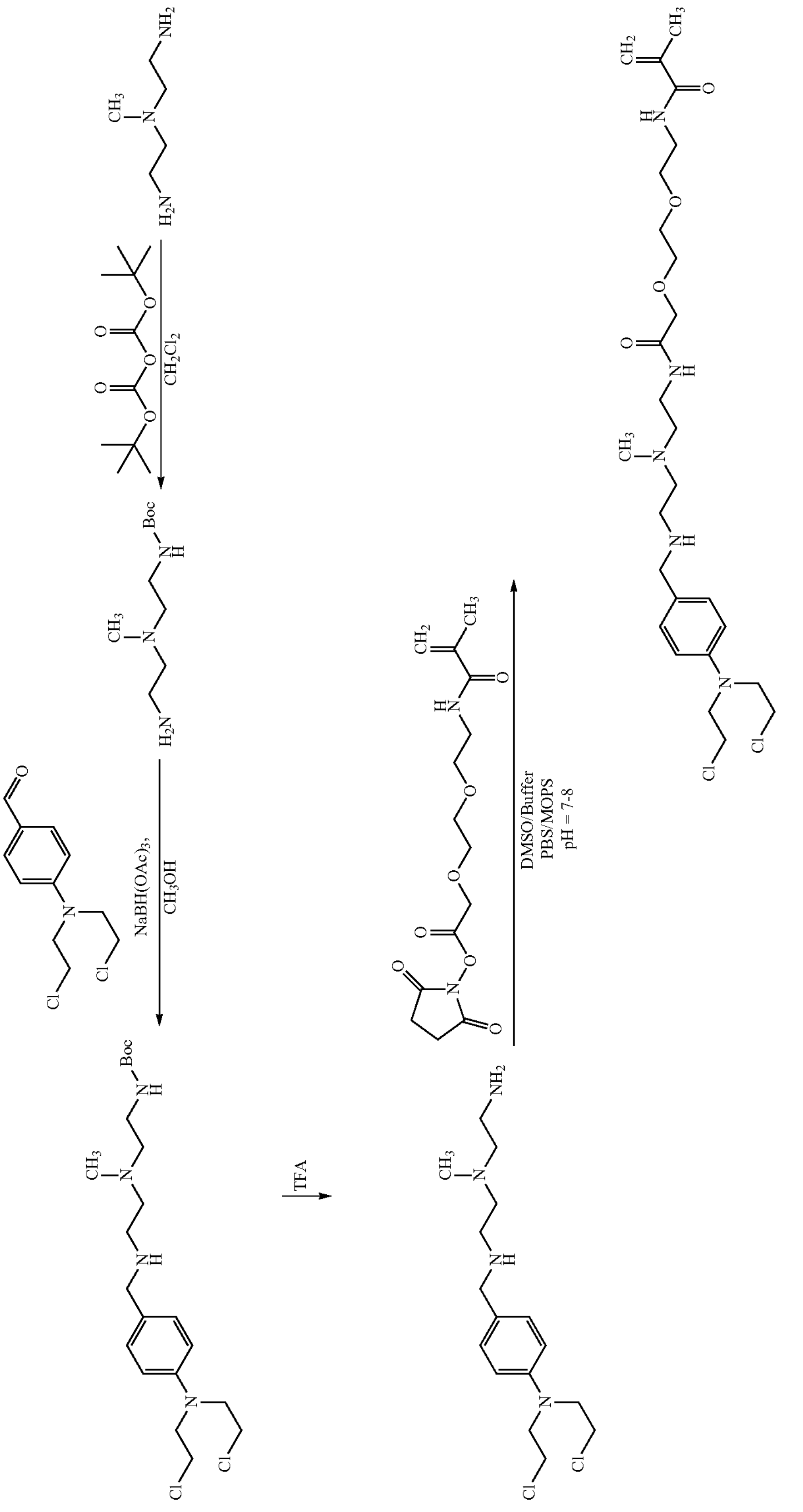
CH$_2$Cl$_2$
NaBH(OAc)$_3$,
CH$_3$OH
TFA
DMSO/Buffer
PBS/MOPS
pH = 7-8

Example 72. Expansion Microscopy Using Compounds of Formulas (I), (IIA-IIB) or (IIIA-IIIB)

Materials and Methods

Antibody staining, Polymerization and Expansion: Brain slices are taken from the cryo-protectant solution and washed with 1×PBS and blocked with blocking buffer (5% normal donkey serum and 0.1% TritonX-100 in 1×PBS) for 2 hours at room temperature or overnight at 4° C. Slices are incubated with respective primary and secondary antibodies for 6 hours at room temperature (RT) or overnight at 4° C. Upon washing with 1×PBS after each antibody incubation, slices are washed with MOPs buffer for 30 minutes, then incubated in a solution of anchoring reagents Compound I-1 of Formula (I) and Compound IIA-3 of Formula (II), 100 μg/mL each in MOPs buffer for 6 hours or overnight at room temperature. Anchoring reagent solution is removed and slices are washed with 1×PBS three times. Then slices are incubated in monomer solution for 10 minutes with rocking at RT. Polymerization is initiated by adding initiator (10% APS) and accelerator (10% TMED) reagents and incubated at room temperature for 2 hours. Once the polymerization completed tissue-gel composite is transferred into a Bind-Silane treated glass bottom 6 well plate and is subjected to digestion with Proteinase K in digestion buffer for overnight at room temperature with rocking. Digestion buffer is removed and gels are expanded by washing with cell culture grade water for 4 times 30 minutes each.

Gel Embedding in Polyacrylamide gel Matrix: Prepare embedding solution by mixing 3% acrylamide, 0.15% N,N'-Methylenebisacrylamide in 5 mM Tris or Borate buffer and adjust the pH to 10.5. Then add the embedding solution, 10% APS and 10% TMED to the expanded gel and incubate on a rocker for 15 minutes. Remove the embedding solution and repeat one more times. Then remove the embedding solution and place an appropriately cut glass slide on top of the gel and incubate at 37° C. for 2 hours.

Multiplexed in situ Hybridization: Re-embedded gel is incubated in wash buffer for 30 minutes at room temperature. Wash buffer is removed and 1 nM of initiator probe (Though 'n" number of initiator probes can be used, we use 3 probes per hybridization cycle) solution prepared in hybridization buffer is added and the gel is incubated at 37° C. for at least 18 hours. Hybridization buffer with initiator probe is removed and gel is washed wash buffer twice (60 minutes each at 37° C.). Wash buffer is removed and gel is washed with 1×PBS for 2 hours at 37° C. and PBS wash is repeated at room temperature instead of 37° C. 1×PBS is removed and gel is incubated with amplification buffer for 30 minutes at room temperature for pre-amplification. To prepare fluorescently labeled hairpin solution, each HCR hairpin is subjected to snap cooling procedure. In snap cooling procedure each hairpin is heated at 95° C. for 90 seconds, and cooled to room temperature on the benchtop for 30 minutes. Then hairpin solution (60 nM) is prepared by adding all snap-cooled hairpins to amplification buffer at room temperature. Amplification buffer is removed and fresh prepared hairpin solution is added to the gel and incubated for 2-4 hours at room temperature. To stop amplification hairpin solution is removed and gel is washed with 5×SSCT buffer 4 times with 30 minutes incubation each time. Gels are stained with DAPI (100 ng/μL) in water for 15 minutes. Gel is ready to image at this point. Andor Revolution Spinning Disk Confocal microscope is used for imaging. Gels are stored in 0.05×SSC buffer 4° C.

Probe removal by DNAse I digestion: To remove the probes and prepare the gel/specimen for next round of in situ hybridization with next set of probes, 0.05×SSC buffer is removed and gels are incubated with 0.25 U/μL of DNAse I in Reaction Buffer for at least 6 hours to overnight at 37° C. DNAse I is removed and the gel is washed with 1×PBS and stored in 1×PBS at 4° C. until imaging. Images are collected using Andor Revolution Spinning Disk Confocal microscope, then gel/specimen is proceeded with next round of in situ hybridization of next set of probes.

Bind-Silane treatment: Prepare Bind-Silane solution by mixing 5 μL of Bind-Silane, 8 mL of ethanol, 1.8 mL of nuclease free water and 0.2 mL of acetic acid in a falcon tube. Then add 1 mL Bind-silane solution to each well of glass bottom 6 well plate and incubate for 10 minutes at room temperature. Remove Bind-silane solution and let air dry for 10 minutes, wash twice with EtOH and let air dry for 30-60 minutes.

Sectioning and storing the Tissue: Mice approximately 8 weeks of age are euthanized by carbon dioxide asphyxiation and transcardially perfused with 1×PBS followed by 4% paraformaldehyde. Brains are harvested and incubated in 4% paraformaldehyde overnight. Brains are washed with 1×PBS and incubated in a solution of 30% Sucrose, 100 mM Glycine in 1×PBS at 4° C. for 48 hours. Once the brains are shrunk to the bottom of the tube, they are embedded by flash freezing in OCT. Then brains are sectioned on a cryostat with 50 μM size of each slice and stored in cryo-protectant solution (30% ethylene glycol+30 Sucrose+1×PBS) at −20° C. until staining.

Having described preferred embodiments with reference to the accompanying drawings, it is to be understood that the disclosure is not limited to the precise embodiments, and that various changes and modifications may be effected therein by those skilled in the art without departing from the scope or spirit of the disclosure as defined in the appended claims.

What is claimed is:

1. A compound of Formula IIA or IIB:

(IIA)

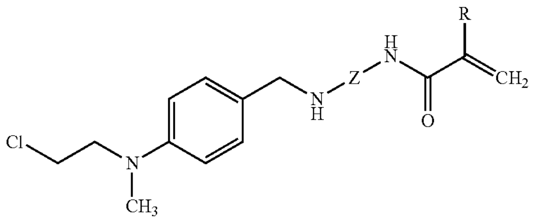

(IIB)

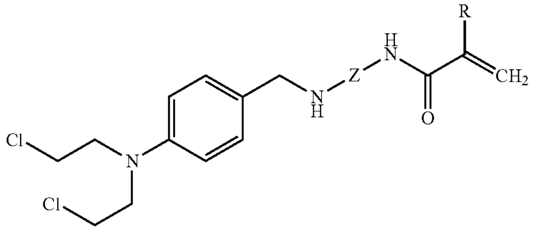

wherein Z is selected from among:

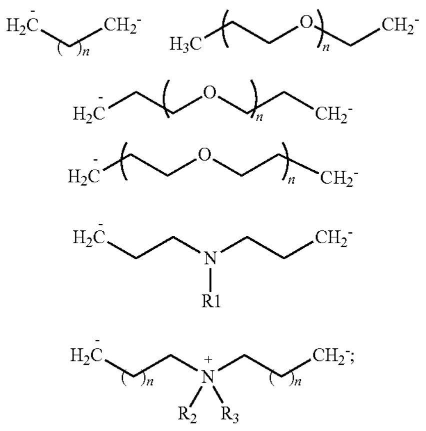

wherein each occurrence of n is independently 1, 2, 3, 4, 5, 6, 7 or 8;

R is selected from hydrogen, deuterium, halo, —CN, —$NO_2$, and an optionally substituted aliphatic, alicyclic, heteroaliphatic, heterocyclic, aromatic, acyl or heteroaromatic group; and R1, R2 and R3 are independently H, alkyl, acyl or allyl.

2. A compound of claim 1 selected from:

IIA-1

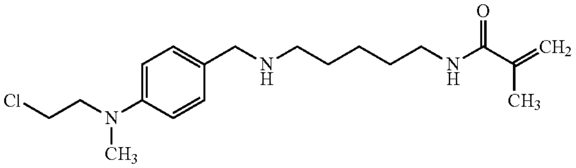

IIA-2

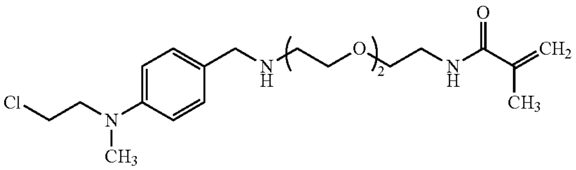

IIA-3

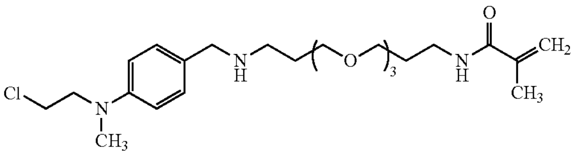

IIA-4

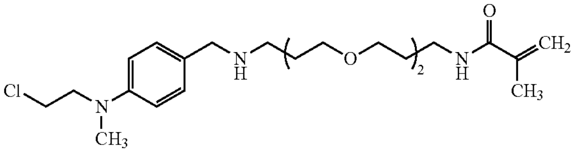

-continued

IIA-5

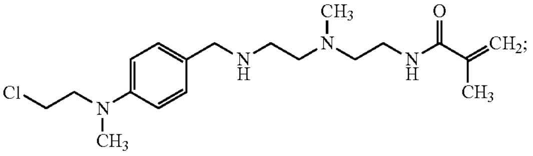

and

IIA-6

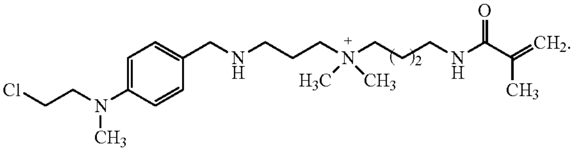

3. A compound of claim 1 selected from

IIB-1

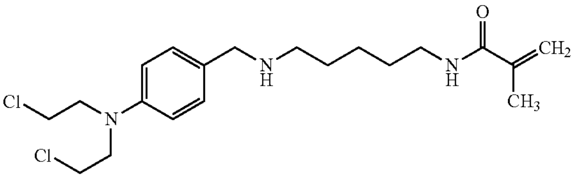

IIB-2

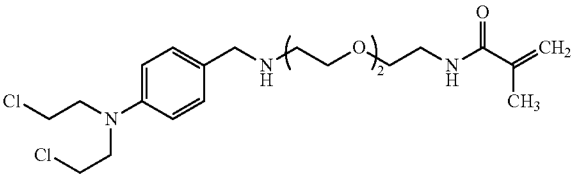

IIB-3

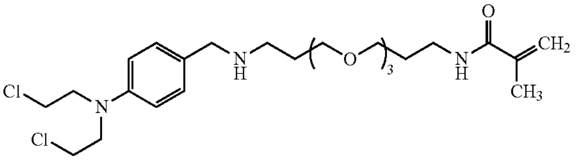

IIB-4

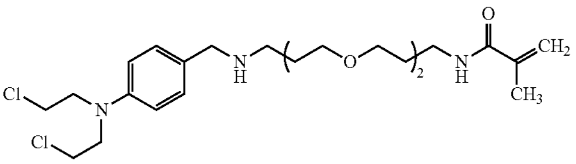

IIB-5

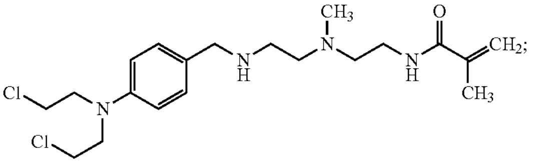

and

-continued

IIB-6

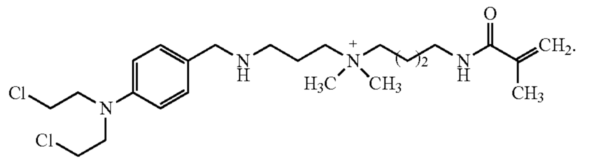

4. A method for preparing a compound of Formula IIA of claim 1

(IIA)

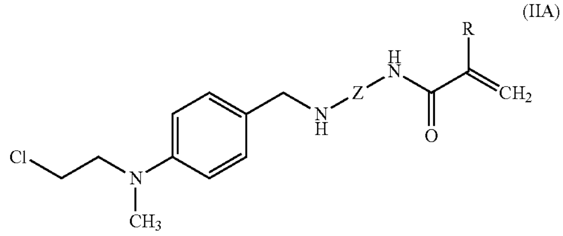

by the process of:

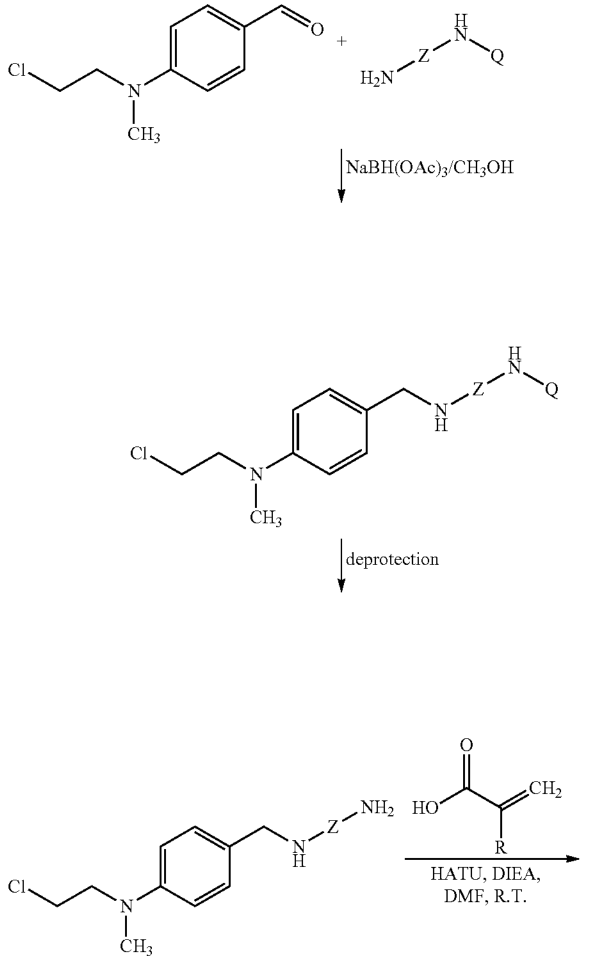

-continued

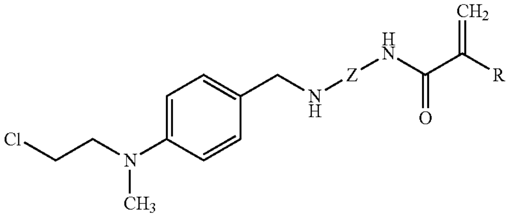

IIA

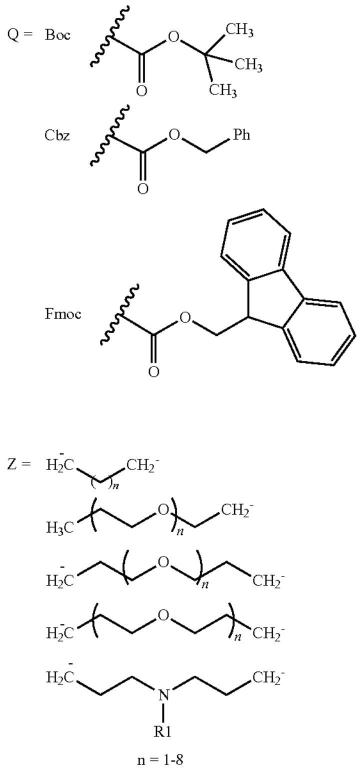

wherein the definitions of Z, Q and n are shown in the above scheme, wherein R is independently selected from hydrogen, deuterium, halo, —CN, —$NO_2$, and an optionally substituted aliphatic, alicyclic, heteroaliphatic, heterocyclic, aromatic, acyl or heteroaromatic group; and $R^1$ is H, alkyl, acyl or allyl.

5. The method of claim 4 wherein a protective group on Q other than Fmoc, Cbz or Boc is used.

6. A method for preparing a compound of Formula IIA of claim 1

(IIA)

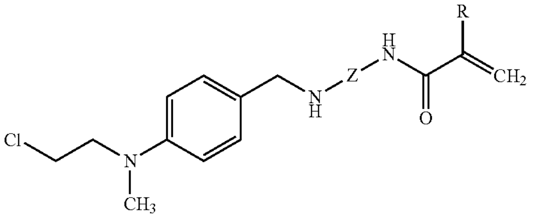

by the process of:

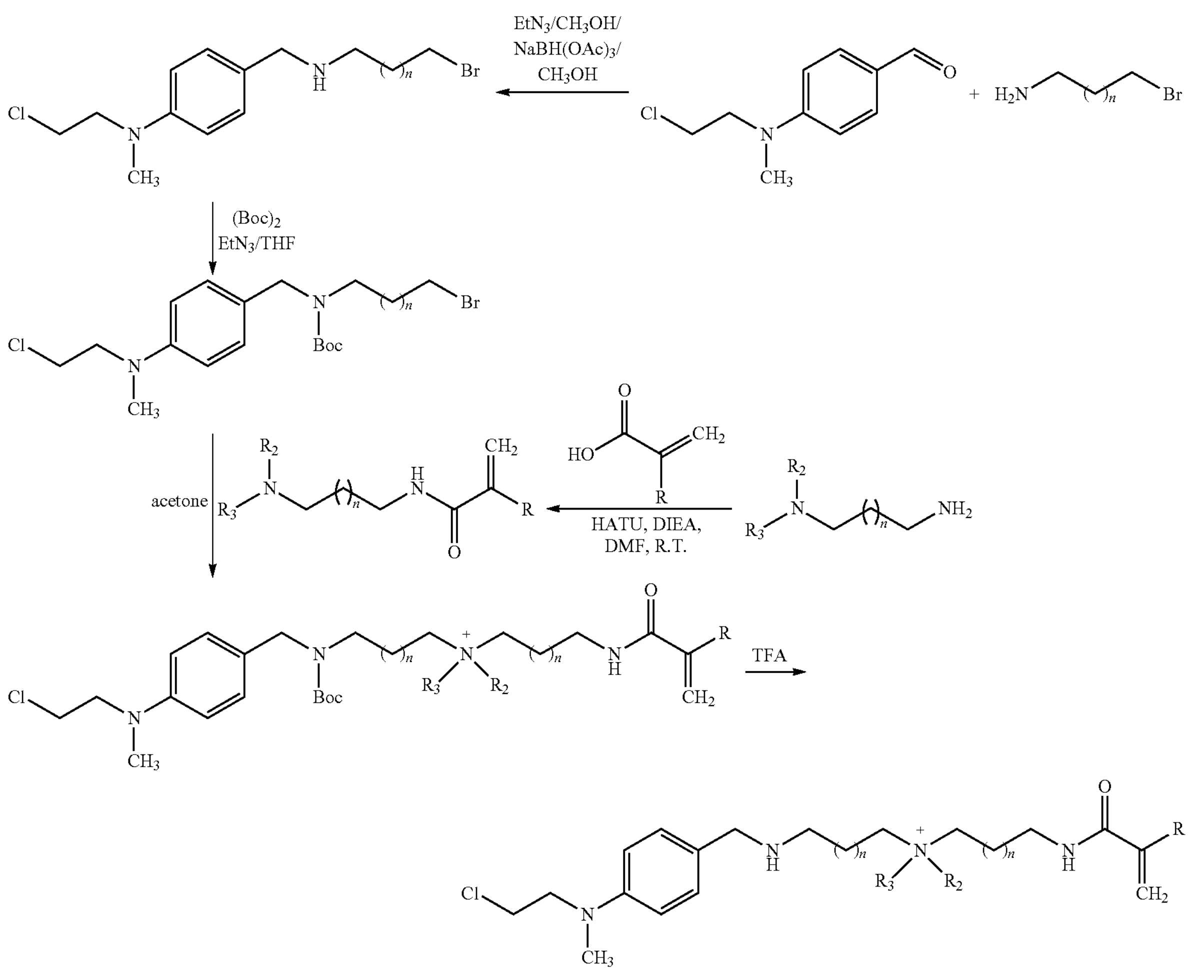

IIA n = 1-8 wherein each occurrence of n is independently 1-8; R is selected from hydrogen, deuterium, halo, —CN, —$NO_2$, and an optionally substituted aliphatic, alicyclic, heteroaliphatic, heterocyclic, aromatic, acyl or heteroaromatic group; and R2 and R3 are independently H, alkyl, acyl or allyl.

7. A method for preparing a compound of Formula IIB of claim 1

(IIB)

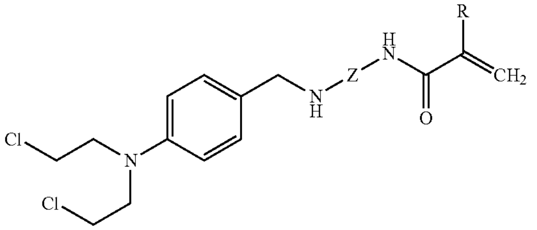

by the process of:

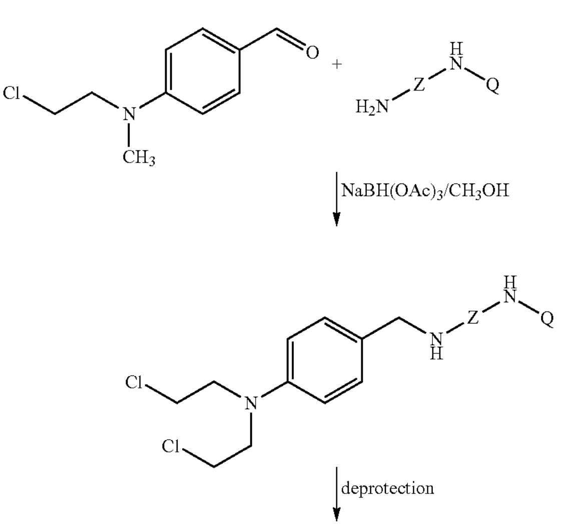

-continued

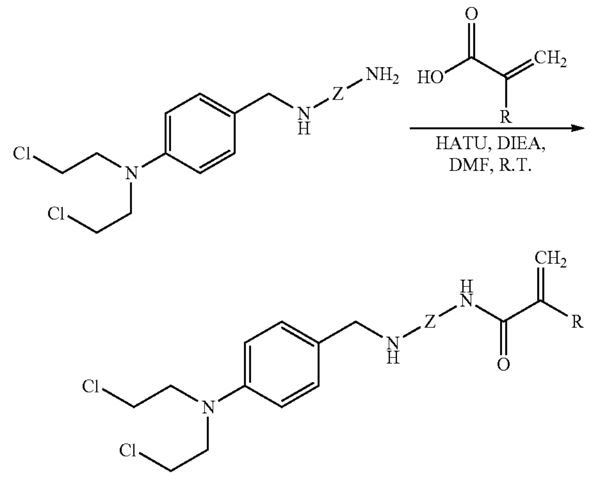

IIB

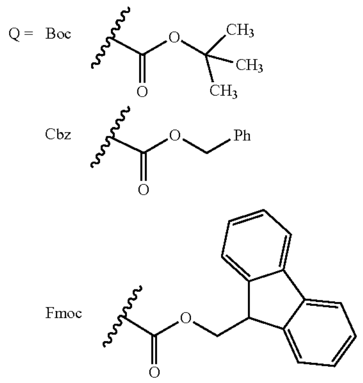

-continued

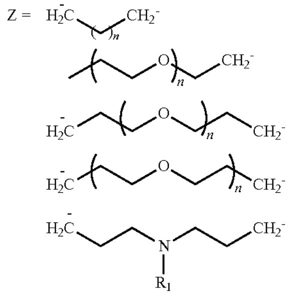

n = 1-8 wherein Z, n and Q are as defined in the above scheme; R is selected from hydrogen, deuterium, halo, —CN, —$NO_2$, and an optionally substituted aliphatic, alicyclic, heteroaliphatic, heterocyclic, aromatic, acyl or heteroaromatic group; and R1 is H, alkyl, acyl or allyl.

8. The method of claim 7 wherein a protective group on Q other than Fmoc, Cbz or Boc is used.

9. A method for preparing a compound of Formula IIB of claim 1

(IIB)

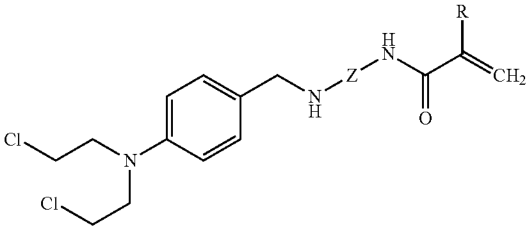

by the process of:

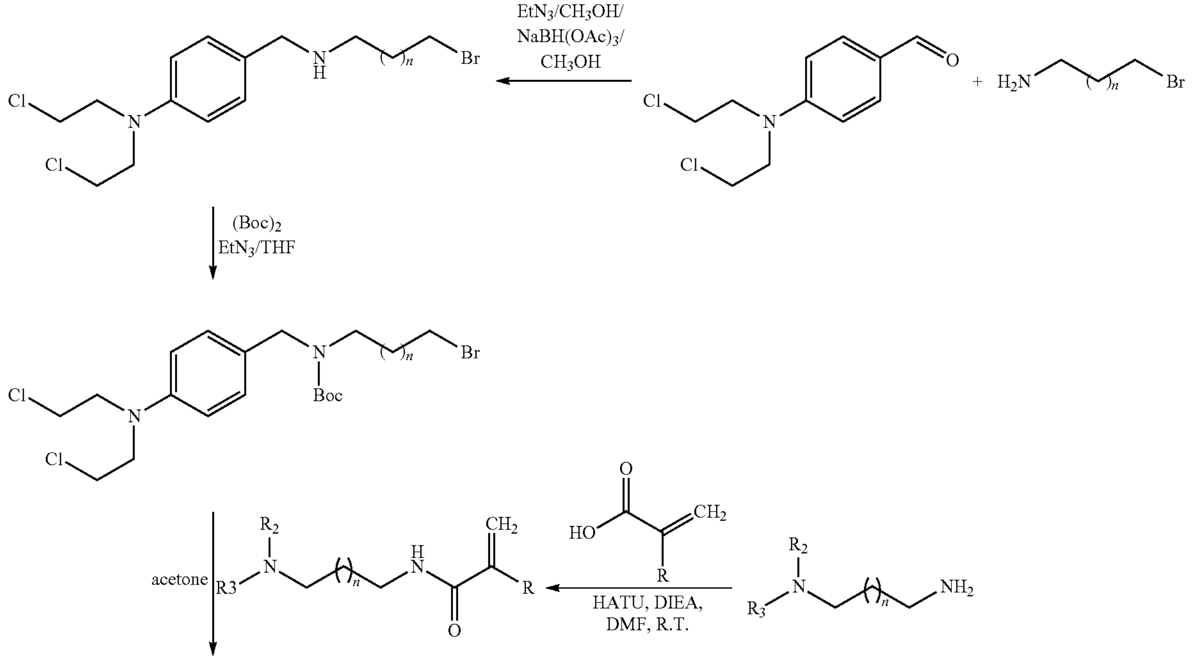

-continued
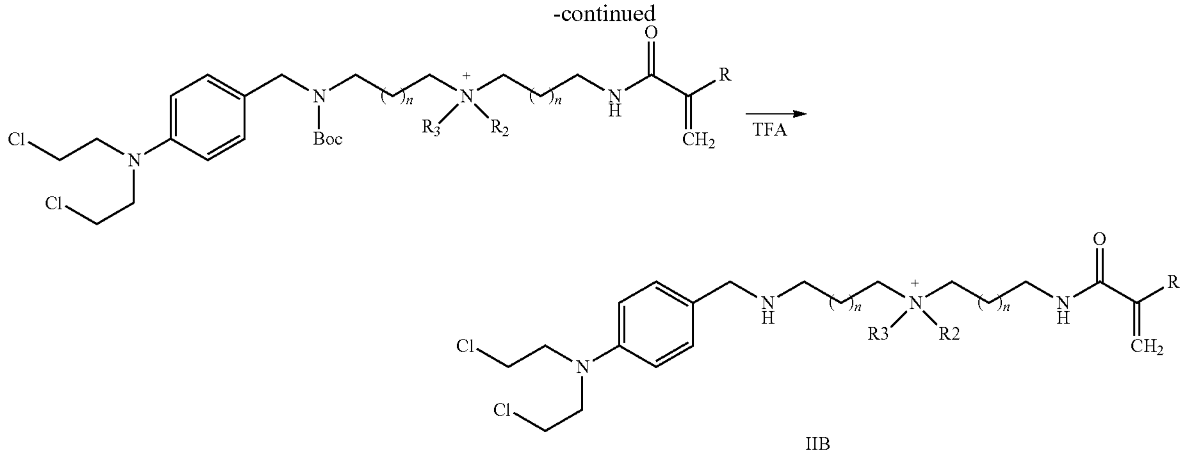
IIB
n = 1-8
wherein each occurrence of n is independently 1-8; R is selected from hydrogen, deuterium, halo, —CN, —$NO_2$, and an optionally substituted aliphatic, alicyclic, heteroaliphatic, heterocyclic, aromatic, acyl or heteroaromatic group; and R2 and R3 are independently H, alkyl, acyl or allyl.
* * * * *